US012746539B2

(12) United States Patent
Brodsky

(10) Patent No.: US 12,746,539 B2
(45) Date of Patent: Sep. 29, 2026

(54) MULTIPLEXED POLYMERASE CHAIN REACTION IN MICROPIPETTE FORMAT

(71) Applicant: Revvity Health Sciences, Inc., Waltham, MA (US)

(72) Inventor: Andrew Brodsky, Hopkinton, MA (US)

(73) Assignee: REVVITY HEALTH SCIENCES, INC., Waltham, MA (US)

( * ) Notice: Subject to any disclaimer, the term of this patent is extended or adjusted under 35 U.S.C. 154(b) by 506 days.

(21) Appl. No.: 18/493,701

(22) Filed: Oct. 24, 2023

(65) Prior Publication Data

US 2024/0050935 A1 Feb. 15, 2024

Related U.S. Application Data

(62) Division of application No. 17/187,331, filed on Feb. 26, 2021, now Pat. No. 11,872,551.

(60) Provisional application No. 62/983,479, filed on Feb. 28, 2020.

(51) Int. Cl.

| | |
|---|---|
| ***B01L 3/02*** | (2006.01) |
| ***C12Q 1/6848*** | (2018.01) |
| ***C12Q 1/686*** | (2018.01) |

(52) U.S. Cl.

CPC ............ *B01L 3/021* (2013.01); *C12Q 1/6848* (2013.01); *C12Q 1/686* (2013.01); *B01L 2200/026* (2013.01); *B01L 2300/14* (2013.01); *B01L 2300/1888* (2013.01)

(58) Field of Classification Search

CPC ........................................................ B01L 3/02

See application file for complete search history.

(56) References Cited

U.S. PATENT DOCUMENTS 5,720,923 A * 2/1998 Haff ..................... B01J 19/0046 422/138
9,821,305 B2 * 11/2017 Michels .................. B01L 3/021
10,513,729 B2 12/2019 Aguanno et al.

(Continued)

FOREIGN PATENT DOCUMENTS

CN 1938423 A 3/2007
CN 103917293 A 7/2014

(Continued)

OTHER PUBLICATIONS

Heng et al., "Development of fully automatic fatty acid value measuring instrument" *Storage of Grains* 1:42-44 and 47, Feb. 2018. (9 pages).

(Continued)

*Primary Examiner* — Aaron A Priest

(74) *Attorney, Agent, or Firm* — Seed Intellectual Property Law Group LLP

(57) ABSTRACT

A system may include a horizontal actuator to move a tray, to which a microwell plate and a microfluidic chip may be coupled. The system may include a vertical actuator to move a support arm, to which a plurality of pipettes or pipette tips may be coupled. The system may include a rotational actuator to move an angle bracket, to which a magnet may be coupled. The system may include a heater, through which the pipettes may extend. The system may include a pump to control the flow of fluids through the pipettes. Disclosed methods include performing PCR within the described system.

12 Claims, 56 Drawing Sheets

(56) References Cited

U.S. PATENT DOCUMENTS

| | | | | |
|---|---|---|---|---|
| 10,883,987 | B2 | 1/2021 | Strong et al. | |
| 10,913,200 | B2 * | 2/2021 | Maggiore | B29C 48/02 |
| 11,400,445 | B2 | 8/2022 | Schmid | |
| 11,530,175 | B2 | 12/2022 | Taeschler et al. | |
| 11,813,613 | B2 | 11/2023 | Arlett et al. | |
| 12,258,555 | B2 * | 3/2025 | Lee | C12M 47/12 |
| 2003/0122779 | A1 | 7/2003 | Martin et al. | |
| 2005/0019951 | A1 | 1/2005 | Gjerde et al. | |
| 2008/0003588 | A1 | 1/2008 | Hasson et al. | |
| 2008/0003594 | A1 | 1/2008 | Hasson et al. | |
| 2008/0044311 | A1 * | 2/2008 | Iguchi | G05D 23/24 422/63 |
| 2008/0241844 | A1 | 10/2008 | Kellogg | |
| 2009/0227006 | A1 | 9/2009 | Kopp et al. | |
| 2010/0173394 | A1 | 7/2010 | Colston, Jr. et al. | |
| 2016/0184743 | A1 | 6/2016 | Marshall et al. | |
| 2017/0023599 | A1 | 1/2017 | Richards et al. | |
| 2018/0015474 | A1 | 1/2018 | Arlett et al. | |
| 2020/0055042 | A1 | 2/2020 | Steinert et al. | |
| 2022/0259542 | A1 | 8/2022 | Maeda et al. | |

FOREIGN PATENT DOCUMENTS

| | | | | | |
|---|---|---|---|---|---|
| CN | 107312068 | A | | 11/2017 | |
| CN | 107427836 | A | | 12/2017 | |
| CN | 110007102 | A | | 7/2019 | |
| CN | 110291400 | A | | 9/2019 | |
| CN | 209979663 | U | | 1/2020 | |
| CN | 112774756 | A | * | 5/2021 | B01L 9/54 |
| JP | H0866652 | A | | 3/1996 | |
| JP | 2005508058 | A | | 3/2005 | |
| JP | 2011097955 | A | | 5/2011 | |
| JP | 2016534333 | A | | 11/2016 | |
| JP | 2019536030 | A | | 12/2019 | |
| JP | 7075544 | B2 | | 5/2022 | |
| WO | 97/48818 | A1 | | 12/1997 | |
| WO | 01/49415 | A2 | | 7/2001 | |
| WO | 2016/069091 | A1 | | 5/2016 | |
| WO | 2017119382 | A1 | | 7/2017 | |
| WO | 2018/139132 | A1 | | 8/2018 | |
| WO | 2019139135 | A1 | | 7/2019 | |
| WO | WO-2019147722 | A1 | * | 8/2019 | C12N 15/1013 |

OTHER PUBLICATIONS

Xu et al., "A self-contained all-in-one cartridge for sample preparation and real-time PCR 2 in rapid influenza diagnosis," *Lab Chip* 10:3103-3111, Sep. 2010. (9 pages).

Yue Chaochi et al., "Expression of SREBP-1 in colorectal cancer tissues and its clinical significance," *Chinese Journal of Gerontology* 37(23), Dec. 10, 2017. (4 pages).

A.M. Comer et al., "Detection of mRNA species in bulbospinal neurons isolated from the rostral ventrolateral medulla using single-cell RT-PCR", *Brain Research Protocols* 4, Jul. 5, 1999. (11 pages).

* cited by examiner

MULTIPLEXED POLYMERASE CHAIN REACTION IN MICROPIPETTE FORMAT

BACKGROUND

Technical Field

The technology described herein relates to processing of samples such as biological samples, for example, the separation of contaminants from a biological sample contained on a substrate, for example, in conjunction with polymerase chain reaction of nucleic acids derived from a complex sample, such as blood.

Description of the Related Art

It is well known that nucleic acids can be collected for analytical testing. A major challenge in the collection of nucleic acids from, for example, blood is that the biosamples quite often contain contaminates. Therefore, nucleic acid sample purification has become an important step in experimental workflows as the quality of the sample nucleic acids may affect the performance in downstream applications, especially in contaminant-sensitive applications such as polymerase chain reaction (PCR).

A host of common nucleic acid purification techniques include centrifugation, chemical separation, or a solid phase-based separation. These techniques, however, are time and labor intensive and quite often require the use of specialized equipment.

The use of microfluidics in the analysis of biological and chemical samples is well known. One such use involves a system that utilizes a microfluidic chip (sometimes referred to as a "lab-on-a-chip") to obtain one or more samples, to process the sample for measurement, and then to assess the composition. However, the samples must be purified to remove contaminates to ensure the quality of downstream applications.

PCR is one downstream application that requires purified nucleic acid samples and tight control of reaction conditions to avoid cross-contamination. Multiplexed purification of nucleic acid samples, followed by PCR of the purified samples on the same microfluidic chip is therefore challenging and systems and methods for improvement of the same are needed.

Thus, there is a need in the art to improve the process of purifying biological samples, and amplifying nucleic acids therein, without the need for expensive and highly specialized equipment.

BRIEF SUMMARY

Embodiments of the present technology are directed to performing PCR in a multiplexed format within cannulas or tubes that may also be used for transferring and/or dispensing samples and reagents for isolation and purification of samples in a microfluidic format. The PCR methods described herein may be used in combination with the isolation and purification techniques described herein such that a sample may be purified and nucleic acid obtained therefrom amplified in a single assay using the same instrument. However, isolation and/or purification of a sample on the described instrument is not required, and the methods and apparatus described herein are equally useful for PCR of pre-purified nucleic acids obtained from various sources. PCR reagents and methods are known in the art and described in more detail in WO 2011/094577, which is incorporated by reference in its entirety.

A method may be summarized as comprising: operating a pump to draw a biological sample from a well of a well plate into a pipette through a pipette tip of the pipette; operating a first actuator to move a first valve to a closed position to seal the biological sample within the pipette from the pipette tip; operating the pump to apply a positive gage pressure to the biological sample within the pipette; operating a second actuator to move a second valve to a closed position to seal the biological sample within the pipette from the pump; and operating a heater to heat the biological sample within the pipette, wherein a polymerase chain reaction occurs within the heated biological sample within the pipette between the first valve and the second valve.

Another method may be summarized as comprising: operating a pump to draw a biological sample from a well of a well plate into a first pipette conduit through a first pipette tip; operating a first actuator to move a first valve to a closed position to seal the biological sample within the first pipette conduit from the first pipette tip; operating the pump to apply a positive gage pressure to the biological sample within the first pipette conduit; operating a second actuator to move a second valve to a closed position to seal the biological sample within the first pipette conduit from the pump; and operating a heater to heat the biological sample within the first pipette conduit, wherein a chemical reaction occurs within the heated biological sample within the first pipette conduit between the first valve and the second valve.

A system may be summarized as comprising: a first pipette including a first pipette tip and a first end of the first pipette opposite to the first pipette tip along a first length of the first pipette; a second pipette including a second pipette tip and a second end of the second pipette opposite to the second pipette tip along a second length of the second pipette; a three-way connector that fluidically couples the second end of the first pipette to the second end of the second pipette and fluidically couples the second ends of the first and second pipettes to a feeder conduit; and a heating element thermally coupled to at least a portion of the first and second lengths.

The isolation and purification technology described herein, which may be performed separately from, or in advance of PCR, uses electric fields and/or gels, such as polyether compounds, to separate bioanalytes, such as nucleic acids, from a biological sample contained on a substrate. According to a first example of this technology, a method for separating bioanalytes comprises: providing a first well and a second well that are connected to each other via a micro channel. A fluid, such as a buffer, is provided in the first well into which the biological sample is placed. Magnetic beads, for example, magnetic particles based on polyvinyl alcohol (M-PVA Magnetic Beads) are then introduced into the first well. The surfaces of the M-PVA Magnetic Beads can be functionalized with many different groups and modified with individually tunable loadings. In one example, the M-PVA Magnetic Beads can be tuned to isolate nucleic acids in the biological sample, which may comprise blood.

The M-PVA Magnetic Beads isolate nucleic acids in the biological sample and draw the target molecules to the M-PVA Magnetic Beads. An electric field is then applied to the first well that interacts with negatively charged contaminates in the buffer. A magnet, external to the first well, is then brought in proximity to the first well. The magnet functions to attract the M-PVA Magnetic Beads such that, when the magnet is externally moved toward the microchannel, the M-PVA Magnetic Beads along with the target molecules attracted thereto, are pulled toward and into the microchannel. However, most of the negatively charged contaminates are maintained in the first well due to their interaction with the electric field. The magnet continues along its path in the microchannel toward the second well pulling the M-PVA Magnetic Beads and target molecules into the second well. The microchannel also contains a buffer and the movement of the M-PVA Magnetic Beads through the buffer in the microchannel further functions to shed contaminates from the target molecules such that by the time the M-PVA Magnetic Beads reach the second well, the target molecules are essentially free of contaminates.

At this point, the M-PVA Magnetic Beads can be withdrawn from the second well with the target molecules still attached and placed into a chamber where the M-PVA Magnetic Beads can be de-tuned to shed the target molecules and then be removed. The result is a very clean biological sample that is essentially free of contaminates. There is no need for expensive or specialized equipment, such as is needed for centrifugation, chemical separation, or solid phase-based separation. Rather, this technique can be implemented in a simple microfluidic chip format with few moving parts and without the need for extensive power requirements.

In some examples, a third well can be connected with the second well via a second microchannel. In this configuration, once the magnet has moved the M-PVA Magnetic Beads with the target molecules into the second well, the magnet can then be moved toward the second microchannel thereby pulling the M-PVA Magnetic Beads out of the second well and into the second microchannel. The magnet can then be moved toward the third well such that the M-PVA Magnetic Beads are pulled into the third well. This configuration provides another cleaning stage to the biological sample for applications which require it, for example PCR.

In some examples, it is considered that additional cleaning of the biological sample could be achieved by creating a flow of buffer from the second well toward the first well. This could be achieved by a simple fluid volume differential between the wells. In one example, the second well could be provided with a greater volume of fluid than is provided in the first well. For example, a fluid volume differential in the range of 20% to 50% could be provided, which may produce a desirable flow rate. This additional volume could be added after the biological sample is inserted into the first well, such that the flow of fluid from the second well through the microchannel and into the first well occurs during the movement of the M-PVA Magnetic Beads from the first well to the second well. This flow of fluid will function to carry any contaminates that escaped from the first well out of the microchannel and back into the first well.

In some examples, the electric field is applied to the first well or chamber by the application of first and second electrical conductors. A source of electrical power is connected to the first and second electrical conductors for creating a difference in electrical potential energy between the conductors. Additionally, software can be used to control the source of electrical power so as to develop a desired voltage between the conductors. It is contemplated that the software can actively control the magnitude of the voltage across the conductors.

In some examples, the system further may comprise a motor coupled to the first electrical conductor and adapted to move the first electrical conductor into and out of the first well. Likewise, the system may further comprise a motor coupled the second electrical conductor and adapted to move the second electrical conductor into and out of the first well.

In some examples, the system may comprise a motor coupled to a delivery system for insertion of the M-PVA Magnetic Beads into the first well and for fully automatic movement of the magnet that functions to pull the M-PVA Magnetic Beads from the first well into the microchannel and into the second well. Likewise, the system may further comprise a motor coupled to the magnet to withdraw the M-PVA Magnetic Beads from the second well and for insertion into the chamber.

In some examples, the M-PVA Magnetic Beads are tuned to attract deoxyribonucleic acid, while in other examples, the M-PVA Magnetic Beads are tuned to attract ribonucleic acid. The isolated and purified nucleic acid can then optionally be amplified via PCR as described herein.

In one example, a method for removing contaminants from a biological sample is provided comprising the steps of providing a first well and a second well connected to each other via a micro channel and providing a fluid in the first well, the second well and the microchannel. The method further comprises the steps of placing the biological sample into the first well, introducing magnetic beads into the first well and drawing target molecules within the biological sample to the magnetic beads. The method still further comprises the steps of applying an electric field to the first well, the electric field interacting with the contaminates, introducing a magnet generating a magnetic field into the vicinity of the first well, the magnet field interacting with the magnetic beads and moving the magnet toward the microchannel, the magnetic beads being drawn along with the movement of the magnet such that the magnetic beads and the target molecules are drawn into the microchannel. The method is provided such that the electric field acts on the contaminates so as to maintain the contaminates in the first well as the magnetic beads and target molecules move into the microchannel. Finally, the method comprises the step of moving the magnet toward the second well, the magnetic beads and target molecules being drawn along with the movement of the magnet such that the magnetic beads and target molecules are drawn into the second well. Optionally, purified nucleic acid obtained the sample in such methods is further amplified via PCR as described herein.

In another example, a system for removing contaminants from a biological sample, for example to prepare a sample for PCR, is provided comprising a first well adapted to contain a fluid and receive the biological sample, a second well adapted to contain a fluid and a microchannel extending between the first well and the second well. The system is provided such that magnetic beads are adapted to be introduced into the first well, the magnetic beads tuned to attract target molecules in the biological sample. The system further comprises a source of electrical power and two probes coupled to the source of electrical power, the two probes adapted to apply an electric field to the first well. The system is provided such that when electrical power is applied to the two probes, the two probes are adapted to generate and electric field there between with the contaminates interacting with the electric field. The system still further comprises a magnet adapted to be moved into the vicinity of the first well, the magnet is adapted to generate a magnetic field to interact with the magnetic beads. The system is further provided such that the magnet is provided to be moved toward the microchannel so that the magnetic beads are drawn along with the movement of the magnet and into the microchannel. Additionally, the electric field is adapted to interact with the contaminates such that the contaminates are maintained in the first well and the magnet is adapted to move toward the second well such that the magnetic beads and target molecules are drawn into the second well.

The M-PVA Magnetic Beads isolate nucleic acids in the biological sample and draw the target molecules to the M-PVA Magnetic Beads. A magnet, external to the first well, is then brought in proximity to the first well. The magnet functions to attract the M-PVA Magnetic Beads such that, when the magnet is moved toward the microchannel, the M-PVA Magnetic Beads along with the target molecules attracted thereto, are pulled toward and into the microchannel. The microchannel is filled with a polyether compound, such as, polyethylene glycol (PEG) also known as polyethylene oxide or polyoxyethylene depending on its molecular weight. The contaminates are negatively charged particles. When the negatively charged contaminates are drawn into the PEG, the PEG functions to block progression of those negatively charged species through the microchannel.

The magnet continues along its path in the microchannel toward the second well pulling the M-PVA Magnetic Beads and target molecules into the second well. By the time the M-PVA Magnetic Beads reach the second well, the target molecules are essentially free of contaminates, which have been shed in the PEG.

At this point, the M-PVA Magnetic Beads can be withdrawn from the second well with the target molecules still attached and placed into a chamber where the M-PVA Magnetic Beads can be de-tuned to shed the target molecules and then be removed. The result is a very clean biological sample that is essentially free of contaminates. There is no need for expense or specialized equipment, such as is needed for centrifugation, chemical separation, or solid phase-based separation. Rather, this technique can be implemented in a simple microfluidic chip format with few moving parts or the need for extensive power requirements.

In some examples, a third well can be connected with the second well via a second microchannel. In this configuration, once the magnet had moved the M-PVA Magnetic Beads with the target molecules into the second well, the magnet could then be moved toward the second microchannel thereby pulling the M-PVA Magnetic Beads out of the second well and into the second microchannel. The second microchannel can also include PEG. The magnet could then be moved toward the third well such that the M-PVA Magnetic Beads are pulled into the third well. This configuration provides another cleaning stage to the biological sample for applications which require it.

It is still further anticipated that the first well and the second well could comprise a gel, such as PEG, which would function to still further clean the biological sample.

In some examples, it is considered that additional cleaning of the biological sample could be achieved by creating a flow of the gel from the second well toward the first well. This could be achieved by a simple fluid volume differential of the gel between the wells. In one example, the second well could be provided with a greater volume of gel than is provided in the first well. This additional volume could be added after the biological sample is inserted into the first well, such that the flow of gel from the second well through the microchannel and into the first well occurs during the movement of the M-PVA Magnetic Beads from the first well to the second well. This flow of fluid will function to carry any contaminates that escaped from the first well out of the microchannel and back into the first well.

In some examples, the system may comprise a motor coupled to a delivery system for insertion of the M-PVA Magnetic Beads into the first well and for fully automatic movement of the magnet that functions to pull the M-PVA Magnetic Beads from the first well into the microchannel and into the second well. Likewise, the system may further comprise a motor coupled to the magnet to withdraw the M-PVA Magnetic Beads from the second well and for insertion into the chamber.

In some examples, the M-PVA Magnetic Beads are tuned to attract deoxyribonucleic acid, while in other examples, the M-PVA Magnetic Beads are tuned to attract ribonucleic acid.

In one example, a method for removing contaminants from a biological sample, for example to prepare the sample for PCR as described herein, is provided comprising the steps of providing a first well and a second well connected to each other via a micro channel, providing a fluid in the first well, the second well and the microchannel and placing the biological sample into the first well. The method further comprises the steps of introducing magnetic beads into the first well, drawing target molecules within the biological sample to the magnetic beads and introducing a magnet generating a magnetic field into the vicinity of the first well, the magnet field interacting with the magnetic beads. The method still further comprises the steps of moving the magnet toward the microchannel, the magnetic beads being drawn along with the movement of the magnet such that the magnetic beads and the target molecules are drawn into the microchannel and providing a gel in the microchannel where the gel interacts with the contaminates. The method is provided such that the gel interacts with the contaminates. The method finally comprises the step of moving the magnet toward the second well, the magnetic beads and target molecules being drawn along with the movement of the magnet such that the contaminates are separated from the target molecules as the contaminates are maintained within the gel and the magnetic beads and target molecules are drawn into the second well.

In another example, a system is provided for removing contaminants from a biological sample comprising a first well adapted to contain a fluid and receive the biological sample, a second well adapted to contain a fluid, a microchannel extending between the first well and the second well and a gel located within the microchannel. The purified biological sample may optionally be subjected to PCR according to the methods described herein. The system is provided such that magnetic beads are adapted to be introduced into the first well, the magnetic beads tuned to attract target molecules in the biological sample. The system further comprises a magnet adapted to be moved into the vicinity of the first well, the magnet adapted to generate a magnetic field to interact with the magnetic beads. The system is further provided such that the magnet is provided to be moved toward the microchannel wherein the magnetic beads are drawn along with the movement of the magnet and into the microchannel and the gel is adapted to interact with the contaminates such that at least some of the contaminates are captured within the gel when the magnetic beads move through the gel. Finally, the system is provided such that the magnet moves toward the second well and the magnetic beads and target molecules are drawn into the second well.

A system may be summarized as comprising: a horizontal actuator; a tray coupled to the horizontal actuator; a well plate coupled to the tray; a microfluidic chip coupled to the well plate; a vertical actuator; a pipette coupled to the vertical actuator; a heater or heating element mechanically and/or thermally coupled to the pipette to control a temperature of a fluid within the pipette; a pump coupled to the pipette to control movement of the fluid within the pipette;

and a controller communicatively coupled to the horizontal actuator to control horizontal movement of the tray, the well plate, and the microfluidic chip, communicatively coupled to the vertical actuator to control vertical movement of the pipette, communicatively coupled to the pump to control the pump, and communicatively coupled to the heater to control the heater.

The system may further comprise: a rotational actuator; and a magnet coupled to the rotational actuator; wherein the controller is communicatively coupled to the rotational actuator to control rotation of the magnet underneath the tray. The well plate may include a plurality of electrically conductive leads located underneath the microfluidic chip. The pipette may include a pipette tip held in a vertical orientation by a support arm and an end of the pipette opposite to the pipette tip may be held within a cartridge. The heater may include a stationary sidewall and a hinged sidewall rotatably coupled to the stationary sidewall by a hinge. The stationary sidewall may include a first groove and the hinged sidewall may include a second groove, the pipette may extend between the stationary sidewall and the hinged sidewall through the first and second grooves. The stationary sidewall may include a first bar movable outward from the stationary sidewall toward the hinged sidewall to pinch the pipette at a first location near a first side of the stationary sidewall and a second bar movable outward from the stationary sidewall toward the hinged sidewall to pinch the pipette at a second location near a second side of the stationary sidewall opposite to the first side of the stationary sidewall.

A method may be summarized as comprising: receiving a biological sample in a first well in a well plate; receiving another reagent in a second well in the well plate; operating a pump to draw the biological sample from the first well of the well plate into a pipette; operating an actuator to move the pipette from the first well of the well plate to a first well of a microfluidic chip; operating the pump to expel the biological sample from the pipette into the first well of the microfluidic chip; operating the actuator to move the pipette from the first well of the microfluidic chip to a second well of the microfluidic chip; operating the pump to draw the biological sample from the second well of the microfluidic chip into the pipette; operating the actuator to move the pipette from the second well of the microfluidic chip to the second well of the well plate; operating the pump to draw the other reagent from the second well of the well plate into the pipette; operating a heater to heat the biological sample and the other reagent within the pipette; operating the pump to expel the biological sample from the pipette into a third well in the well plate. The method optionally includes performing PCR after purification of sample as described herein.

The biological sample may include DNA, RNA, mRNA, or proteins. Contaminants may be removed from the biological sample in the microfluidic chip. The polymerase chain reaction may occur within the pipette.

DETAILED DESCRIPTION

Figure 1:
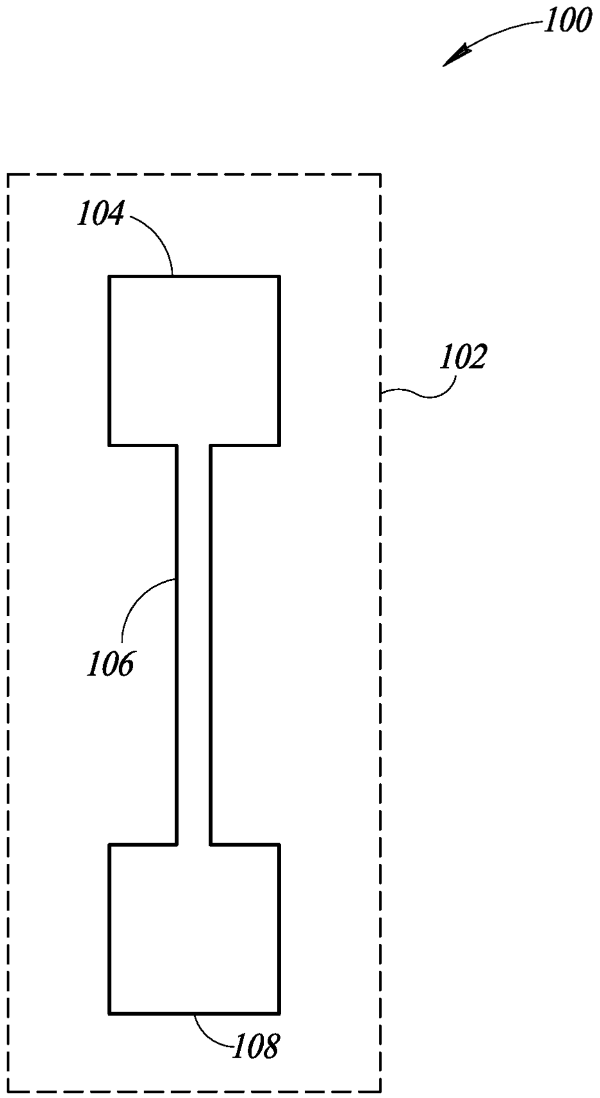
FIG. 1 is an illustration of one example of the present technology.

Referring now to the drawings, wherein like reference numerals designate corresponding structure throughout the views.

Embodiments of the present technology involve systems and methods for separating biological material from a sample via magnetic beads and electric fields. Embodiments of the technology are well suited for use with complex samples, such as blood, that comprise nucleic acid, generally in the form of deoxyribonucleic acid (DNA) and/or ribonucleic acid (RNA), which can be amplified via PCR as described herein below.

FIG. 1 illustrates a system 100 for Magneto electrophoretic separation to purify nucleic acids. This example utilizes a microfluidic chip 102, which includes a first well or reservoir 104, a microchannel 106 and a second well or reservoir 108. While the first and second wells 104, 108 are illustrated as square-shaped, it will be understood by those of skill in the art that they can comprise virtually any desired shape, such as, round or oval, etc.

In one example, the first well 104 may be provided having a diameter of approximately 2 mm. Additionally, in one example, the microchannel 106 may be approximately 2-3 cm in length, have a depth of approximately 100 μm, and be approximately 50-200 μm wide.

Figure 2:
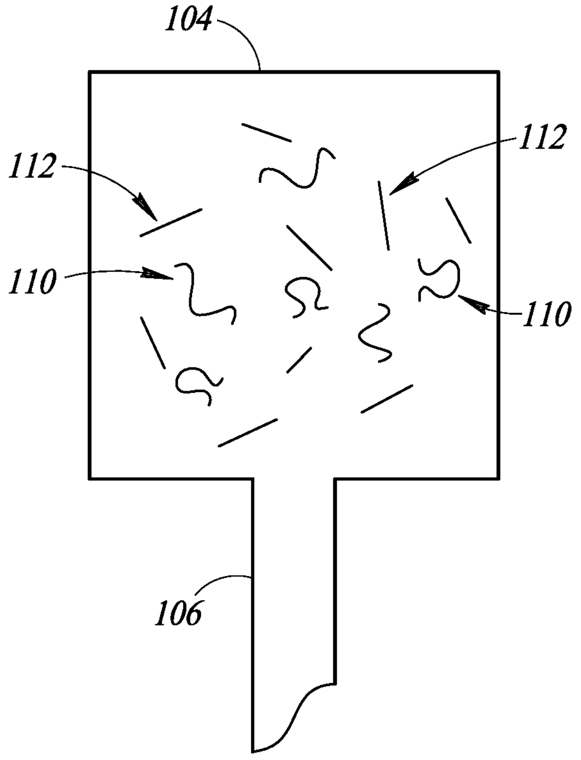
FIG. 2 is an enlarged view according to FIG. 1 including a biological sample to be purified.
Figure 3:
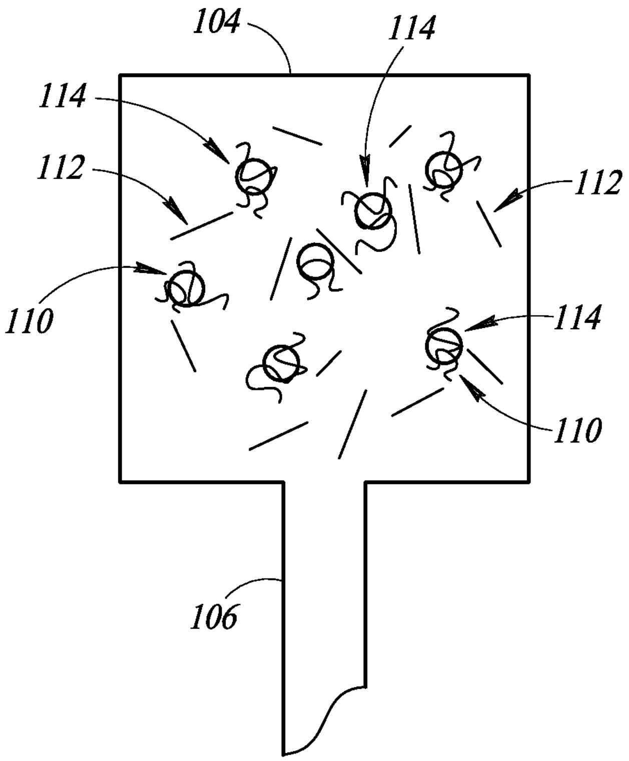
FIG. 3 is a view according to FIG. 2 with magnetic beads, which function to attract target molecules.

Turning now to FIGS. 2 and 3, first well 104 is illustrated with a biological sample therein comprising both target molecules 110 and contaminates 112. It will be noted that the biological sample may comprise blood and the first well 104 is provided with a fluid or buffer into which the biological sample is placed.

Magnetic beads 114, such as M-PVA Magnetic Beads (FIG. 3), are then introduced into the first well 104. The magnetic beads 114 are conjugated to collect target molecules, such as, nucleic acids from a complex sample like blood. As shown in FIG. 3, the target molecules 110 are drawn to the magnetic beads 114 while the contaminates 112 are not. This results in the target molecules 110 clustering around the individual magnetic beads 114 as illustrated.

In some examples, the biological sample can be gently magnetically stirred, for example, when the magnetic beads are placed into the biological sample to ensure mixing of the sample for proper adhesion of the target molecules. Likewise, it is contemplated that the biological sample can be heated locally.

Figure 4:
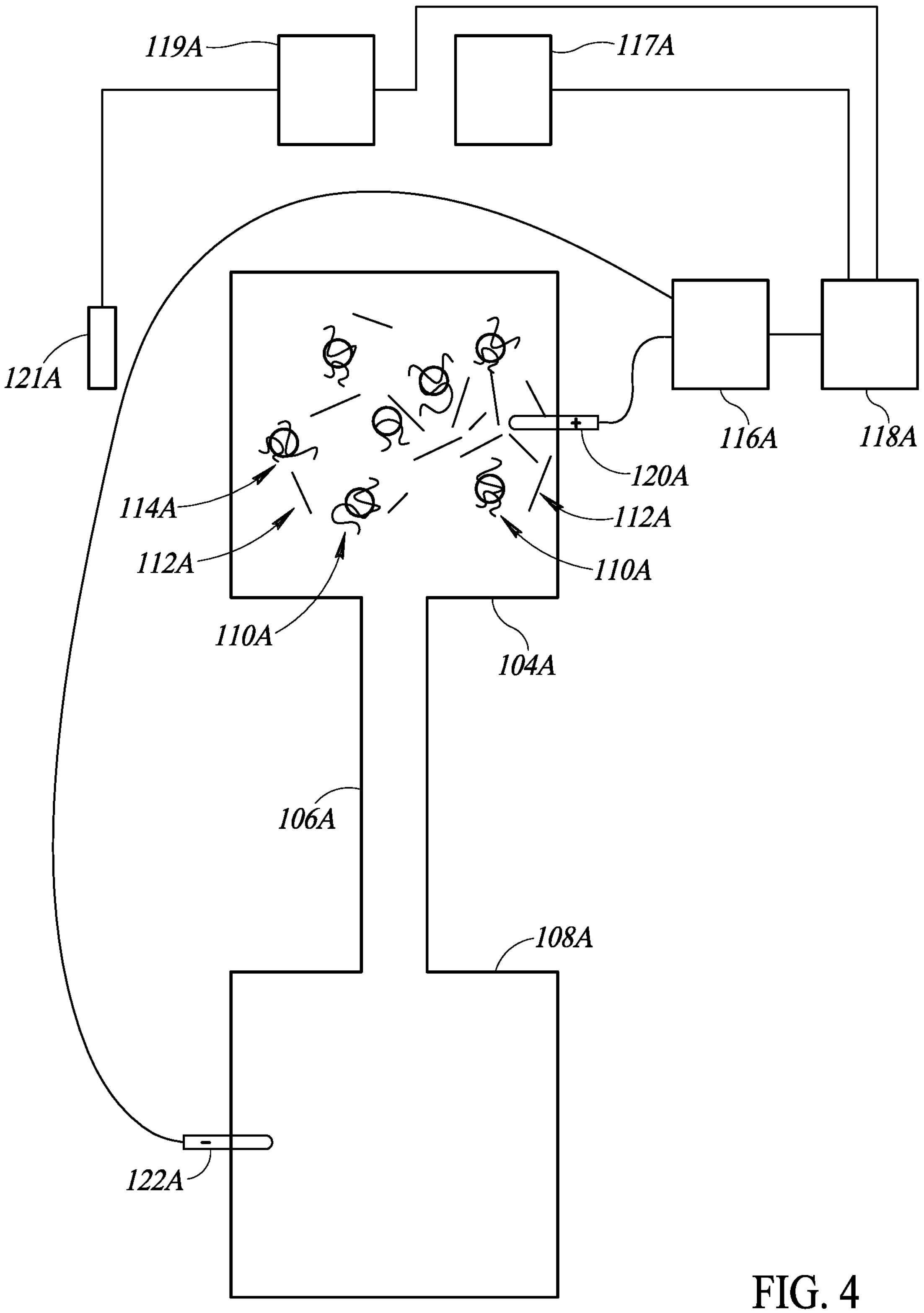
FIG. 4 is a view according to FIG. 3 with electrodes applying an electric field to the biological sample, which functions to attract contaminates.
Figure 5:
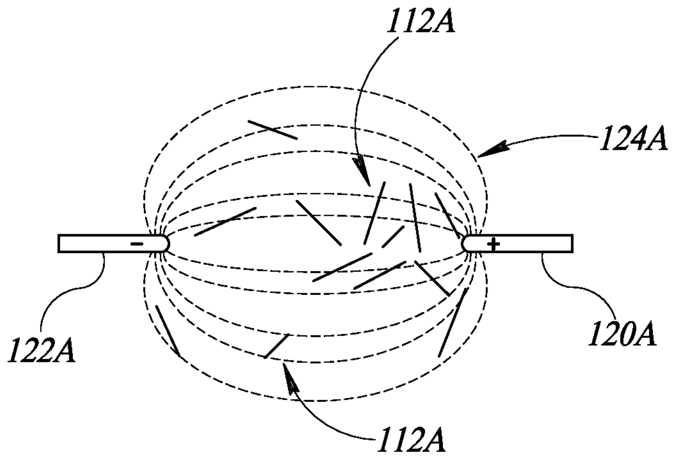
FIG. 5 is an illustration of the electric field that interacts with the contaminates.

FIGS. 4 and 5 illustrate an example of the system **100*a* that includes the use of a source of electrical energy 116*a* that is controlled by a controller 118*a*. The controller 118*a* may be any type of computer that is programmed to control the voltage source 116*a*** as desired.

It is contemplated that the controller **118*a* could also control a magnetic stirrer 117*a* and a heater 119*a*. The heater could comprise, for example, a resistive metal coating. The resistive metal coating could be Indium Tin Oxide (ITO) lining the well or reservoir. While the heater 119*a* is shown outside of the well, it will be understood that the coating could line the inside or outside of the well. Likewise, the controller 118*a* could provide direct control to the metal coating, or an intermediate controller could be provided that is adapted to apply a 0-12 volts signal to the heater. It should further be understood that a temperature sensor 121*a*** could be provided to give feedback information to maintain the temperature at a set point. While the various parts and components are illustrated with connecting lines to indicate a connection, it should be understood that these are only diagrammatic and the connections could comprise hard-wired connections or wireless connections.

Also included in FIG. 4 is a first probe 120*a* that is configured to have a positive charge and a second probe 122*a* that is configured to have a negative charge. The magnitude of the voltage differential developed between the first and second probe 120*a*, 122*a* is dependent on the source of electrical power.

As illustrated in FIG. 5, an electric field 124*a* is generated between the first and second probes 120*a*, 122*a*. The electric field is illustrated with forces lines (shown as dashed lines), which interact with the negatively charged contaminates 112*a*. The electric field 124*a* is generated to relatively strongly interact with the negatively charged contaminates 112*a*, but essentially does not interact with the magnetic beads 114*a* or the target molecules 110*a*.

Figure 6:
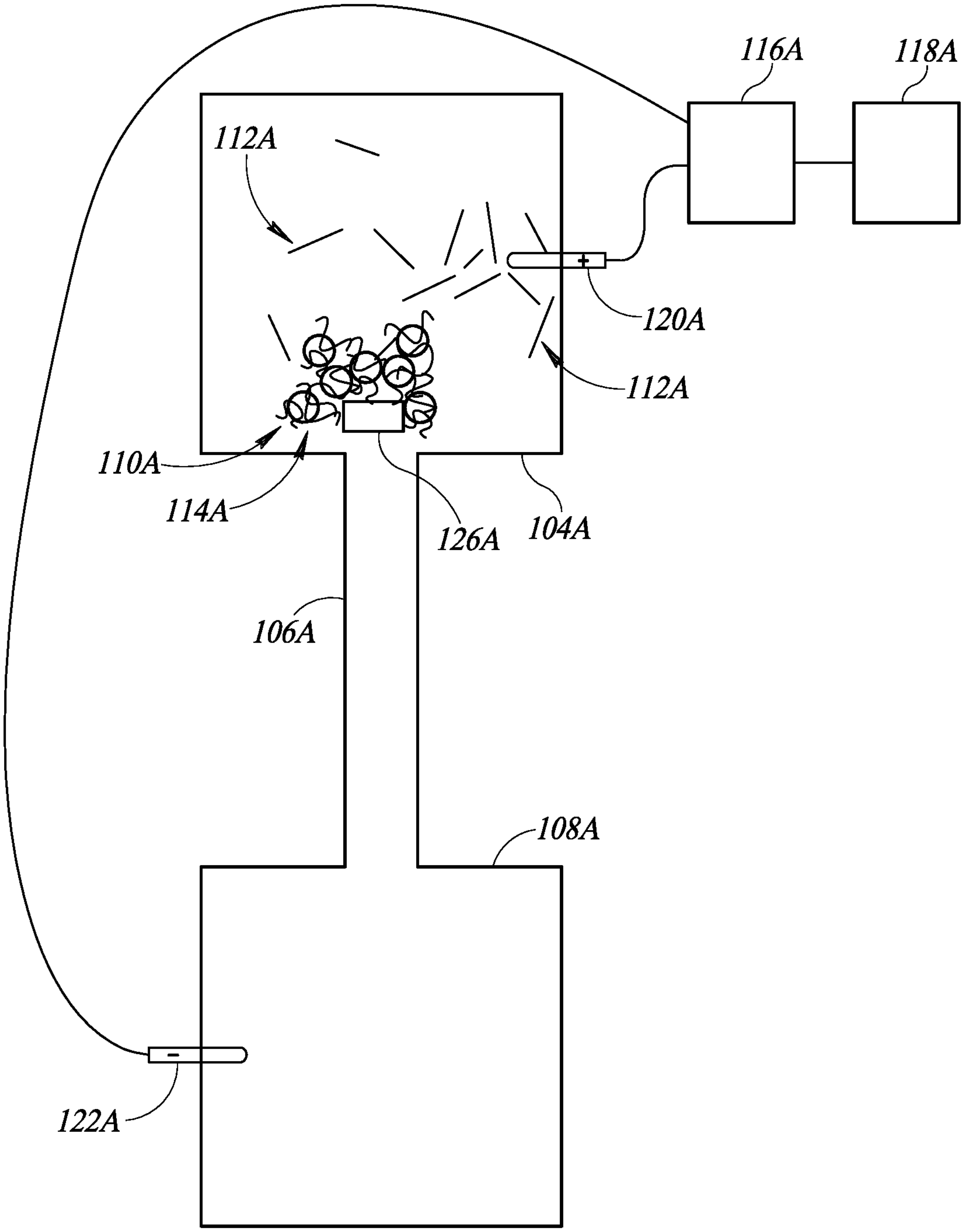
FIG. 6 is a view according to FIG. 4 with a magnet introduced into the vicinity of the magnetic beads that functions to attract the beads.

FIG. 6 illustrates the introduction of a magnet 126*a* that is introduced into the vicinity of the first well 104*a*. The magnet 126*a* is designed to attract the magnetic beads 114*a*. In one example the magnet 126*a* may be positioned at one end of the first well 104*a* and moved across the first well 104*a* toward the microchannel 106*a* such that the magnetic beads 114*a* and the associated target molecules 110*a* are moved toward the microchannel 106*a*. However, it will be understood by those of skill in the art that the electric field 124*a* will function to hold the negatively charged contaminates 112*a* in place due to the interaction with the electric field 124*a*.

As is illustrated in FIG. 6, the magnet 126*a* and the magnetic beads 114*a* are moved toward the microchannel 106*a*, but most of the contaminates 112*a* are left behind in the first well 104*a*. It is noted, however, that a small number of contaminates 112*a* might be pulled along with the target molecules 110*a* toward the microchannel.

It should further be noted that the movement of the magnet 126*a* may be controlled by controller 118*a* and may comprise fully automatic motion according to a software program. The movement could be simply linear, or any combination of complex movement that may be programmed.

Figure 7:
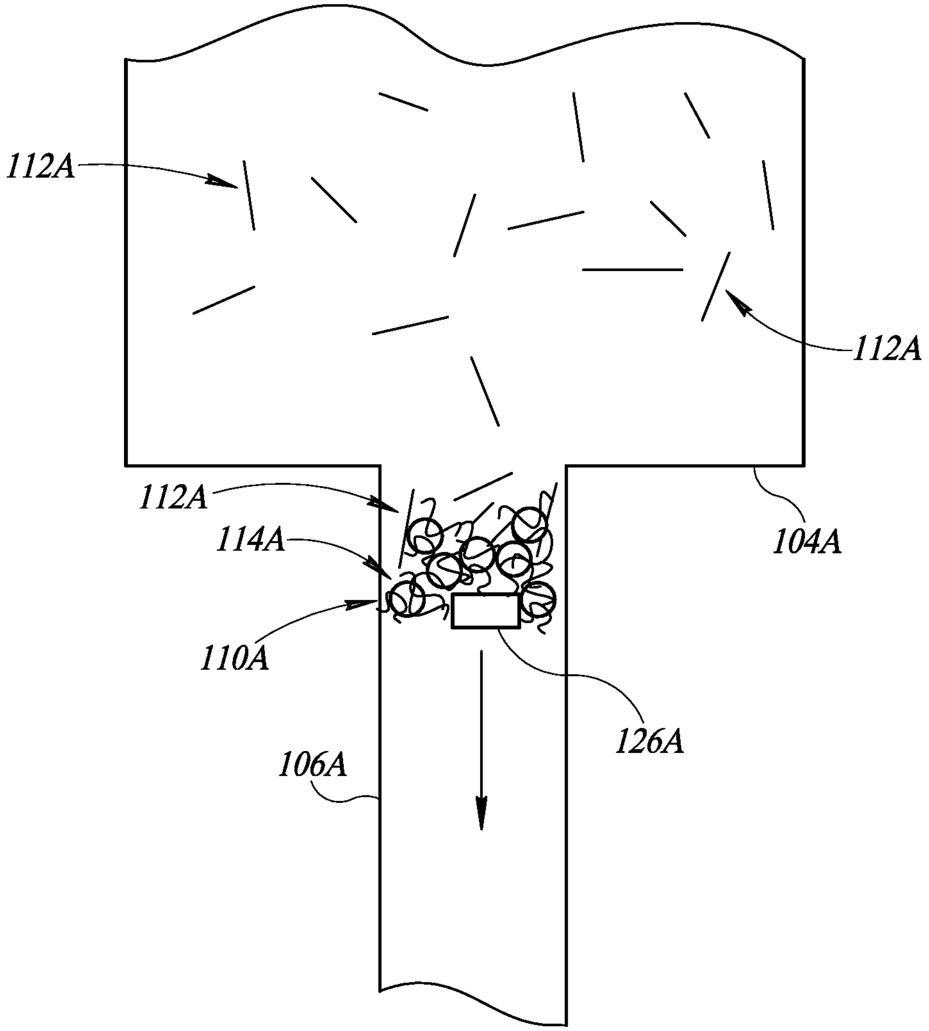
FIG. 7 is a view according to FIG. 6 where the magnetic beads are moved into the microchannel.
Figure 8:
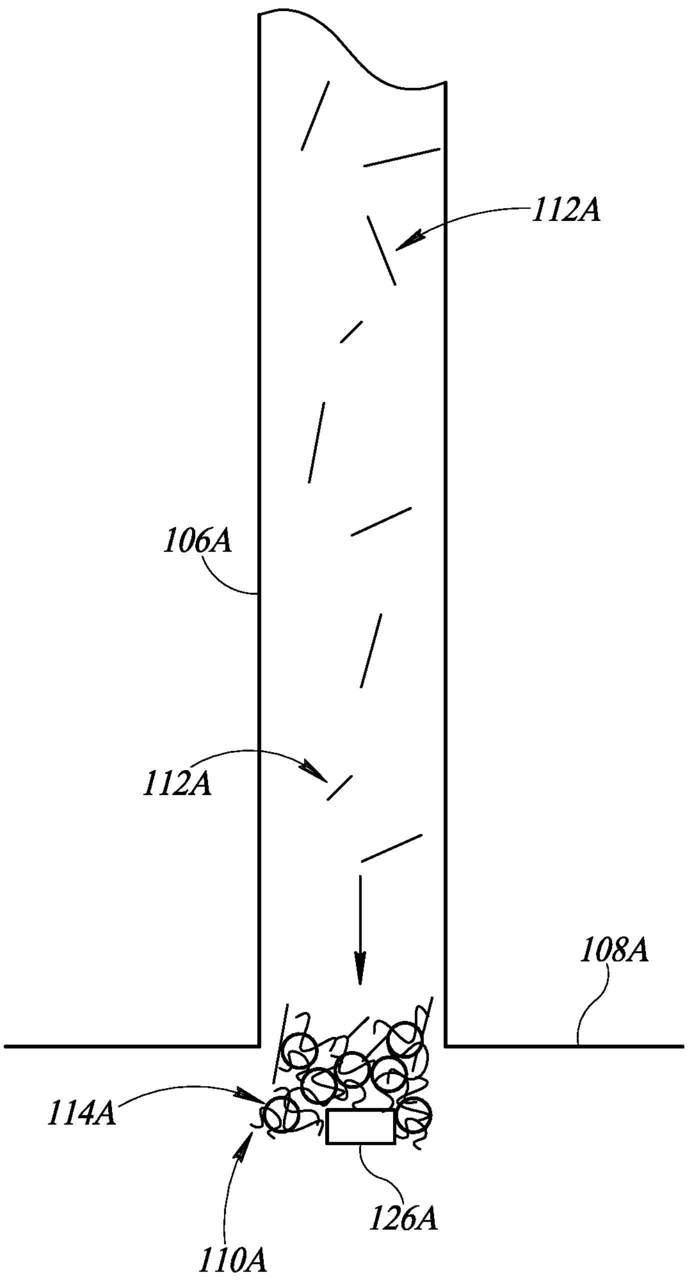
FIG. 8 is a view according to FIG. 7 where the magnetic beads are moved through the microchannel and into the second well.

FIG. 7 illustrates the magnet 126*a* moving into microchannel 106*a* with the magnetic beads 114*a* and target molecules 110*a* being pulled along. The microchannel 106*a* will be filled with a fluid (e.g., a buffer) such that the relatively rapid movement of the magnetic beads 114*a* through the fluid (e.g., on the order of millimeters/second) will result in any contaminates 112*a* that were pulled along with the target molecules 110*a* to be shed within the microchannel. This is illustrated in FIG. 8, which shows the magnet 126*a* moving through the opposites end of the microchannel and into the second well 108*a*.

At this point, any of the contaminates 112*a* that may have been pulled along with the target molecules 110*a* have been left behind in the fluid in the microchannel 106*a*.

Figure 9:
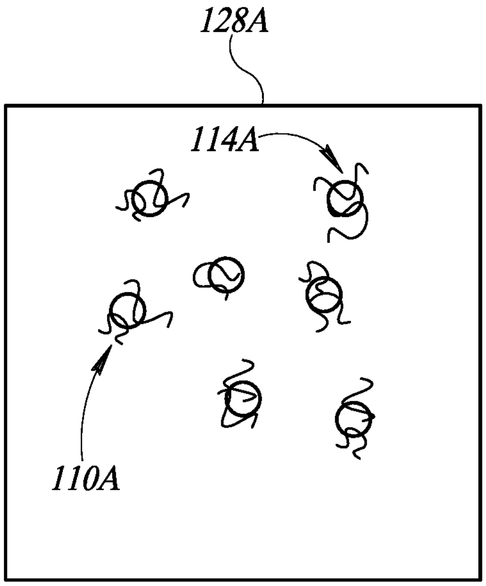
FIG. 9 is view of the purified biological sample according to FIG. 8.

The magnet 126*a* may then be moved into the second well 108*a* in any motion or series of movements as desired and programmed into the controller 118*a*. The magnetic beads 114*a* may then be removed from the fluid in the second well 108*a* and placed into a separate container 128*a* (FIG. 9). The magnetic beads 114*a* can then be de-tuned such that the target molecules 110*a* are no longer drawn toward the magnetic beads 114*a*, which can then be removed from the container 128*a*.

The result is a container 128*a* including a buffer solution and the target molecules 110*a* that are essentially free from contaminates 112*a*. The process is simply and easy to perform without the need for expensive or highly sophisticated equipment.

Figure 4A:
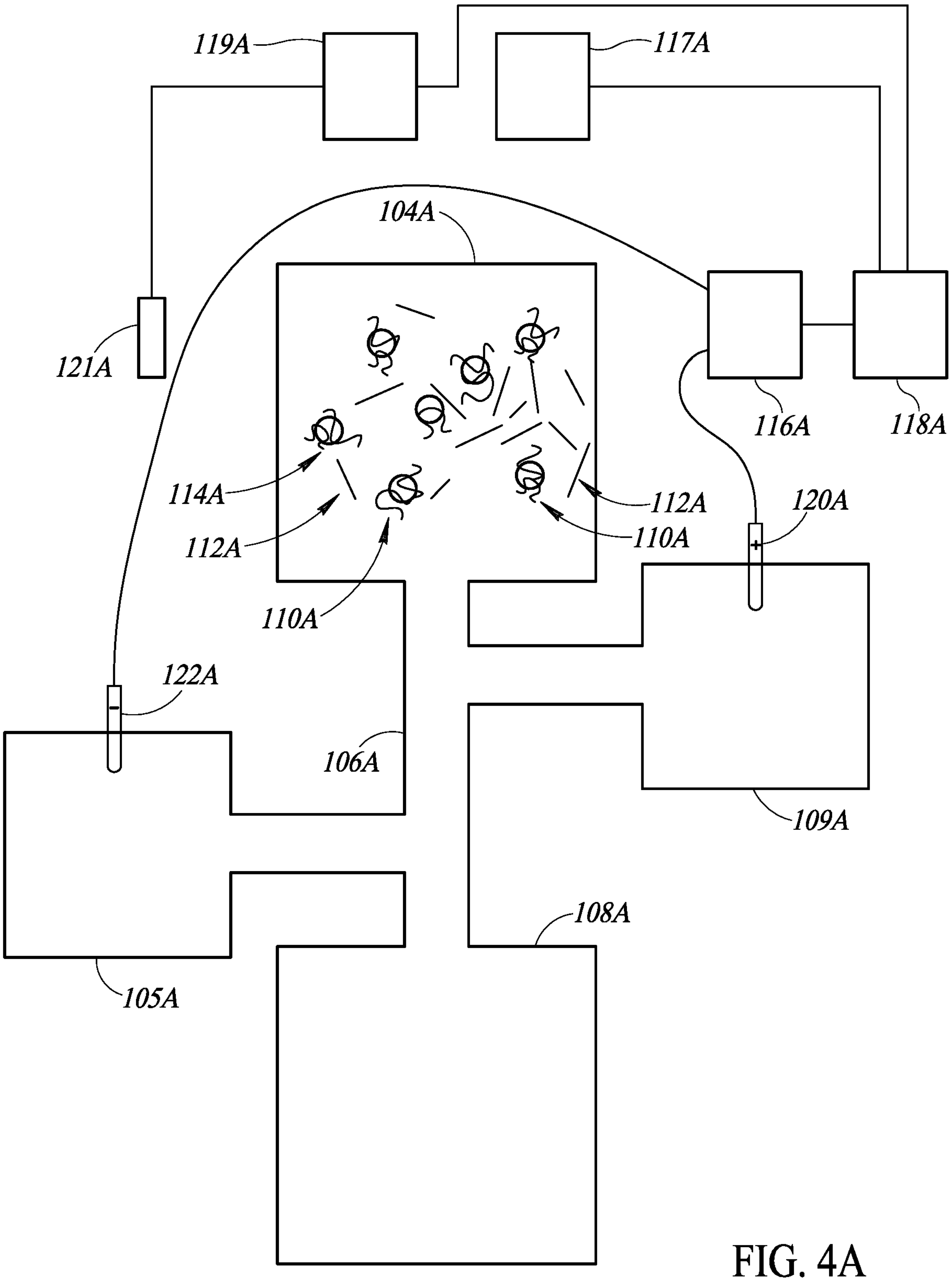
FIG. 4A is a view similar to that shown in FIG. 4, but wherein the electrodes are disposed in different wells than is shown in FIG. 4.

Referring now to FIG. 4A, the system shown therein is substantially similar to and operates in a similar fashion as does the system shown in FIG. 4, with the exception that rather than the first and second probes 120*a*, 122*a* being disposed in the first and second wells 104*a*, 108*a*, the first and second probes 120*a*, 122*a* are disposed in separate third and fourth wells 105*a*, 109*a*, which are also in communication with the microchannel 106*a*. With this configuration, the magnet 126*a* draws the material from the first well 104*a* to the second well 108*a* (as described above), and the presence of third and fourth wells 105*a*, 109*a* with the probes disposed therein 120*a*, 122*a* generate the electric field 124*a* across the microchannel 106*a* that the magnetic beads 114*a* traverse.

In this way, and in a manner similar to that discussed above, the microchannel 106*a* will be filled with a fluid (e.g., a buffer) such that the relatively rapid movement of the magnetic beads 114*a* through the fluid (e.g., on the order of millimeters/second) will result in any contaminates 112*a* that were pulled along with the target molecules 110*a* to be shed within the microchannel 106*a*. Thus, as with the previous example, the microchannel 106*a* provides for the relative motion of liquid via bead motion and an electric force via applied electric field to purify the samples.

Figure 10:
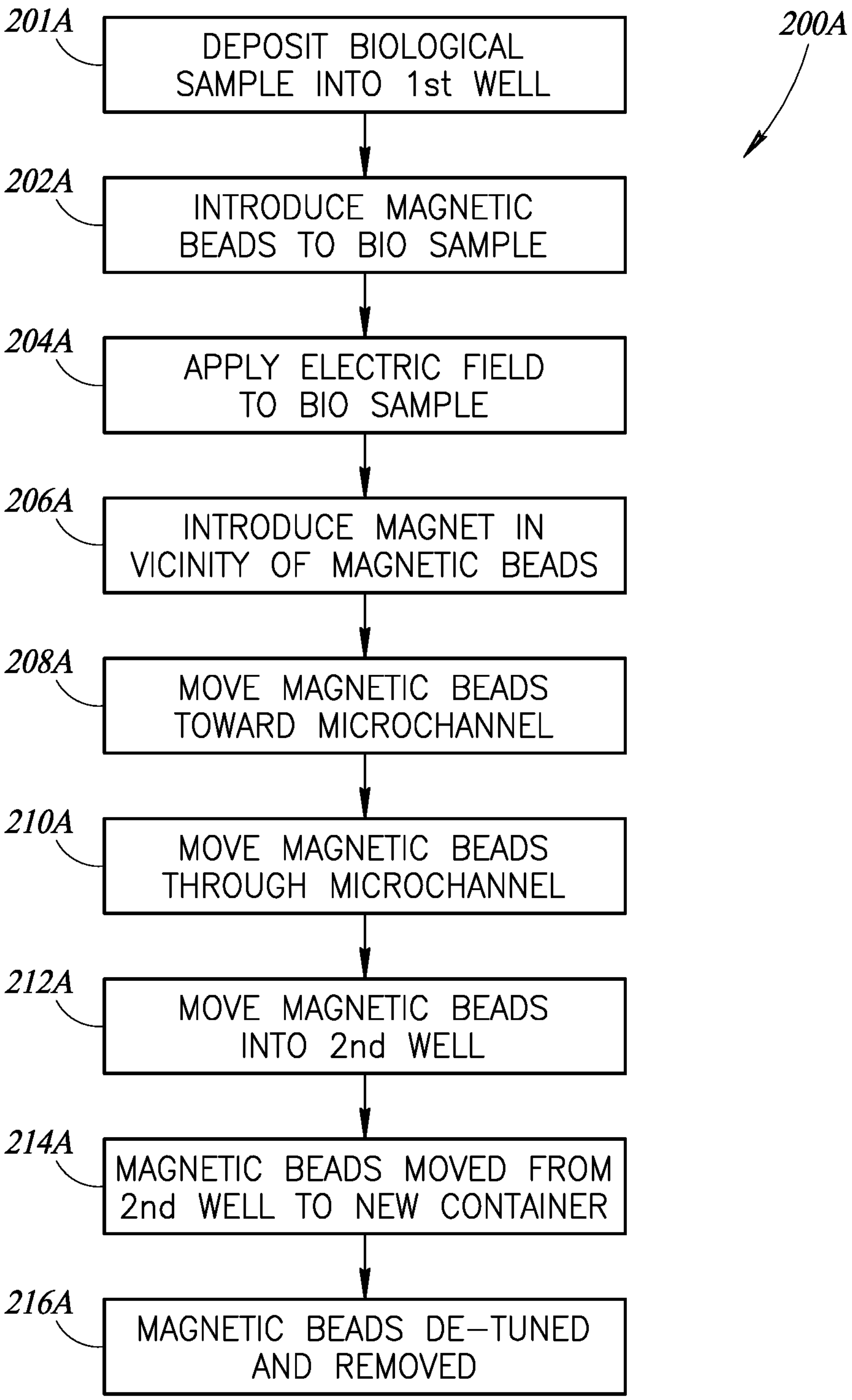
FIG. 10 is a flow diagram showing the sequence of operation of the technology according to FIGS. 1-8.

Turning now to FIG. 10, a flow diagram of the process 200*a* is provided. Initially, a biological sample to be purified is deposited into a well 201*a*, which may comprise a lab on a chip. Next, the magnetic beads are introduced into the biological sample 202*a* contained in the first well. As stated previously, in one example, the magnetic beads can be M-PVA Magnetic Beads that are tuned to attract target molecules. Still further, the target molecules can be nucleic acids. The magnetic beads are then maintained in the biological sample for a time period (an "incubation" period) to allow for attraction of the target molecules. In one example, the time period could be, for example, less than one minute.

The incubation period could further be supplemented with periodic mixing or stirring of the biological sample, which will further assist in the binding of target molecules. In one example, a magnetic stirrer can be used inside the wells/reservoirs for gentle mixing, in order to, for example, increase the bead/molecule interaction rate and thus reduce overall time for identical binding efficiency.

One of the benefits of these process steps is that the capture/binding of the target molecules occurs in the well/reservoir, so that the method uniquely processes a large amount of sample for rapid separation. Previously known methods must employ multiple washes per sample, whereas embodiments of the present method can remove bead-bound molecules from all superfluous molecules in one step on the timescale of single minutes. This allows for an increased throughput capacity.

Once the selected time period has elapsed, an electric field can be applied to the biological sample 204*a*. This can be accomplished by the application of leads coupled to a source of electrical power. It will be understood by those of skill in the art that the application of an electric field will also generate a magnetic field. The contaminates in the biological sample are negatively charged and will interact with the electric field, which functions to "hold" or maintain those contaminates within the electric field.

With the contaminates being held within the electric field, a magnet is then brought in proximity of the magnetic beads 206*a*. The magnet will function to attract the magnetic beads such that, as the magnet is moved in the vicinity of the first well, the magnetic beads will be drawn along with the movement of the magnet. The movement of the magnet may be fully automated and can move in a preprogrammed manner.

The magnet may then be moved so as to draw the magnetic beads toward a microchannel connected to the first well 208*a*. It will be understood that the electric field will be applied at this time such that, while the magnetic beads are moving toward the microchannel, contaminates are interacting with the electric field such that they are held in place within the fluid in the first well. This effectively allows the magnetic beads with the attracted target molecules to move away from the majority of contaminates.

The magnet then moves such that the magnetic beads are drawn into and move through the microchannel 210*a*. This can be done at a relatively fast rate, such as, for example, on the order of millimeters/second. Since there is a fluid (buffer) in the microchannel, the movement of the magnetic beads through the fluid will function to shed any unwanted contaminates that were inadvertently pulled along with the target molecules from the first well.

The magnet then continues to draw the magnetic beads into a second well 212*a* that is positioned at an opposite end of the microchannel. The result is a purified biological sample in which only the target molecules have been moved into the second well on the lab on a chip.

Another benefit to the above-described process is that it allows for high efficiency separation without requiring the use of any membrane or pumps. This is advantageous for resource limited settings.

From this point, the purified biological sample (e.g., the targeted nucleic acids) can then be removed from the second well and placed into a container 214*a*, after which the magnetic beads can be de-tuned such that the target molecules become unbound from the magnetic beads 216*a*. Finally, the magnetic beads can be removed from the container and discarded.

At this point, the purified target molecules are located in a separate container and are ready for downstream processes. It should be noted that the steps of removing the purified biological sample from the second well is optional. For example, the first well could be drained and the purified sample in the second well could be ready for amplification/detection on chip. Alternatively, the purified biological sample could be ready for amplification/detection off chip in the separate container.

Figure 11:
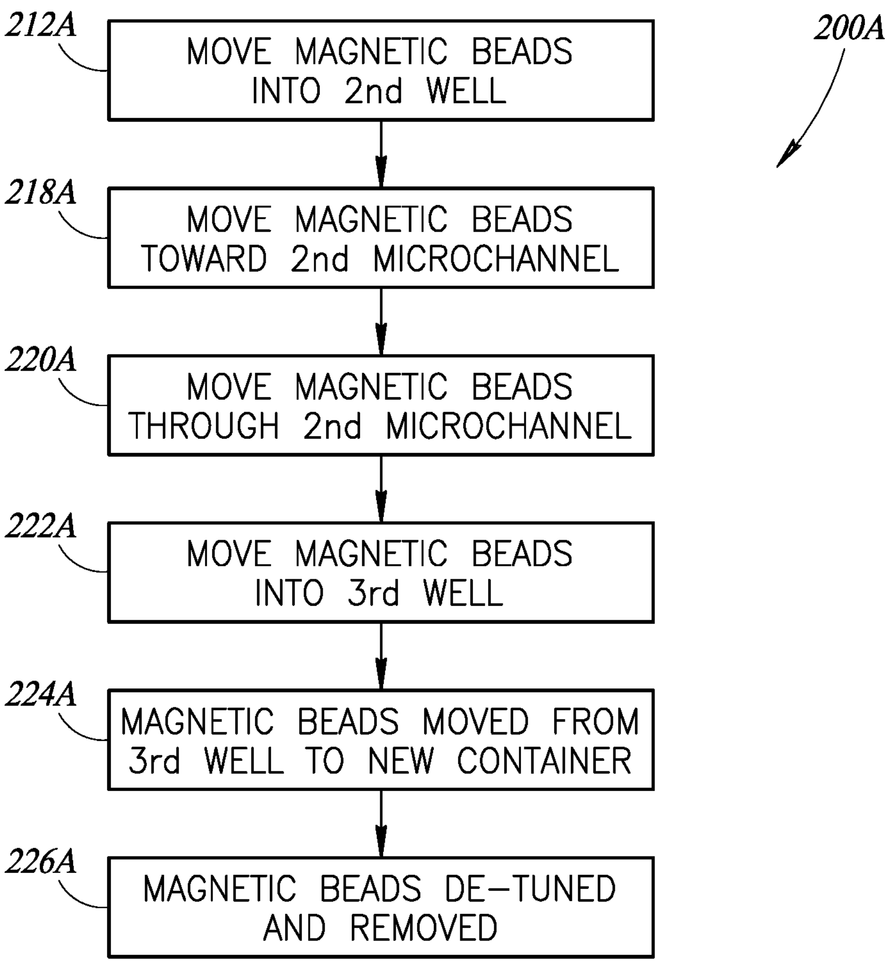
FIG. 11 is a flow diagram illustrating additional further steps according to FIG. 10.

FIG. 11 shows an alternate example that includes some additional process steps if enhanced purification is desired. For example, at step 212*a*, rather than removing the magnetic beads with the associated target molecules, it is contemplated that the system could comprise a second microchannel and a thirst well. In this example, the magnet is moved toward the second microchannel 218*a* and moved through the second microchannel 220*a*. This movement can be done relatively rapidly as was discussed in connection with the movement through the first microchannel. Likewise, the movement of the magnet can be fully automated where the magnet is moved according to a preprogrammed software program.

The magnetic beads can then be moved into a third well 222*a* positioned at an opposite end of the second microchannel where the magnetic beads can then be removed and placed into a new container 224*a*. As described previously, the magnetic beads can then be de-tuned and removed 226*a*.

In other examples, the fluid provided in the second well can be such that the volume creates a flow of fluid from the second well to the first well, which functions to carry any contaminates or unbound molecules into the first well. In examples that utilized a second microchannel and a third well, the fluid can be provided such that the volume provided in the third well creates a flow from the third well to the second well and from the second well to the first well. This flow of fluid, combined with the relatively rapid movement of the magnetic beads through the microchannel (s) functions to remove even more unbound molecules that may have inadvertently been drawn out of the first well.

In other examples, the method could further provide for local heating of the biological samples, in order, for example, to allow for thermal-driven processes, such as PCR (Polymerase chain reaction). This could be provided by applying 0-12 Volts to Indium Tin Oxide (ITO), which comprises a resistive metal coating. The heating could maintain temperatures locally for the sample without overheating other regions of the chip.

It should be noted that, while various functions and methods have been described and presented in a sequence of steps, the sequence has been provided merely as an illustration of one advantageous embodiment, and that it is not necessary to perform these functions in the specific order illustrated. It is further contemplated that any of these steps may be moved and/or combined relative to any of the other steps. In addition, it is still further contemplated that it may be advantageous, depending upon the application, to utilize all or any portion of the functions described herein.

Figure 12:
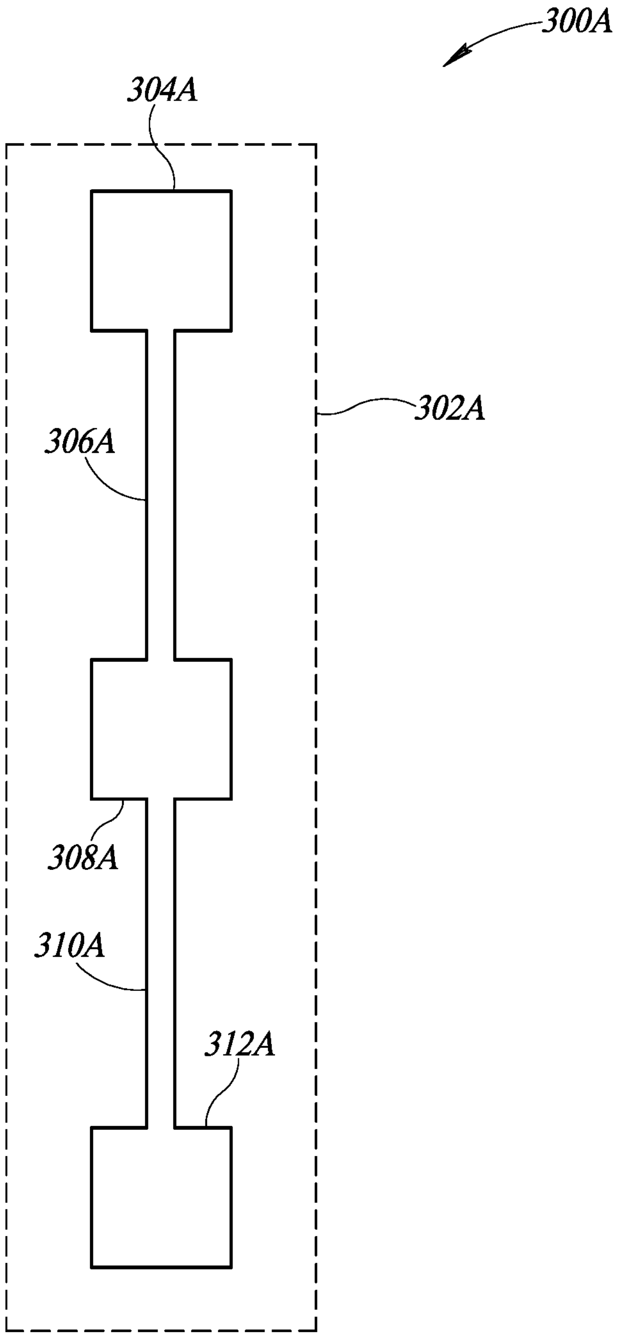
FIG. 12 is view according to FIG. 11.

Turning now to FIG. 12 an alternative example is illustrated for the lab on a chip for Magneto electrophoretic separation to purify nucleic acids. This example utilizes a microfluidic chip 302*a*, which includes a first well or reservoir 304*a*, a first microchannel 306*a* and a second well or reservoir 308*a*. The first microchannel 306*a* extends from the first well 304*a* to the second well 308*a*.

Additionally, this example utilizes a second microchannel 310*a* and a third well or reservoir 312*a*. The second microchannel 310*a* extends from the second well 308*a* to the third well 312*a*. As stated previously, while the first, second and third wells 304*a*, 308*a*, 312*a* are here illustrated as square-shaped, it will be understood by those of skill in the art that they can comprise virtually any desired shape, such as, round or oval, etc.

Polyethylene glycol (PEG), polyethylene oxide (PEO) or polyoxyethylene (POE) refer to an oligomer or polymer of ethylene oxide. The structure of PEG is commonly expressed as $H—(O—CH_2—CH_2)_n—OH$. PEG is a liquid and is referred to herein as a gel. Different forms of PEG are also available, depending on the initiator used for the polymerization process. One common initiator is a monofunctional methyl ether PEG, or methoxypoly (ethylene glycol), which is abbreviated m PEG. Lower-molecular-weight PEGs are also available as purer oligomers, referred to as monodisperse.

Figure 13:
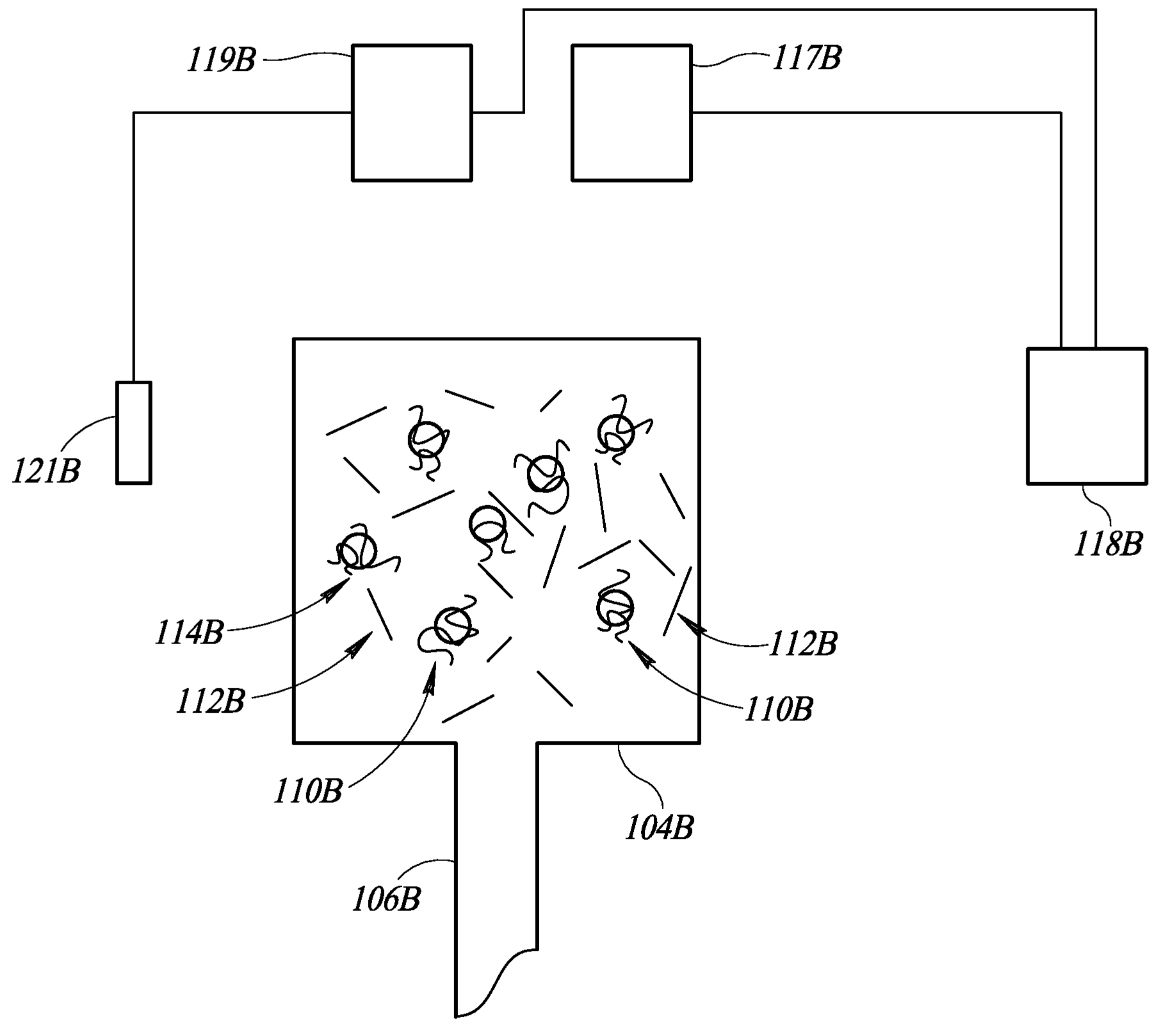
FIG. 13 is a view according to FIG. 3 with a controller, a stirrer, a heater and a temperature sensor.

FIG. 13 illustrates an example of the system 100*b* that includes a controller 118*b*. The controller 118*b* may be any type of computer that is programmed to control equipment used in connection with the microchip. It is contemplated that the controller 118*b* could control a magnetic stirrer 117*b* and a heater 119*b*. The heater could comprise, for example, a resistive metal coating. The resistive metal coating could be Indium Tin Oxide (ITO) lining the well or reservoir. While the heater 119*b* is shown outside of the well, it will be understood that the coating could line the inside or outside of the well. Likewise, the controller 118*b* could provide direct control to the metal coating, or an intermediate controller could be provided that is adapted to apply a 0-12 volts signal to the heater. It should further be understood that a temperature sensor 121*b* could be provided to give feedback information to maintain the temperature at a set point. While the various parts and components are illustrated with connecting lines to indicate a connection, it should be understood that these are only diagrammatic and the connections could comprise hard-wired connections or wireless connections.

Figure 14:
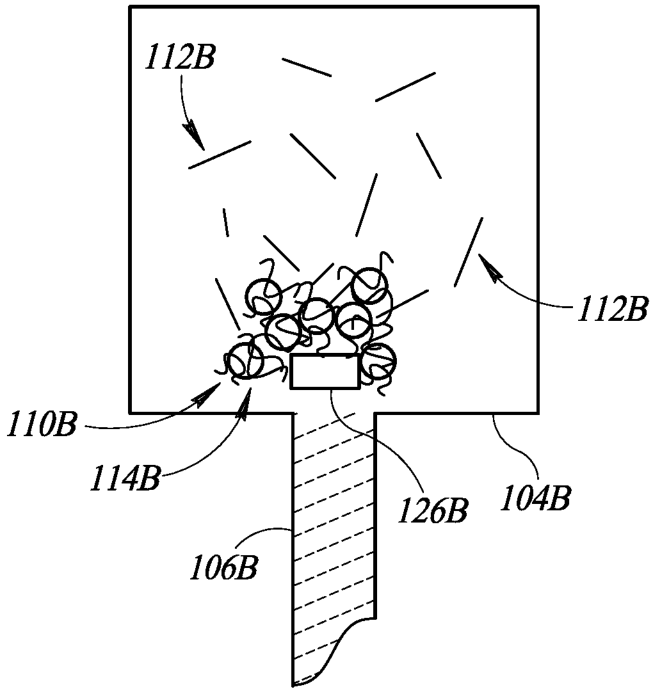
FIG. 14 is a view according to FIG. 13 with a magnet introduced into the vicinity of the magnetic beads that functions to attract the beads.

FIG. 14 illustrates the introduction of a magnet 126*b* that is introduced into the vicinity of the first well 104*b*. The magnet 126*b* is designed to attract the magnetic beads 114*b*. In one example the magnet 126*b* may be positioned at one end of the first well 104*b* and moved across the first well 104*b* toward the microchannel 106*b* such that the magnetic beads 114*b* and the associated target molecules 110*b* are moved toward the microchannel 106*b*.

The magnet 126*b* and the magnetic beads 114*b* are moved toward the microchannel 106*b* leaving some of the contaminates 112*b* behind in the first well 104*b*. It is noted, however, that a number of contaminates 112*b* may be pulled along with the target molecules 110*b* toward the microchannel.

It should further be noted that the movement of the magnet 126*b* may be controlled by controller 118*b* and may comprise fully automatic motion according to a software program. The movement could be simply linear, or any combination of complex movement that may be programmed.

Figure 15:
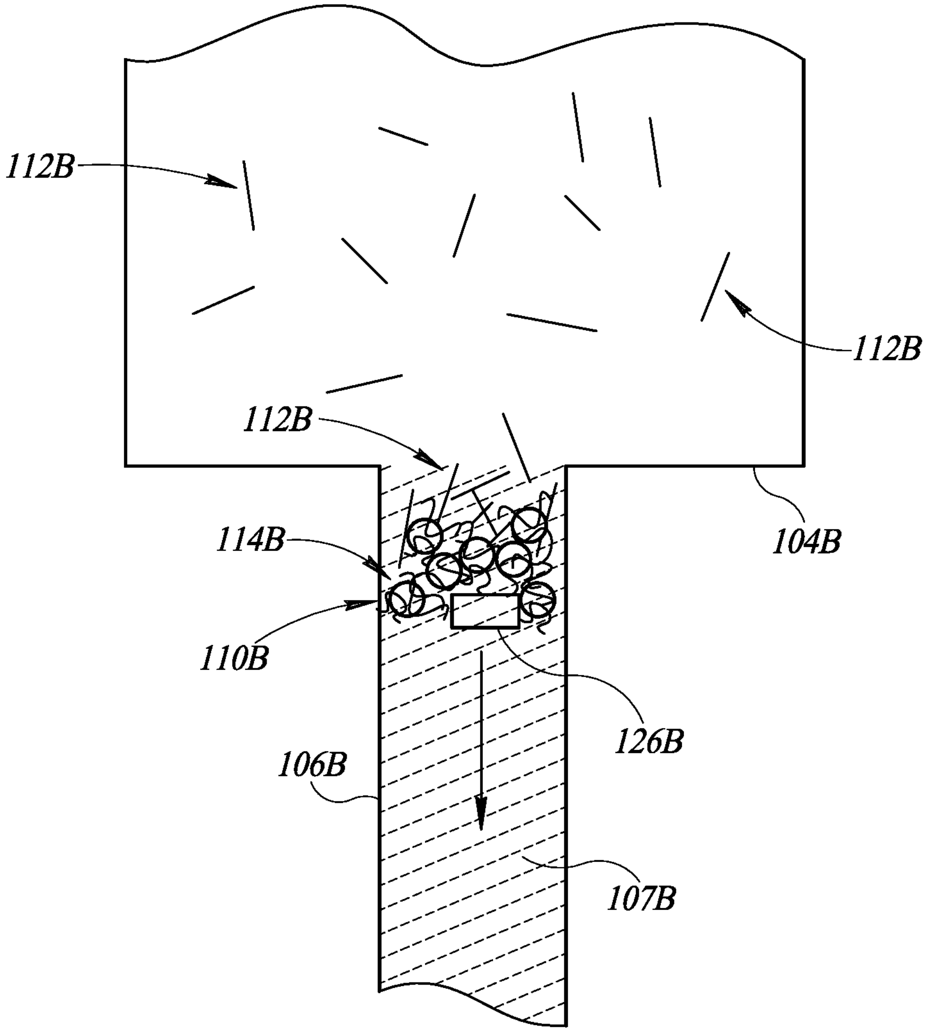
FIG. 15 is a view according to FIG. 14 where the magnetic beads are moved into the microchannel.

FIG. 15 illustrates the magnet 126*b* moving into microchannel 106*b* with the magnetic beads 114*b* and target molecules 110*b* being pulled along. The microchannel 106*b* will be filled with a gel 107*b* (e.g., PEG), which is illustrated as a dashed line in microchannel 106*b*. The negatively charged contaminates 112*b* interact with the gel 107*b* such that the contaminates 112*b* are held in place within the gel 107*b* as the magnetic beads 114*b* and target molecules 110*b* advance through the microchannel 106*b*.

Figure 16:
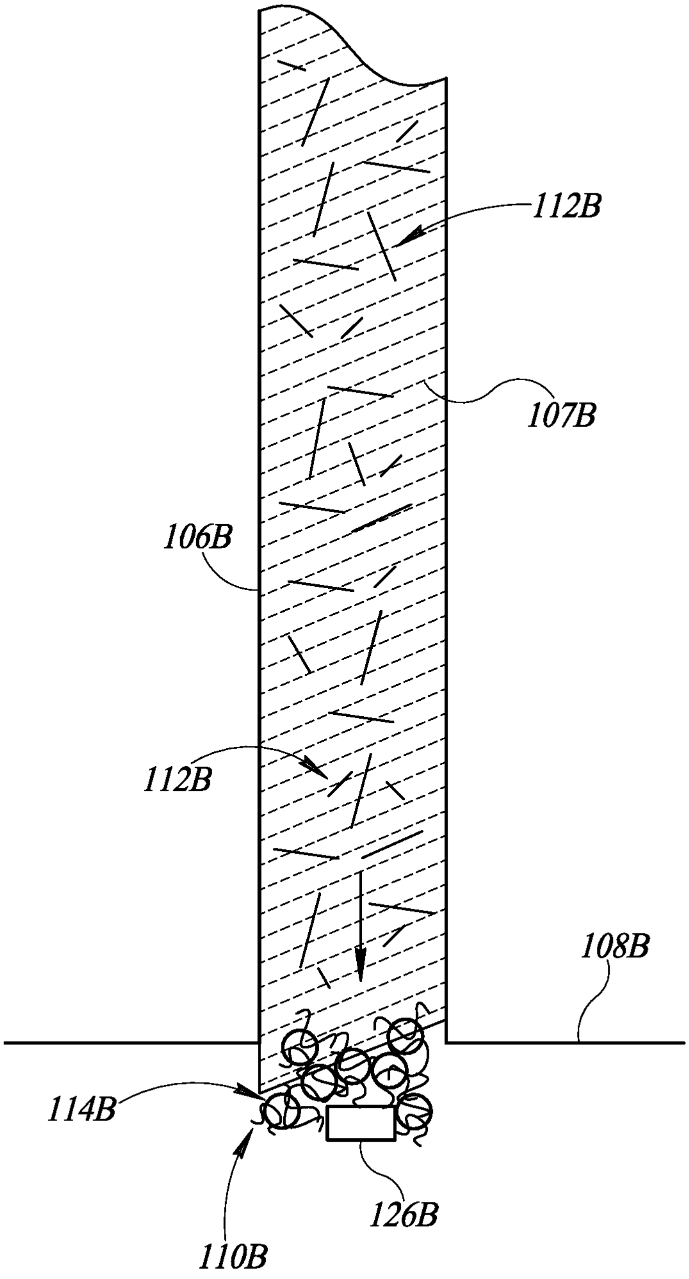
FIG. 16 is a view according to FIG. 15 where the magnetic beads are moved through the microchannel and into the second well.

In one example, the movement of the magnetic beads 114*b* through the gel 107*b* is relatively rapid (e.g., one the order of millimeters/second), which results in any contaminates 112*b* that were pulled along with the target molecules 110*b* to be shed within the gel 107*b* within the microchannel 106*b*. This is illustrated in FIG. 16, which shows the magnet 126*b* moving through the opposite end of the microchannel and into the second well 108*b*.

At this point, at least a significant portion of the contaminates 112*b* that were pulled along with the target molecules 110*b* have been left behind in the gel 107*b* in the microchannel 106*b*.

Figure 17:
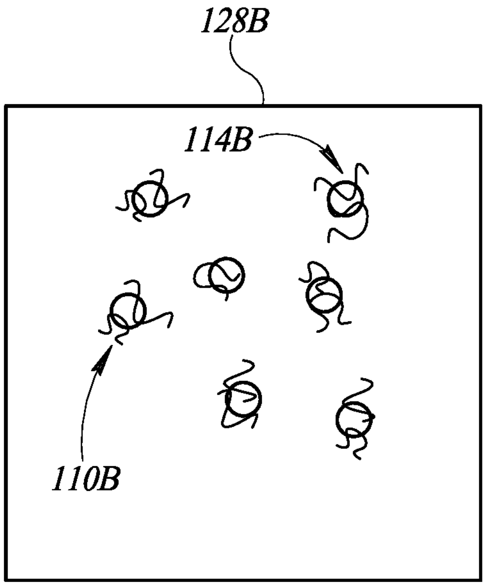
FIG. 17 is view of the purified biological sample according to FIG. 16.

The magnet 126*b* may then be moved into the second well 108*b* in any motion or series of movements as desired and programmed into the controller 118*b*. The magnetic beads 114*b* may then be removed from the fluid in the second well 108*b* and placed into a separate container 128*b* (FIG. 17). The magnetic beads 114*b* can then be de-tuned such that the target molecules 110*b* are no longer drawn toward the magnetic beads 114*b*, which can then be removed from the container 128*b*.

The result is a container 128*b* including a buffer solution and the target molecules 110*b* that are essentially free from contaminates 112*b*. The process is simply and easy to perform without the need for expensive or highly sophisticated equipment.

Figure 18:
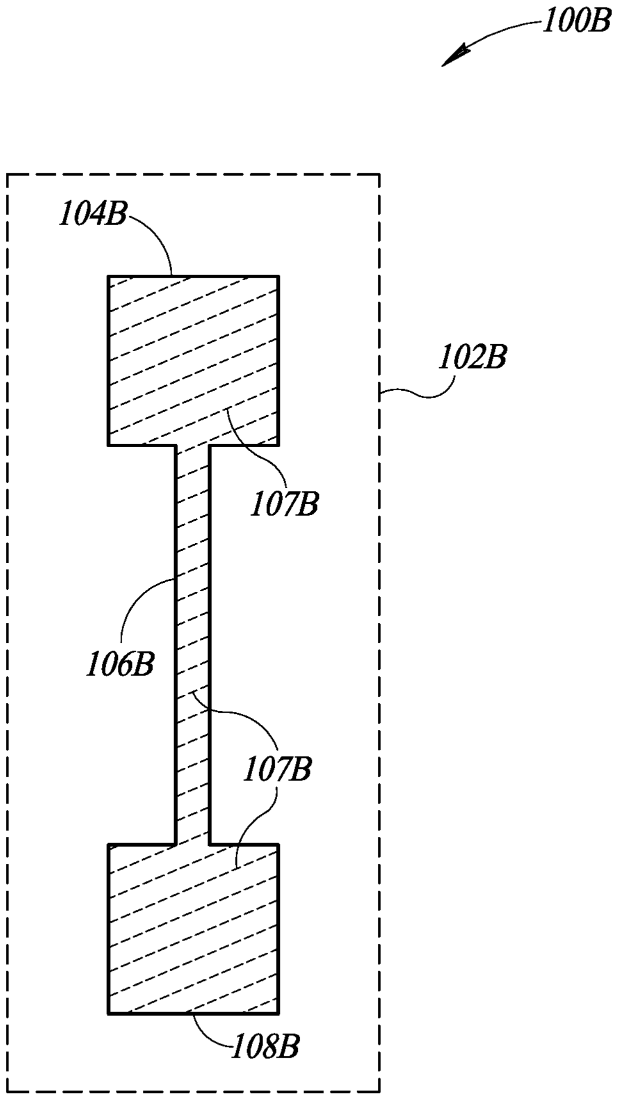
FIG. 18 is an illustration of one example of the present technology according to FIG. 1.

FIG. 18 illustrates the first well 104*b*, the microchannel 106*b* and the second well 108*b* all including the gel 107*b*. It should be noted that the gel 107*b* could be placed only in the microchannel. Alternatively, the gel 107*b* could be placed in both the microchannel 106*b* and the first well 104*b*. The idea is that the negatively charged contaminates 112*b* will interact with the gel 107*b* such that the contaminates will become held by the gel 107*b* allowing the magnetic beads 114*b* along with the target molecules 110*b* to be moved away from and separated from the contaminates 112*b*.

Figure 19:
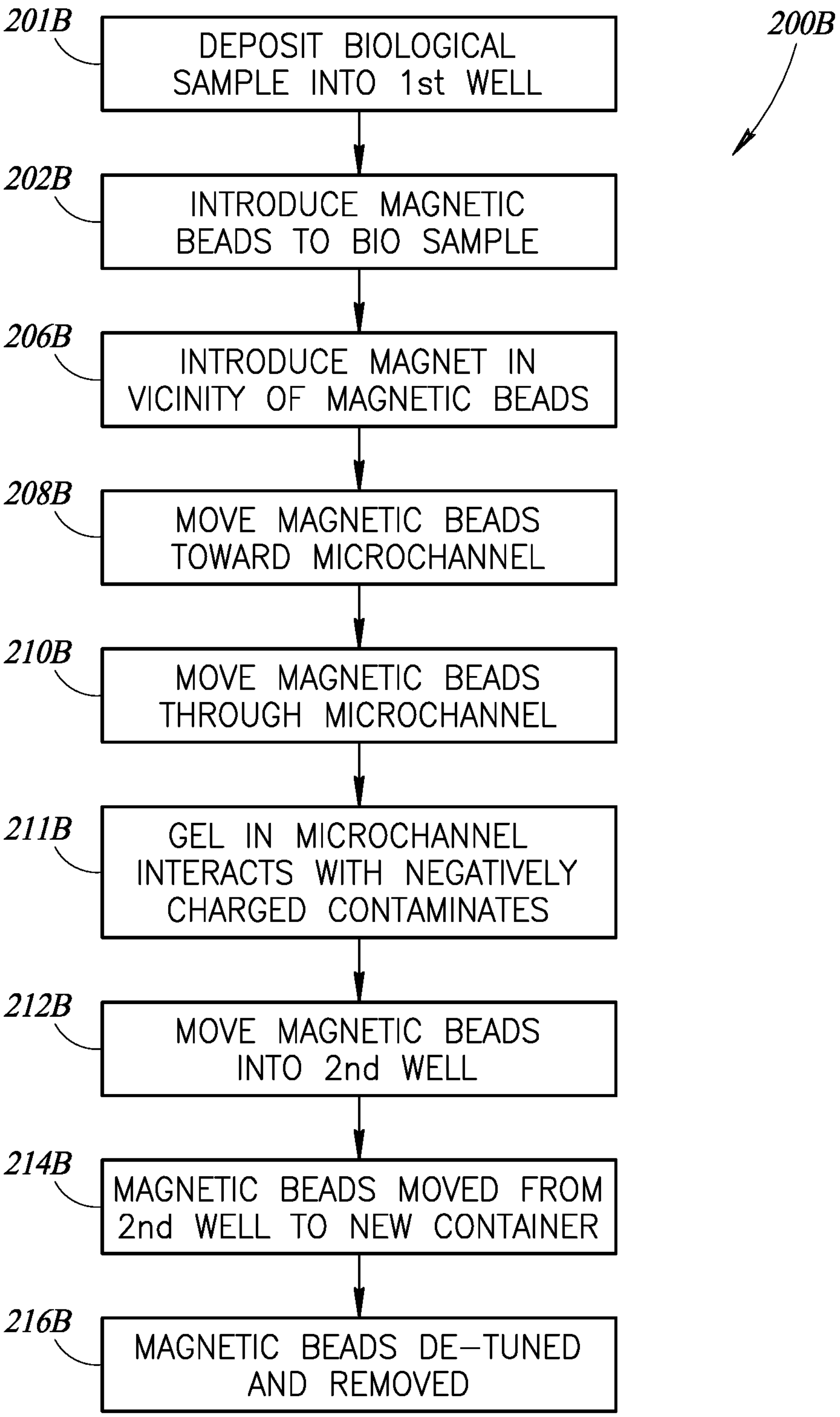
FIG. 19 is a flow diagram showing the sequence of operation of the technology according to FIGS. 1-3 and 13-17.

Turning now to FIG. 19, a flow diagram of the process 200*b* is provided. Initially, a biological sample to be purified is deposited into a well 201*b*, which may comprise a lab on a chip. Next, the magnetic beads are introduced into the biological sample 202*b* contained in the first well. As stated previously, in one example, the magnetic beads can be M-PVA Magnetic Beads that are tuned to attract target molecules. Still further, the target molecules can be nucleic acids. The magnetic beads are then maintained in the biological sample for a time period (an "incubation" period) to allow for attraction of the target molecules. In one example, the time period could be less than one minute.

The incubation period could further be supplemented with periodic mixing or stirring of the biological sample, which will further assist in the binding of target molecules. In one example, a magnetic stirrer can be used inside the wells/reservoirs for gentle mixing.

One of the benefits of these process steps is that the capture/binding of the target molecules occurs in the well/reservoir, so that the method uniquely processes a large amount of sample for rapid separation.

The next step is to place a magnet in proximity to the magnetic beads 206*b*. The magnet will function to attract the magnetic beads such that, as the magnet is moved in the vicinity of the first well, the magnetic beads will be drawn along with the movement of the magnet. The movement of the magnet may be fully automated and can move in a preprogrammed manner.

The magnet may then be moved so as to draw the magnetic beads toward a microchannel connected to the first well 208*b*. The magnet moves such that the magnetic beads are drawn into the microchannel 210*b*. It will be understood that the microchannel is filled with a gel, such as PEG, which will function to interact with negatively charged contaminates 211*b*. This interaction means that, as the magnet pulls the magnetic beads along the microchannel and therefore, through the gel, the negatively charged contaminates are shed within the gel in the microchannel. This functions to purify the sample as it moves through the microchannel.

It is further contemplated that the movement of the magnetic beads through the microchannel can be done at a relatively fast rate, such as, for example, on the order of millimeters/second. The movement of the magnetic beads through the gel will function to shed the unwanted contaminates not only due to the PEG interacting with the negatively charged contaminates, but also due to fluid resistance helping to shed contaminates that were pulled along with the target molecules from the first well.

The magnet then continues to draw the magnetic beads into a second well 212*b* that is positioned at an opposite end of the microchannel. The result is a purified biological sample in which only the target molecules have been moved into the second well on the lab on a chip.

Another benefit to the above-described process is that it allows for high efficiency separation without requiring the use any membrane or pumps. This is advantageous for resource limited settings.

From this point, the purified biological sample (e.g., the targeted nucleic acids) can then be removed from the second well and placed into a container 214*b*, after which the magnetic beads can be de-tuned such that the target molecules become unbound from the magnetic beads 216*b*. Finally, the magnetic beads can be removed from the container and discarded.

At this point, the purified target molecules are located in a separate container and are ready for downstream processes. It should be noted that the steps of removing the purified biological sample from the second well is optional. For example, the first well could be drained and the purified sample in the second well could be ready for amplification/detection on chip. Alternatively, the purified biological sample could be ready for amplification/detection off chip in the separate container.

Figure 20:
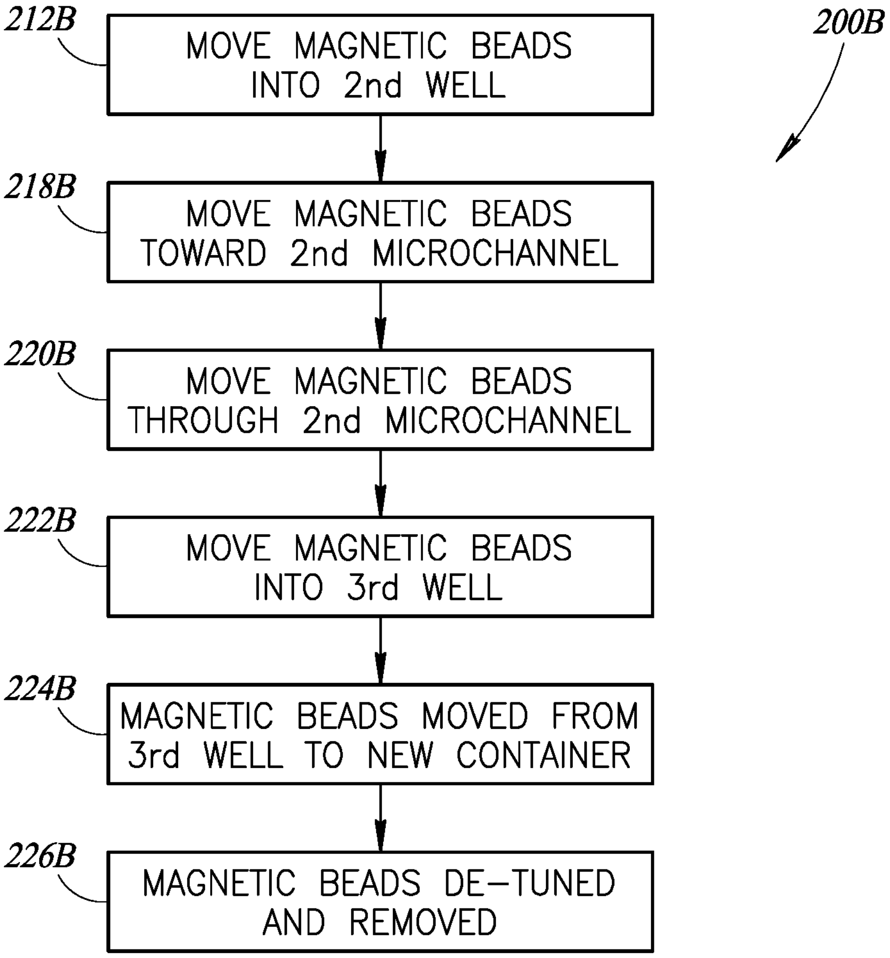
FIG. 20 is a flow diagram illustrating additional further steps according to FIG. 19.

FIG. 20 optional additional process steps if enhanced purification is desired. For example, at step 212*b*, rather than removing the magnetic beads with the associated target molecules, it is contemplated that the system could comprise a second microchannel and a third well. In this example, the magnet is moved toward the second microchannel 218*b* and moved through the second microchannel 220*b*. This movement can be done relatively rapidly as was discussed in connection with the movement through the first microchannel. Likewise, the movement of the magnet can be fully automated where the magnet is moved according to a preprogrammed software program.

The magnetic beads can then be moved into a third well 222*b* positioned at an opposite end of the second microchannel where the magnetic beads can then be removed and placed into a new container 224*b*. As described previously, the magnetic beads can then be de-tuned and removed 226*b*.

In other examples, the fluid provided in the second well could comprise a gel as illustrated in connection with FIG. 18. In one example, the gel can be provided such that the volume creates a flow of gel from the second well to the first well, which further functions to carry any contaminates or unbound molecules into the first well. In examples that utilize a second microchannel and a third well (FIG. 21), the gel can be provided such that the volume provided in the third well creates a flow from the third well to the second well and from the second well to the first well. This flow of gel, combined with the direct interaction of the contaminates with the gel and the relatively rapid movement of the magnetic beads through the microchannel(s) functions to remove even more unbound molecules that may have been drawn out of the first well.

In other examples, the method could further provide for local heating of the biological samples. This could be provided, for example, by applying 0-12 Volts to Indium Tin Oxide (ITO), which comprises a resistive metal coating. The heating could maintain temperatures locally for the sample without overheating other regions of the chip.

It should be noted that, while various functions and methods have been described and presented in a sequence of steps, the sequence has been provided merely as an illustration of one advantageous embodiment, and that it is not necessary to perform these functions in the specific order illustrated. It is further contemplated that any of these steps may be moved and/or combined relative to any of the other steps. In addition, it is still further contemplated that it may be advantageous, depending upon the application, to utilize all or any portion of the functions described herein.

Figure 21:
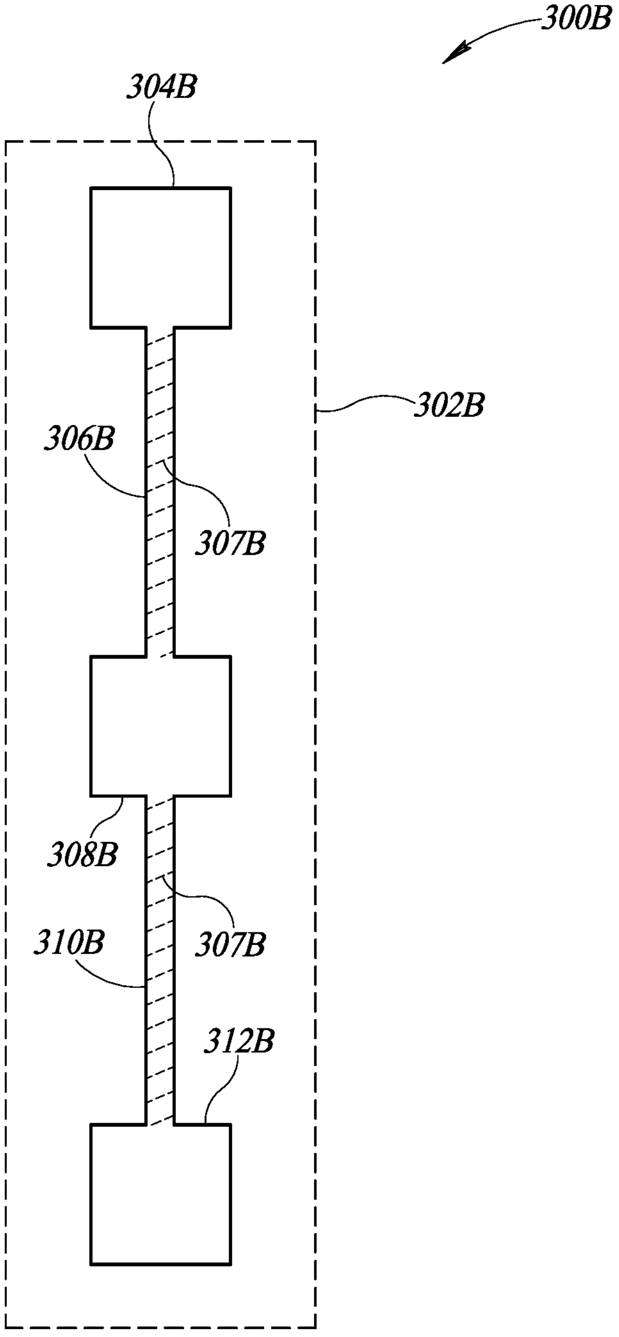
FIG. 21 is a view of a chip employing a method according to FIG. 20.

Referring now to FIG. 21 an example is illustrated for the lab on a chip for purification of nucleic acids employing a further optional enhanced purification process according to FIG. 20. This example utilizes a microfluidic chip 302*b*, which includes a first well or reservoir 304*b*, a first microchannel 306*b* and a second well or reservoir 308*b*. The first microchannel 306*b* extends from the first well 304*b* to the second well 308*b*.

Additionally, this example utilizes a second microchannel 310*b* and a third well or reservoir 312*b*. The second microchannel 310*b* extends from the second well 308*b* to the third well 312*b*. As stated previously, while the first, second and third wells 304*b*, 308*b*, 312*b* are here illustrated as square-shaped, it will be understood by those of skill in the art that they can comprise virtually any desired shape, such as, round or oval, etc.

A gel 307*b* is provided at a minimum in the first microchannel 306*b*. However, the gel 307*b* is also illustrated as optionally being in the second microchannel 310*b*. It should further be understood that the gel could be provided in any of the first, second or third wells 304*b*, 308*b*, 312*b* as desired. Likewise, the volume of gel 307*b* and placement can be selected to create a flow rate toward the first well 304*b* as desired.

Figure 22:
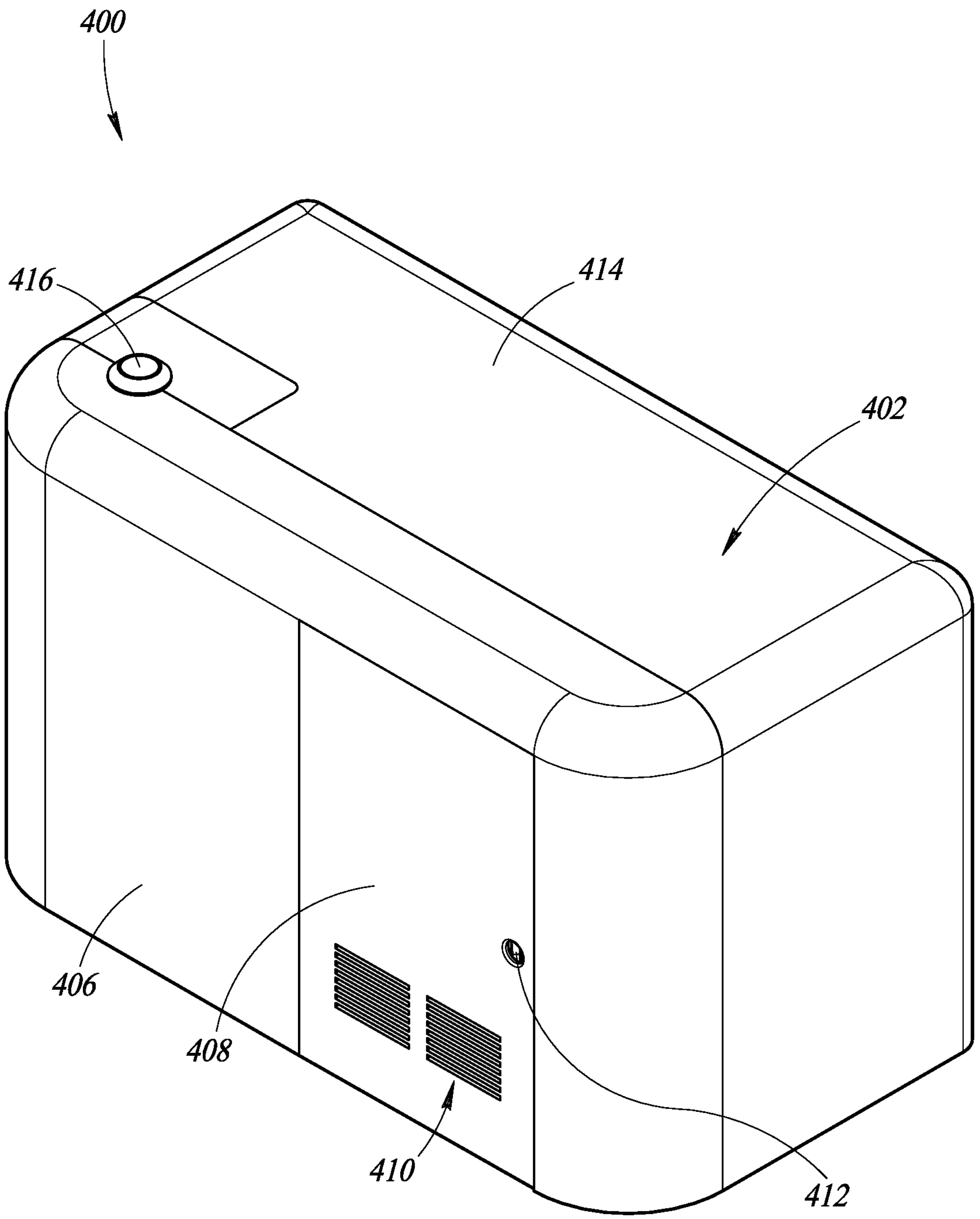
FIG. 22 illustrates a rear, top, and left side perspective view of a microfluidic system for processing biological samples.
Figure 23:
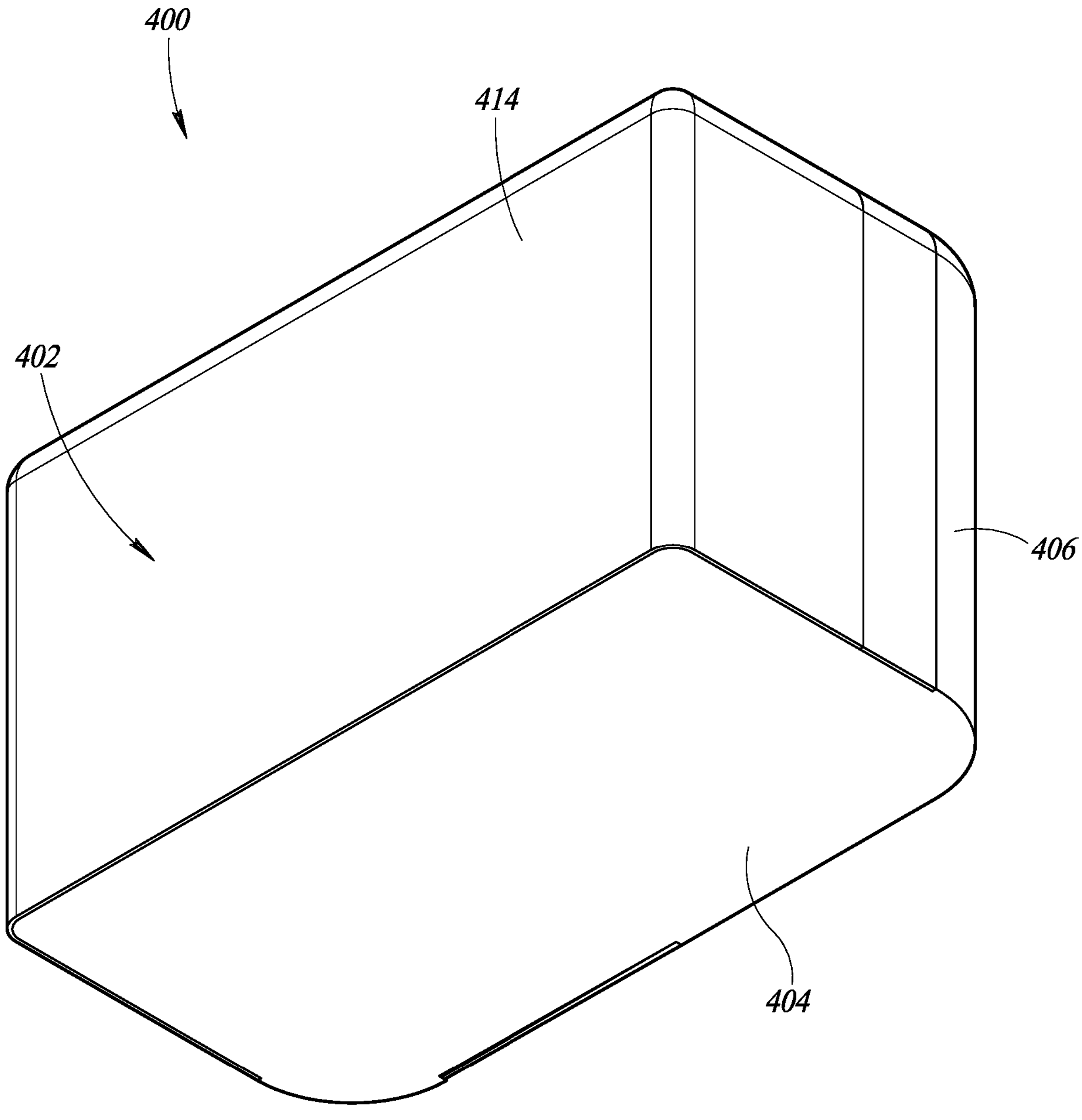
FIG. 23 illustrates a front, bottom, and right side perspective view of the microfluidic system of FIG. 22.
Figure 24:
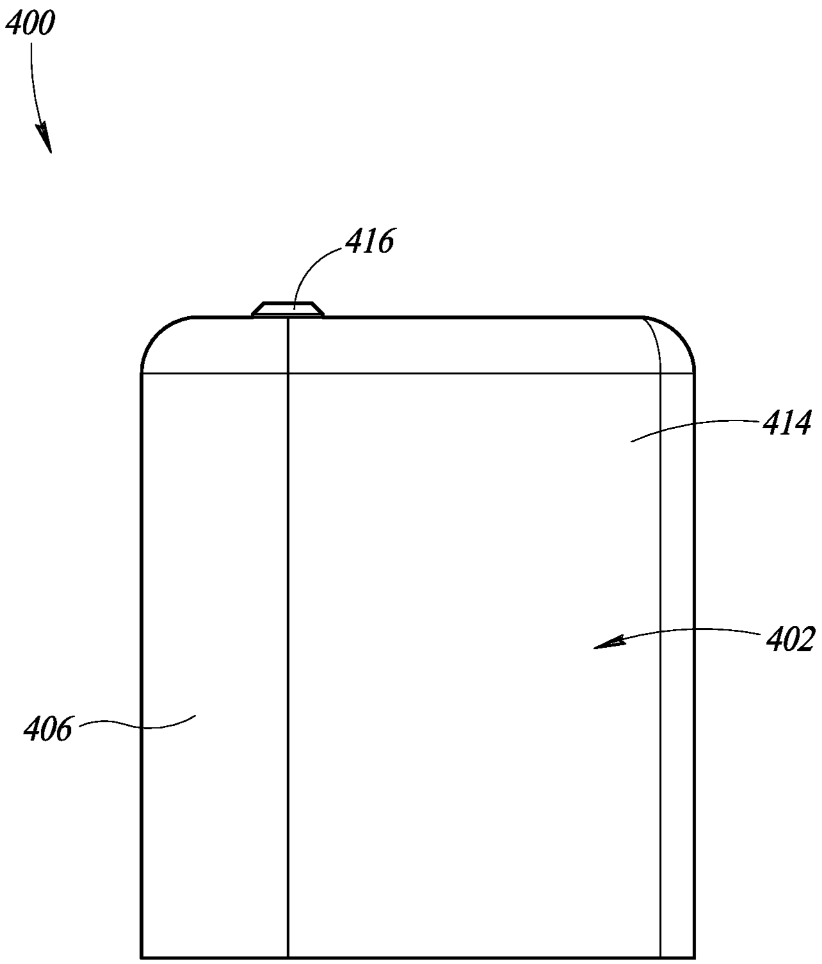
FIG. 24 illustrates a left side view of the microfluidic system of FIG. 22.
Figure 25:
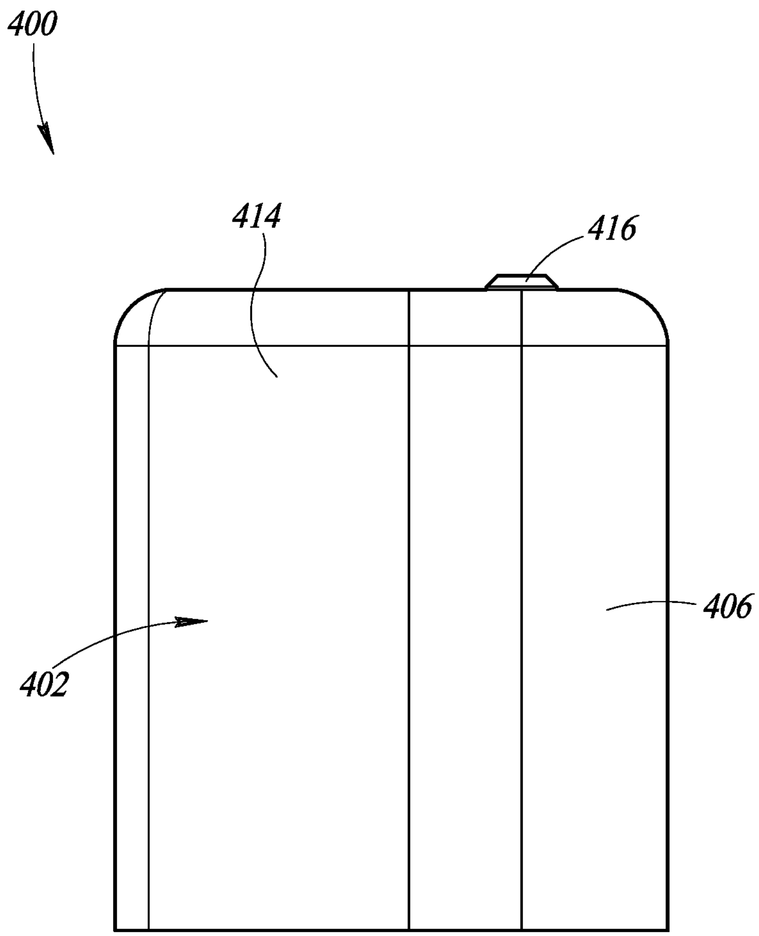
FIG. 25 illustrates a right side view of the microfluidic system of FIG. 22.
Figure 26:
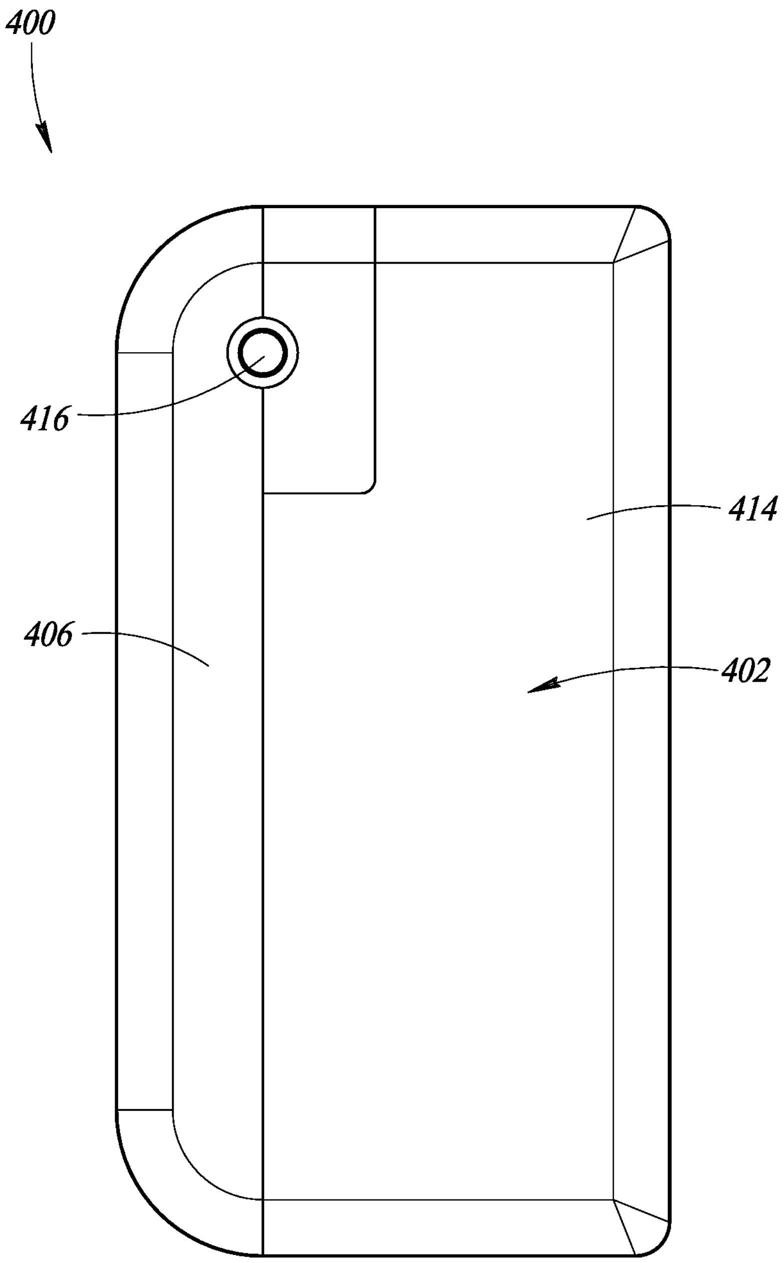
FIG. 26 illustrates a top plan view of the microfluidic system of FIG. 22.
Figure 27:
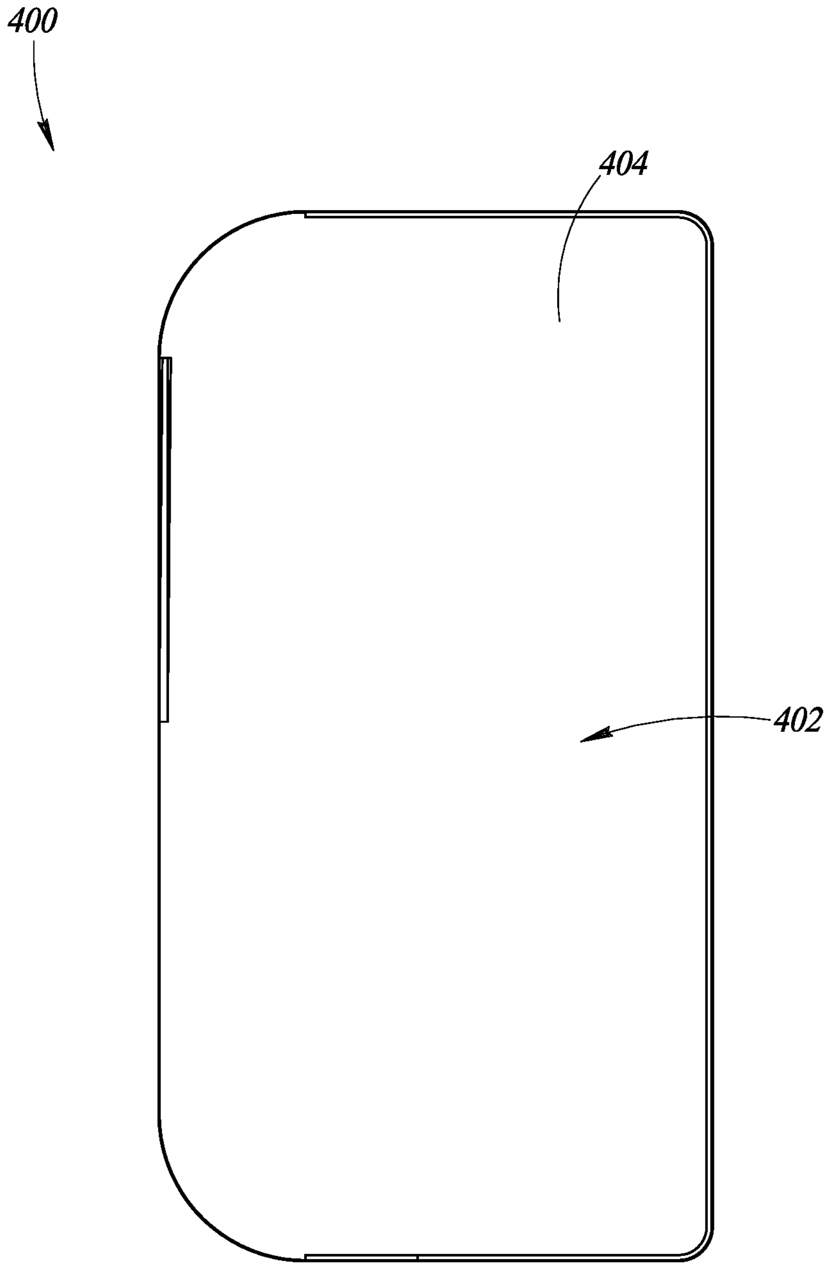
FIG. 27 illustrates a bottom plan view of the microfluidic system of FIG. 22.
Figure 28:
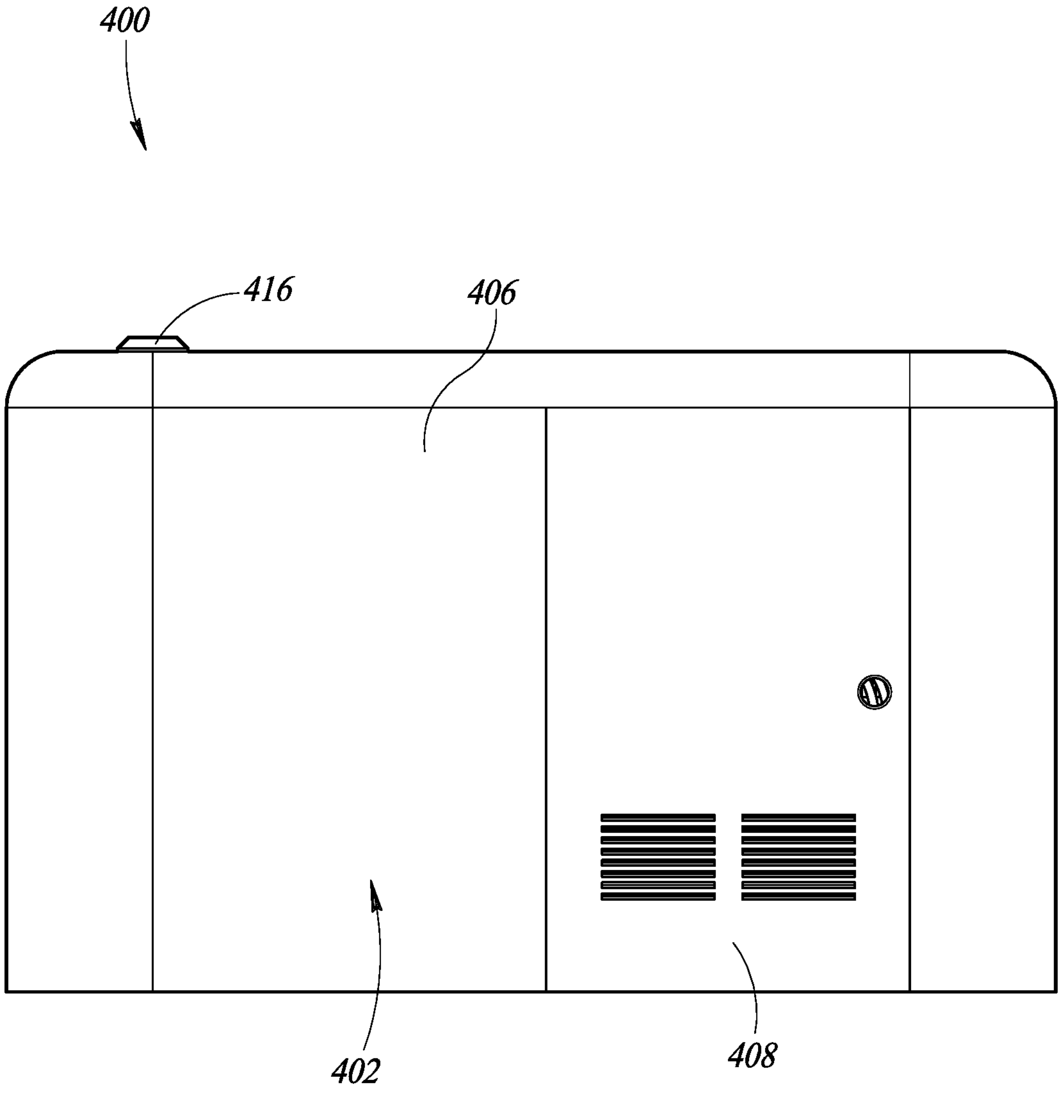
FIG. 28 illustrates a rear view of the microfluidic system of FIG. 22.
Figure 29:
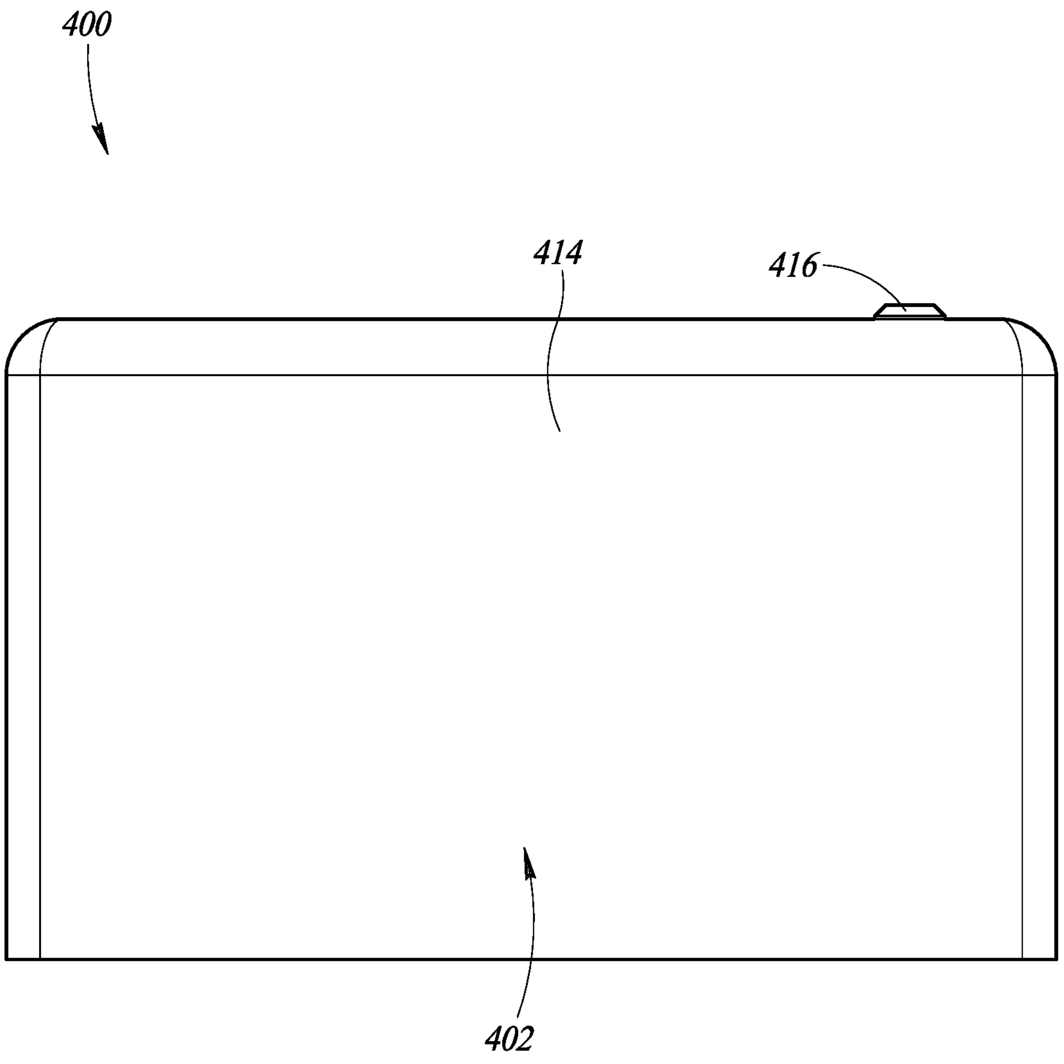
FIG. 29 illustrates a front view of the microfluidic system of FIG. 22.
Figure 30:
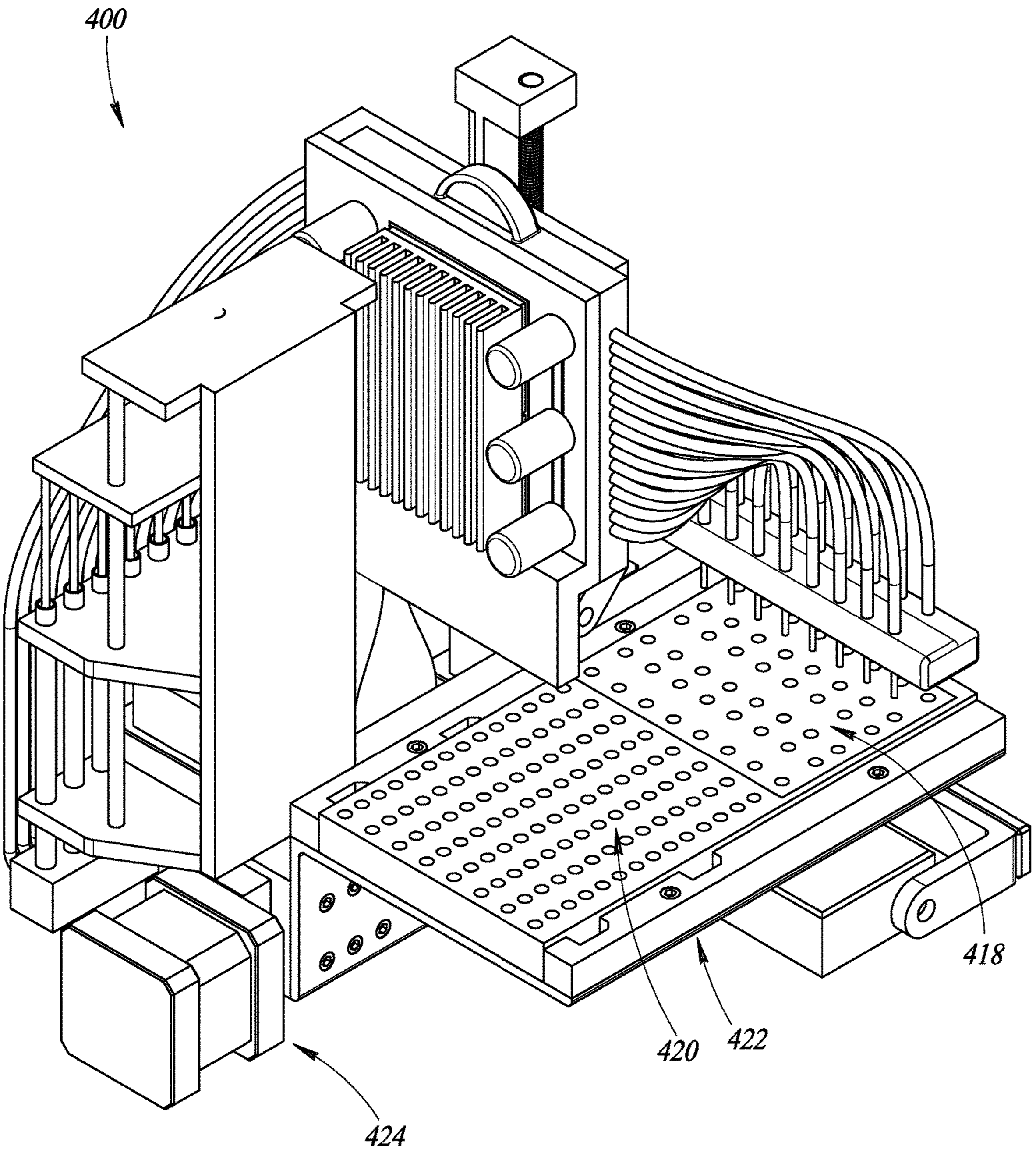
FIG. 30 illustrates a front, top, and left side perspective view of the microfluidic system of FIG. 22 with a housing thereof removed.
Figure 31:
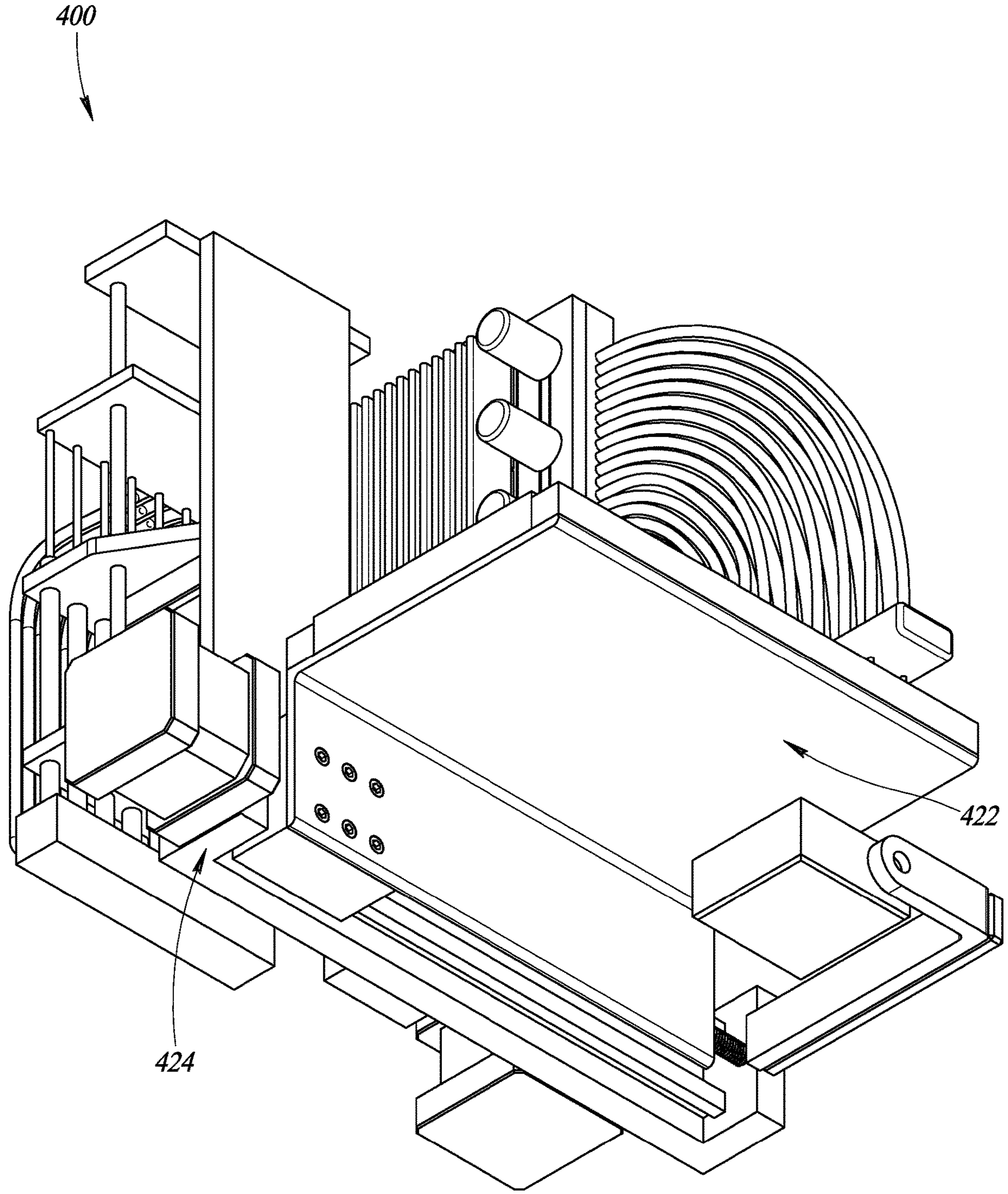
FIG. 31 illustrates a front, bottom, and left side perspective view of the microfluidic system of FIG. 22 with a housing thereof removed.
Figure 32:
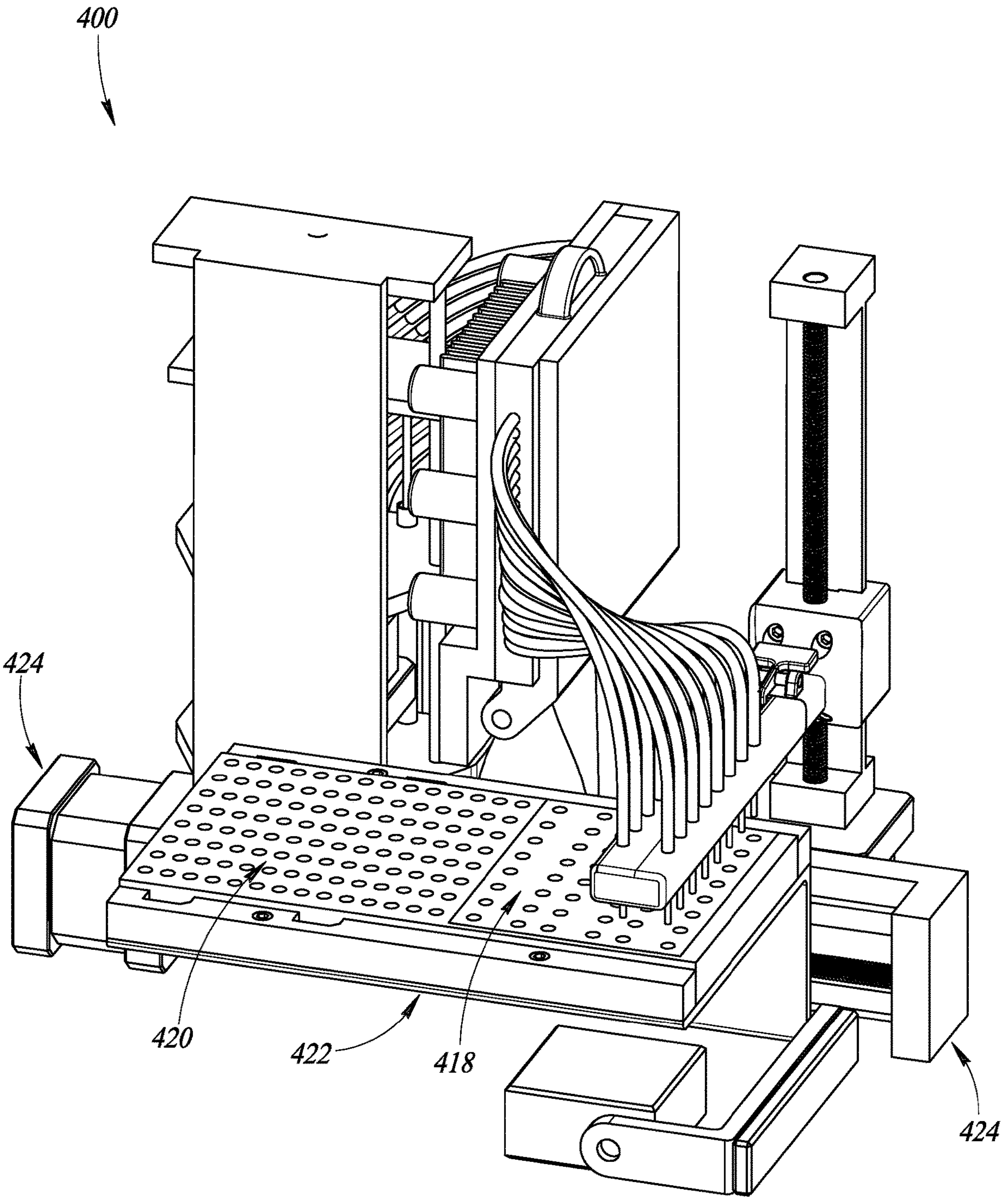
FIG. 32 illustrates a front, top, and right side perspective view of the microfluidic system of FIG. 22 with a housing thereof removed.
Figure 33:
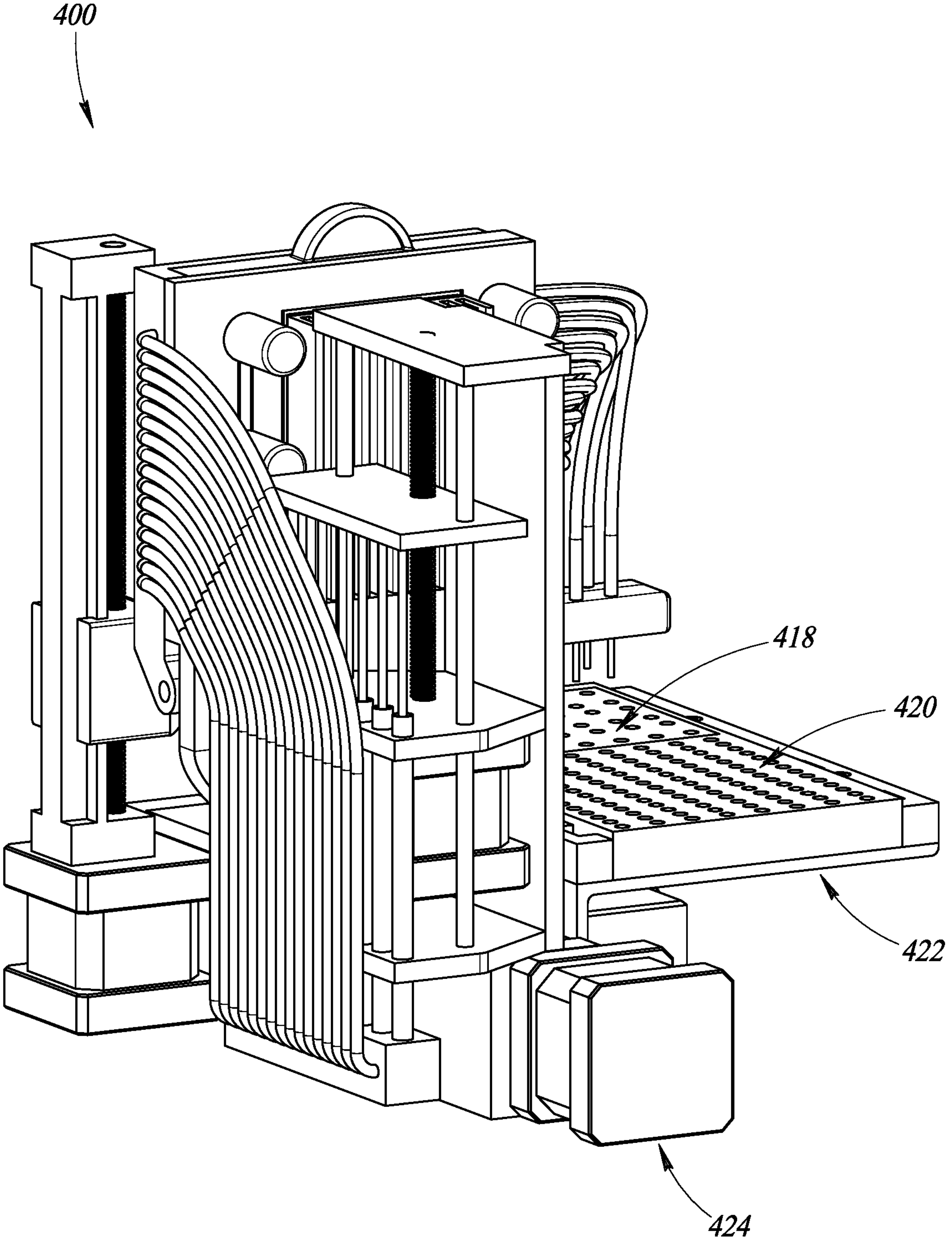
FIG. 33 illustrates a rear, top, and left side perspective view of the microfluidic system of FIG. 22 with a housing thereof removed.
Figure 34:
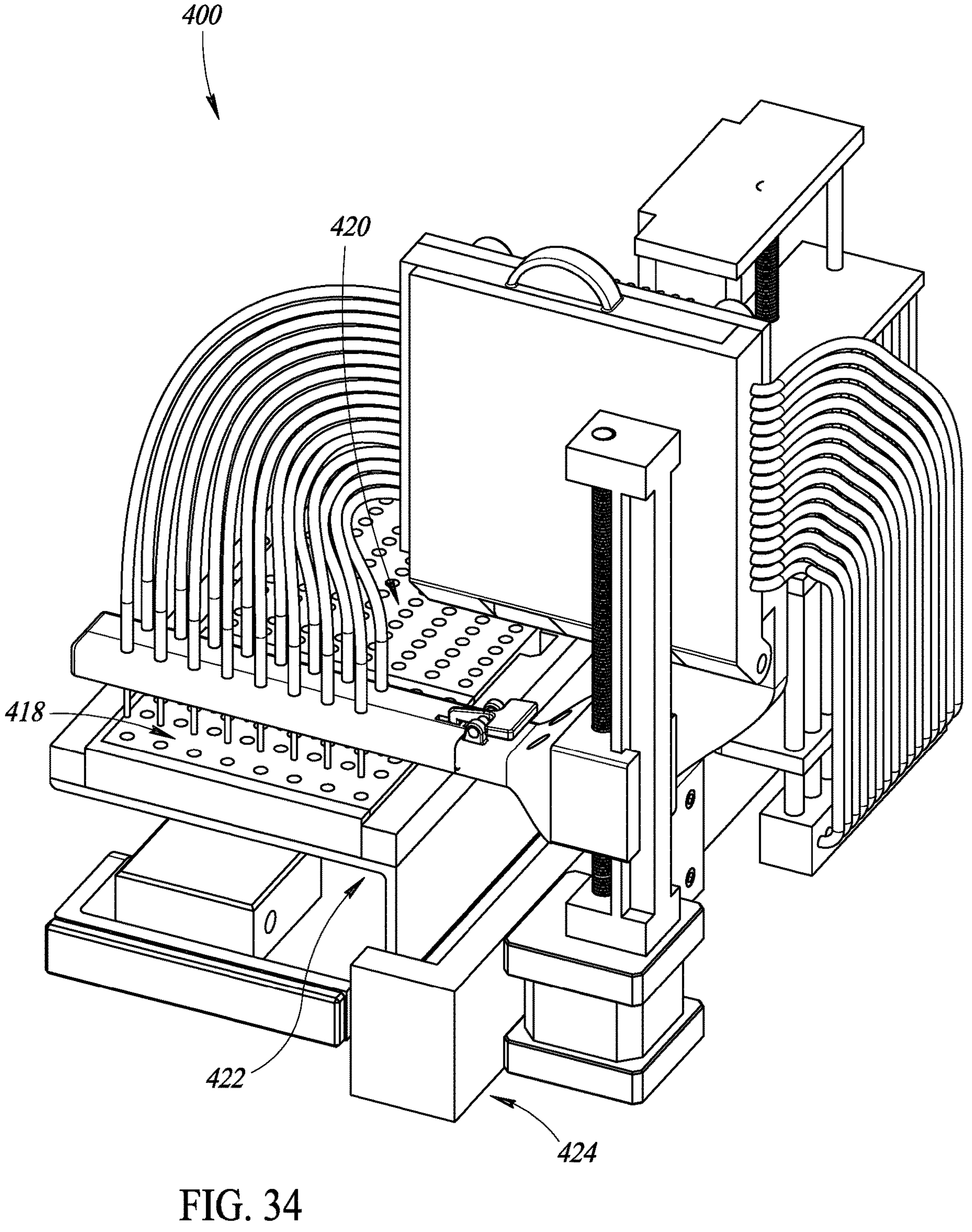
FIG. 34 illustrates a rear, top, and right side perspective view of the microfluidic system of FIG. 22 with a housing thereof removed.

FIG. 22 illustrates a rear, top, and left side perspective view of a microfluidic system 400, including a housing 402 thereof, for processing biological material. FIG. 23 illustrates a front, bottom, and right side perspective view of the housing 402. FIG. 24 illustrates a left side view of the housing 402. FIG. 25 illustrates a right side view of the housing 402. FIG. 26 illustrates a top plan view of the housing 402. FIG. 27 illustrates a bottom plan view of the housing 402. FIG. 28 illustrates a rear view of the housing 402. FIG. 29 illustrates a front view of the housing 402.

As used herein, terms such as "front," "forward," "back," "rearward," "behind," and other similar terminology, when used in the context of the microfluidic system 400, are used with respect to a viewer located on the side of the system 400 from which the viewer is expected to typically interact with and operate the system 400. Thus, in some cases, "front," "forward," and other similar terms refer to a feature being located in the direction of such a viewer, while words such as "back," "rearward," "behind," and other similar terms refer to a feature being located in the opposite direction. As used herein, terms of relative elevation, such as "top," "bottom," "upper," lower," "above," "below," "up," and "down," when used in the context of the microfluidic system 400, are used in their ordinary sense, that is, with respect to a direction of a gravitational force, such that gravity pulls objects down. As used herein, terms such as "right" and "left," when used in the context of the microfluidic system 400, refer to locations as viewed toward the front of the microfluidic system 400.

FIGS. 22-29 illustrate that the housing 402 of the microfluidic system 400 includes a bottom portion or bottom plate 404 that spans across the entire bottom surface of the housing 402 and provides a base or a foundation to which various other components of the system 400 and the housing 402 may be coupled. The housing 402 also includes a rear portion 406 that is rigidly coupled to, and that may be formed integrally with, the bottom plate 404. The rear portion 406 spans across the entire rear surface of the housing 402 except for an opening formed therein, and across rear portions of the top, left side, and right side surfaces of the housing 402. The housing 402 also includes a panel 408 that is removably installed and coupled to the rear portion 406 to cover the opening formed therein. The panel 408 includes slots 410 formed therein to allow air to flow into and out of the housing 402, and a port 412 formed therein to allow wires or cables, such as for carrying communications and/or or power, to extend into and out of the housing 402. In some cases the panel 408 may also be removed from the rest of the housing 402 to allow an operator or technician to access components inside the housing 402, such as for service or repair, through the opening formed in the rear portion 406.

The housing 402 also includes a front portion 414 that is rotatably coupled, such as hinged, to the rear portion 406, such that the front portion 414 can be rotated away from the rear portion 406 to open the housing 402 and allow an operator or a technician to interact with internal components of the microfluidic system 400. The front portion 414 spans across the entire front surface of the housing 402 and across front portions of the top, left side, and right side surfaces of the housing 402. A bottom end or edge of the front portion 414 can abut against outer edges of the bottom plate 404, and rear edges of the front portion 414 can abut against front edges of the rear portion 406, when the front portion 414 is in its closed position. In some implementations, the front portion 414 is rotatably coupled, such as by one or more hinges, to a top of the rear portion 406 such that the front portion 414 can rotate about a horizontal axis extending along the top surface of the housing 402 upwards and away from the rest of the system 400 to provide access to the rest of the components inside the housing 402. In other implementations, the front portion 414 is rotatably coupled, such as by one or more hinges, to a right side or a left side of the rear portion 406 such that the front portion 414 can rotate about a vertical axis extending along the left or the right surface of the housing 402 laterally outward and away from the rest of the system 400 to provide access to the rest of the components inside the housing 402.

The housing 402 also includes a single external physical button 416 that can allow an operator or technician to manually interact with the microfluidic system 400. In some implementations, the operator can open the housing 402 by moving its front portion 414, can supply biological samples and/or other materials to a set of wells or microwells inside the housing 402, close the housing 402 by moving its front portion 414, and then press or push the button 416 to initiate operation of the microfluidic system 400 and processing of the biological samples or other materials therein. In some implementations, the operator or technician may also press the button 416 to stop or halt operation of the microfluidic system 400 prior to completion of the processing, for example, in case an emergency or other unforeseen circumstance or situation arises.

FIGS. 30-34 illustrate various perspective views of the microfluidic system 400 with its housing 402 removed to illustrate internal components thereof. As illustrated in FIGS. 30-34, the microfluidic system 400 includes a microfluidic chip or a microfluidic plate 418, within which biological samples or other materials can be processed. The microfluidic system 400 also includes a microwell plate 420 having a plurality of microwells and a recess or slot or cavity to receive the microfluidic chip 418, so that the microwell plate 420 can carry the microfluidic chip 418. The microfluidic system 400 also includes a carriage or a tray 422 to which the microwell plate 420 can be secured or coupled. The microfluidic system 400 also includes a horizontal actuation system 424, to which the tray 422 can be coupled. In operation, the horizontal actuation system 424 can move the tray 422, and the microwell plate 420 and the microfluidic chip 418 with it, back and forth, and left and right, in a horizontal direction.

Figure 35:
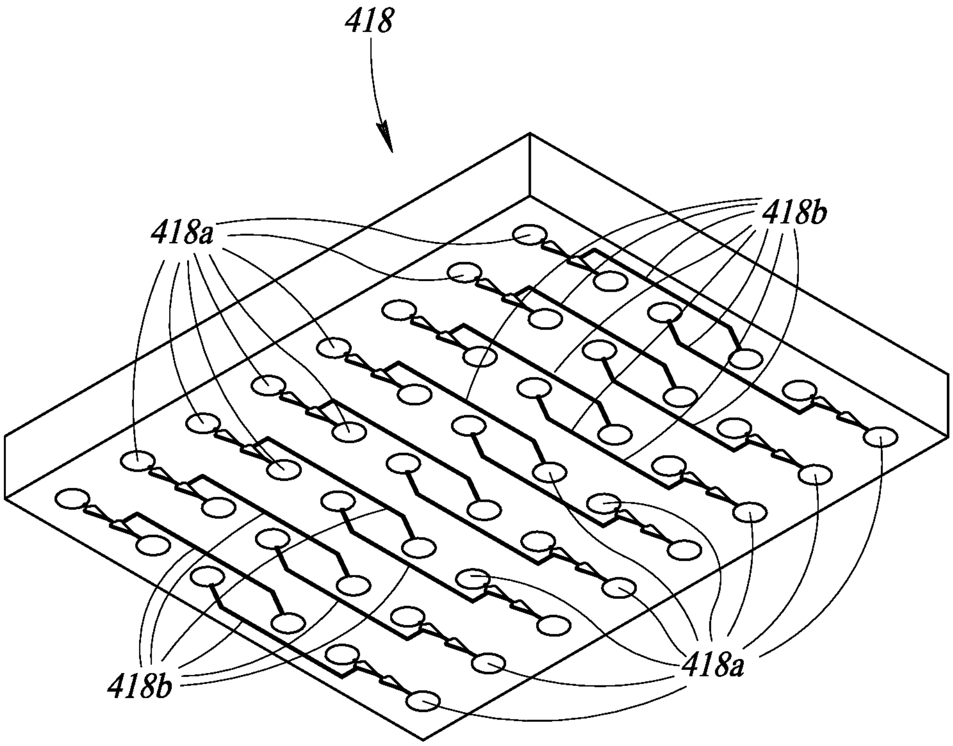
FIG. 35 illustrates a bottom perspective view of a microfluidic plate or chip of the microfluidic system of FIG. 22.

As illustrated in FIGS. 30-34, the microfluidic chip 418 includes a plurality of wells 418*a* that extend from a top surface thereof, vertically through a thickness of the chip 418, to a bottom surface thereof. FIG. 35 illustrates a perspective view of the underside, or of the bottom surface, of the microfluidic chip 418. As illustrated in FIG. 35, the microfluidic chip 418 includes a plurality of microchannels 418*b* and other features formed in its bottom surface. The microchannels 418*b* and other features are interconnected with one another and with the wells 418*a* to form a plurality of chambers and pathways that extend between the wells 418*a*. When the system 400 is in use, the microchannels 418*b* and the other features formed in the bottom surface of the chip 418 can direct fluids, biological samples, or other materials along the pathways, such as from a first one of the wells 418*a* to a second one of the wells 418*a*, such as in accordance with any of the embodiments of microfluidic systems described herein.

Figure 36:
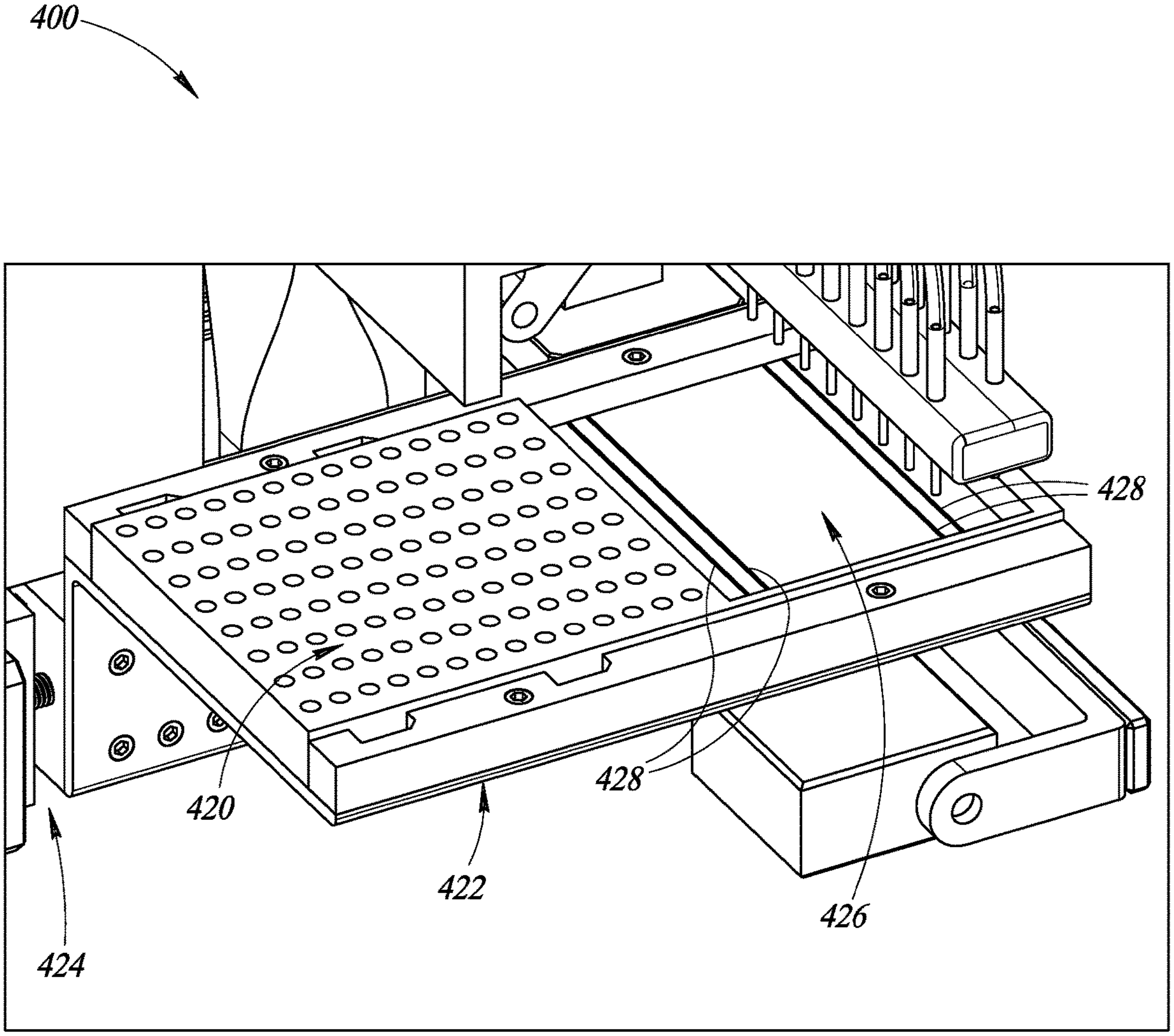
FIG. 36 illustrates a perspective view of a portion of the microfluidic system of FIG. 22 with the microfluidic chip of FIG. 35 removed.
Figure 37:
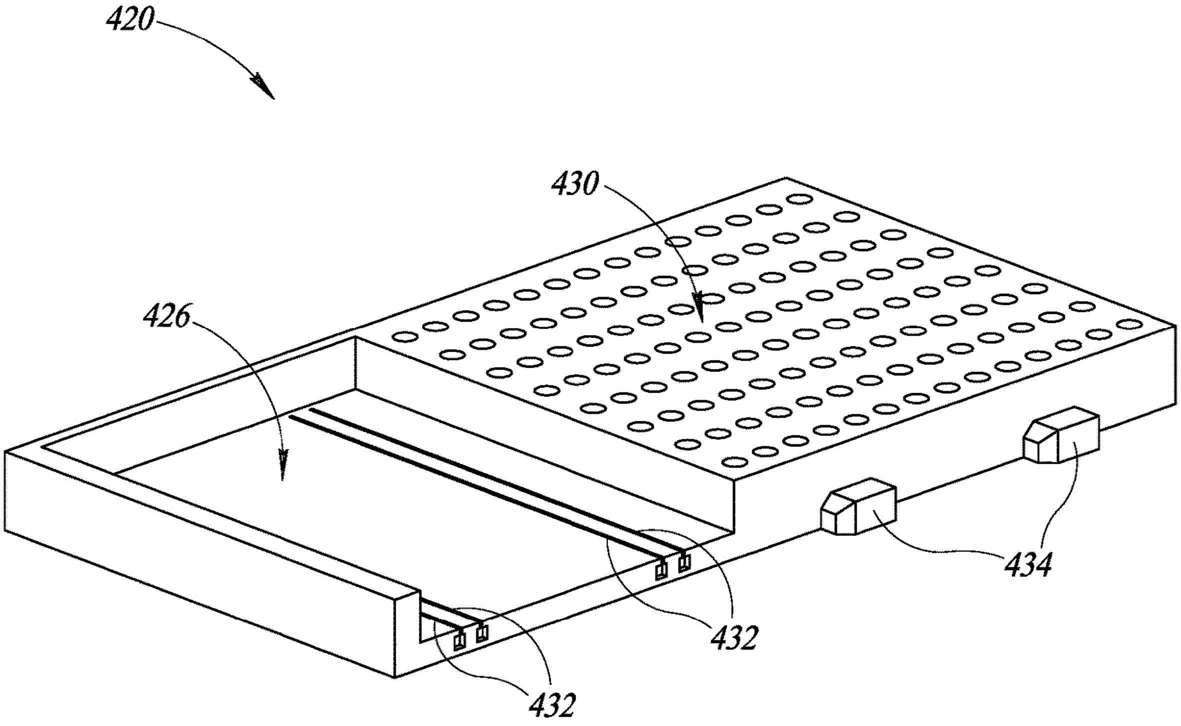
FIG. 37 illustrates a top perspective view of a microwell plate of the microfluidic system of FIG. 22.

FIG. 36 illustrates a portion of the microfluidic system 400 with the microfluidic chip 418 removed to illustrate additional features of the microwell plate 420. For example, FIG. 36 illustrates that the microwell plate 420 includes a cavity 426 at a right side thereof, and includes a set of electrically conductive tracks or leads 428 that extend horizontally across a bottom end of the cavity 426 from a front end thereof to a rear end thereof. FIG. 37 illustrates a rear perspective view of the microwell plate 420 isolated from the rest of the microfluidic system 400. As illustrated in FIG. 37, the microwell plate 420 includes the cavity 426 at a right side thereof and an array of a plurality of microwells 430 at a left side thereof.

The cavity 426 has a geometric shape comprising a right rectangular prism, and has dimensions, including a vertical depth, a horizontal length, and a horizontal width, that match, are the same as, or are identical to the corresponding dimensions of the microfluidic chip 418. As illustrated in FIG. 37, a front end of the cavity 426 is set back relative to a front end of the plate 420, a right end of the cavity 426 is set inward relative to a right end of the plate 420, a rear end of the cavity 426 extends all the way to, and is coincident with, a rear end of the plate 420, and a left end of the cavity 426 is located between one third and one half of the distance across the width of the plate 420 from the right end of the plate toward the left end of the plate. Thus, the cavity forms a slot or an enlarged groove that extends into the plate 420 from a rear end thereof toward a front end thereof. In use, the microfluidic chip 418 can be positioned within the cavity 426 such that a bottom surface of the cavity 426 faces the microfluidic channels 418*b* in the bottom surface of the chip 418 and defines or forms a bottom or lower boundary of chambers and pathways formed by the microfluidic channels 418*b*.

FIG. 37 also illustrates that the plate 420 includes a plurality of channels 432 formed in the bottom end or the bottom surface of the cavity 426. In the illustrated implementation, the plate 420 includes four such channels 432. Each of the channels 432 includes a relatively narrow top end portion that extends from the floor or the bottom surface of the cavity 426, downward into the plate 420 to a larger, wider bottom end portion. In the illustrated implementation, the top end portion of each of the channels 432 is rectangular in cross section and the bottom end portion of each of the channels 432 is square in cross-section, although in alternative implementations, the features could have different shapes. Each of the channels 432 extends horizontally, front-to-back through the plate 420 from a location proximate, and set back from, a front end of the plate 420, all the way to the rear end of the plate 420.

The array of the plurality of microwells 430 may include any suitable number of individual microwells 430. In the illustrated implementation, the array of microwells 430 includes one hundred and twelve microwells 430, arranged in fourteen equally spaced rows extending front-to-back and eight equally spaced columns extending from side-to-side across the plate 420. As illustrated in FIG. 37, a front end of the array of microwells 430 is set back relative to a front end of the plate 420, a left end of the array of microwells 430 is set inward relative to a left end of the plate 420, a rear end of the array of microwells 430 is set forward relative to a rear end of the plate 420, and a left end of the array of microwells 430 is located between two thirds and one half of the distance across the width of the plate 420 from the left end of the plate 420 toward the right end of the plate 420.

FIG. 37 also illustrates that the plate 420 includes a plurality of arms or knobs or protrusions 434 that extend horizontally forward and rearward from front and rear ends, respectively, of the plate 420. In the illustrated implementation, the plate 420 includes two protrusions 434 that extend rearward from a rear end of the plate 420 and two protrusions 434 that extend forward from a front end of the plate 420.

Figure 38:
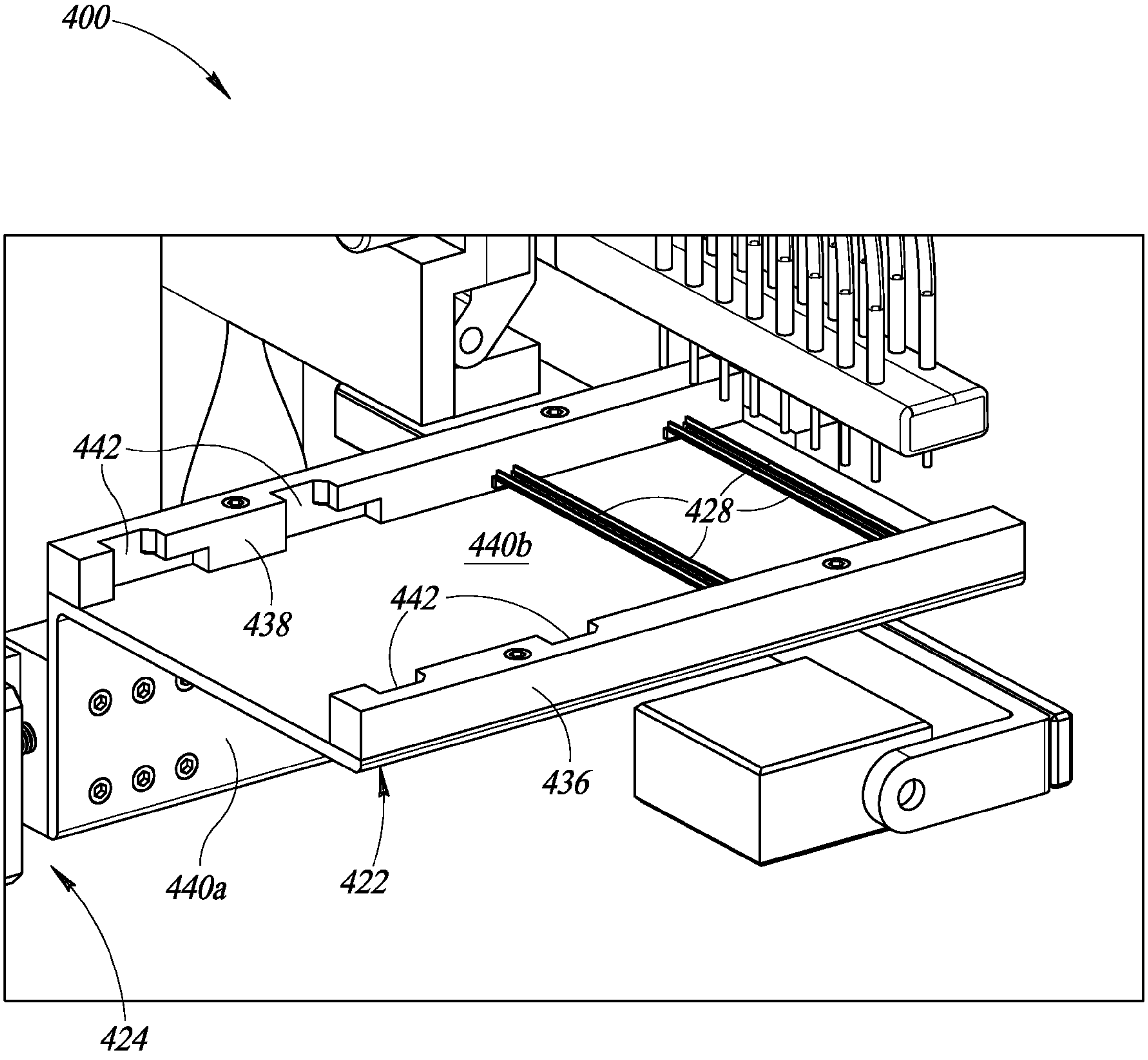
FIG. 38 illustrates a perspective view of a portion of the microfluidic system of FIG. 22 with the microfluidic chip of FIG. 35 and the microwell plate of FIG. 37 removed.

FIG. 38 illustrates a portion of the microfluidic system 400 with the microfluidic chip 418 and the microwell plate 420 removed to illustrate additional features of the tray 422 and the electrically conductive leads 428. For example, FIG. 38 illustrates that the tray 422 includes an angle bracket 440 that extends side-to-side and left-to-right and that has a first, vertical leg portion 440*a* coupled to the horizontal actuation system 424 and a second, horizontal leg portion 440*b* arranged at a right angle to the first, vertical leg portion 440*a*. The tray 422 also includes a front rail 436 that is coupled to an upper surface of a front end of the horizontal leg portion 440*b* of the bracket 440, and a rear rail 438 that is coupled to an upper surface of a rear end of the horizontal leg portion 440*b* of the bracket 440. The front and rear rails 436, 438, are parallel and extend side-to-side and left-to-right along the upper surface of the bracket 440.

As illustrated in FIG. 38, the front and rear rails 436, 438 each include a plurality of recesses or grooves 442 configured to mate with the protrusions of the plate 420 to lock or secure the plate 420 to the top surface of the bracket 440 between the front and rear rails 436 and 438. For example, the rear rail 438 includes two grooves 442 that extend rearward partially into the rail 438 from a front face thereof. In the illustrated implementation, each of the grooves 442 in the rear rail 438 also extend down into and through the rail 438 from a top end thereof to a bottom end thereof, and then from left to right along the bottom end of the rail 438. As another example, the front rail 436 includes two grooves 442 that extend forward partially into the rail 436 from a rear face thereof. In the illustrated implementation, each of the grooves 442 in the front rail 436 also extend down into and through the rail 436 from a top end thereof to a bottom end thereof, and then from left to right along the bottom end of the rail 436.

To secure the plate 420 to the tray 422, the plate 420 is positioned over the tray 422 so that its protrusions 434 are aligned with the grooves 442. The plate 420 can then be lowered into position on the tray 422 between the front and rear rails 436, 438, as the protrusions 434 travel down through the grooves 442, until a bottom surface of the plate 420 rests on an upper surface of the horizontal leg 440*b* of the bracket 440 of the tray 422. The plate 420 is then moved to the right so that the protrusions 434 travel to the right through the grooves 442, thereby securing the plate 420 to the tray 422.

FIG. 38 also illustrates the location of the electrically conductive tracks or leads 428 when the plate 420 and the chip 418 are secured to the tray 422. Each of the conductive leads 428 includes a relatively narrow top end portion that extends from the top end of the lead 428, downward to a larger, wider bottom end portion thereof. The top end portion of each of the conductive leads 428 is rectangular in cross section and has a size and a shape corresponding to the size and the shape of the top end portions of the channels 432, and the bottom end portion of each of the conductive leads 428 is square in cross-section and has a size and a shape corresponding to the size and the shape of the bottom end portions of the channels 432. Thus, each conductive lead 428 can be positioned, such as snugly, within a respective one of the channels 432. Each of the conductive leads 428 extends horizontally, front-to-back between the front and rear rails 436 and 438 from a location proximate, and set back from, the rear end of the front rail 436, all the way to a front end of the rear rail 438. In use, the conductive leads 428 are not typically located in the positions illustrated in FIG. 38 without the plate 420 present, but the conductive leads 428 are illustrated in such positions in FIG. 38 with the plate 420 removed for purposes of clarity and illustration.

Figure 39:
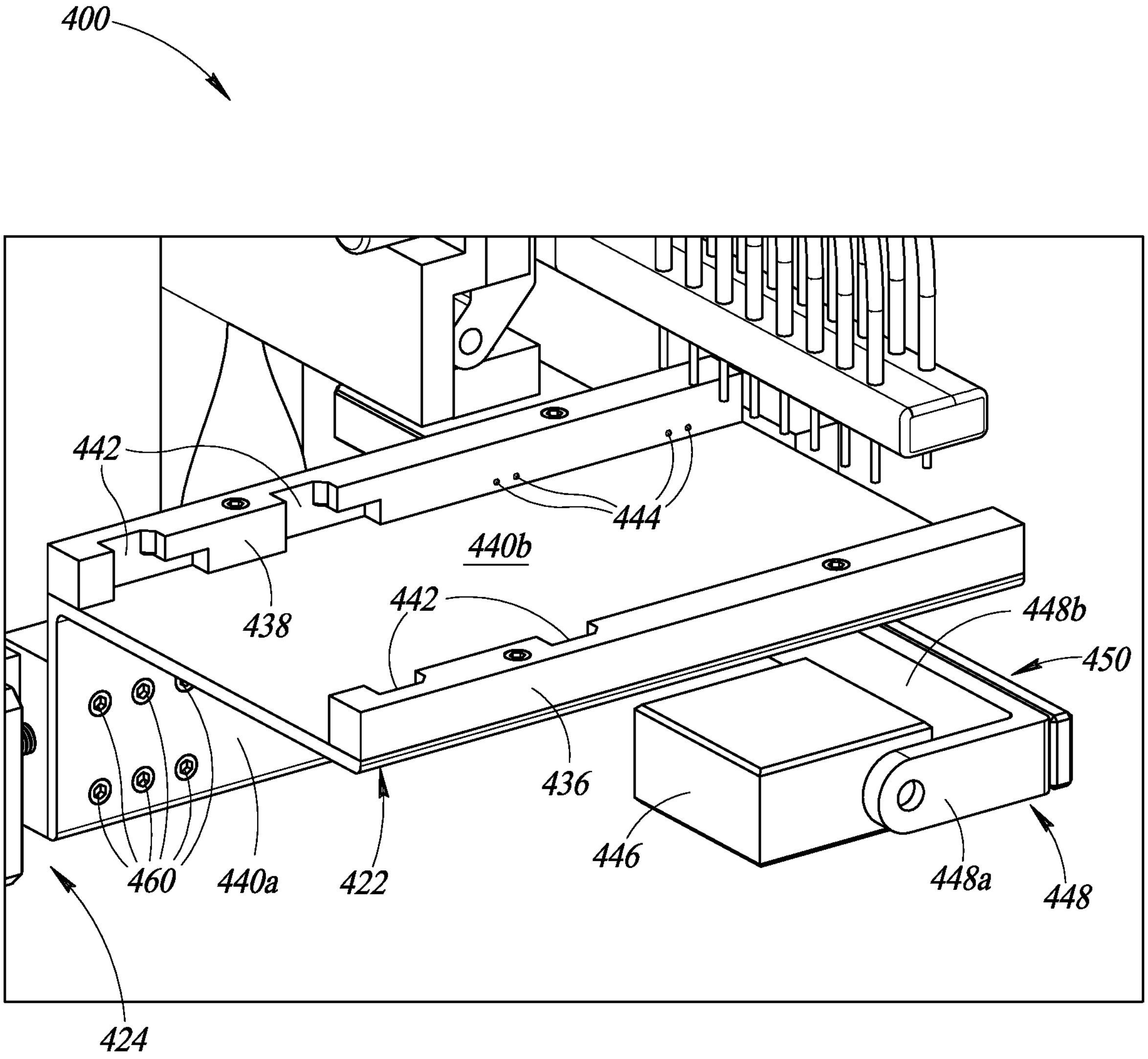
FIG. 39 illustrates a perspective view of a portion of the microfluidic system of FIG. 22 with the microfluidic chip, the microwell plate, and conductive leads thereof removed.

FIG. 39 illustrates a portion of the microfluidic system 400 with the microfluidic chip 418, the microwell plate 420, and the conductive leads 428 removed to illustrate additional features of the tray 422. For example, FIG. 39 illustrates that the tray 422 includes a set of electrically conductive terminals 444, each of which may include a conductive ball mounted in the rear rail 438 and biased forward from the rear rail 438, such as by a spring within the rear rail 438. The terminals 444 can be electrically coupled to a control system configured to operate the microfluidic system 400, such that the control system can control electrical voltages and/or currents supplied to each of the conductive leads 428.

As illustrated in FIGS. 36 and 37, the conductive leads 428 extend through the plate 420 and are exposed to the cavity 426 in the plate 420. Thus, the conductive leads 428 may also be exposed to one or more of the wells 418*a* and/or one or more of the microchannels 418*b* of the microfluidic chip 418. The control system can therefore be configured to control electrical voltages and/or currents supplied to the conductive leads 428, such as to control the processing of fluids, biological samples, and/or other materials within the microfluidic chip 418, such as in accordance with any of the embodiments of microfluidic systems described herein.

FIG. 39 also illustrates that the microfluidic system 400 includes a rotational actuation system including a first actuator 446, which may include an electrical motor, a servo motor, or any other suitable actuator that can generate torque, such as from electrical power, as well as an angle bracket 448 and a magnet 450. The first actuator 446 may be rigidly secured to, for example, an upper surface of the bottom plate 404 of the housing 402 at a location below the tray 422, below the plate 420 when the plate 420 is secured to the tray 422, and below the chip 418 when the chip 418 is positioned within the cavity 426 in the plate 420 and the plate 420 is secured to the tray 422.

An output or a driven rod of the first actuator 446 is rigidly coupled the angle bracket 448, which includes a first arm 448*a* and a second arm 448*b* perpendicular to the first arm 448*a*, such as to the first arm 448*a* thereof. The first actuator 446 can generate torque that rotates the first arm 448*a* to rotate about a horizontal axis extending front-to-back from a first position, shown in FIG. 39, in which the first arm 448*a* extends to the right of the output of the actuator 446, to a second position, in which the first arm 448*a* extends upwards from the output of the actuator 446, to a third position, in which the first arm 448*a* extends to the left of the output of the actuator 446, and back again, or through some smaller portion of such a range of travel.

The second arm 448*b* of the angle bracket 448 can be secured to the first arm 448*a* at a right angle such that it extends rearward. Thus, when the first arm 448 extends upwards, the second arm 448*b* extends rearward directly above the actuator 446, and horizontally from front-to-back underneath the tray 422, underneath the plate 420 when the plate 420 is secured to the tray 422, and underneath the chip 418 when the chip 418 is positioned within the cavity 426 in the plate 420 and the plate 420 is secured to the tray 422. The magnet 450 is secured to the second arm 448*b* of the angle bracket 448 such that, when the angle bracket 448 extends upward from the actuator 446, the magnet 450 is on top of the second arm 448*b* and adjacent to the tray 422.

The rotational actuation system and its first actuator 446 can be electrically or otherwise communicatively coupled to the control system, which can be configured to operate the first actuator 446, such that the control system can control rotation of the magnet 450 with respect to the actuator 446, the tray 422, the plate 420, and the chip 418 when the plate 420 and chip 418 are secured to the tray 422. Thus, the control system can be configured to control movement of the magnet 450 and a magnetic field generated by the magnet 450, such as to control the processing of fluids, biological samples, and/or other materials within the microfluidic chip 418, such as in accordance with any of the embodiments of microfluidic systems described herein.

Figure 40:
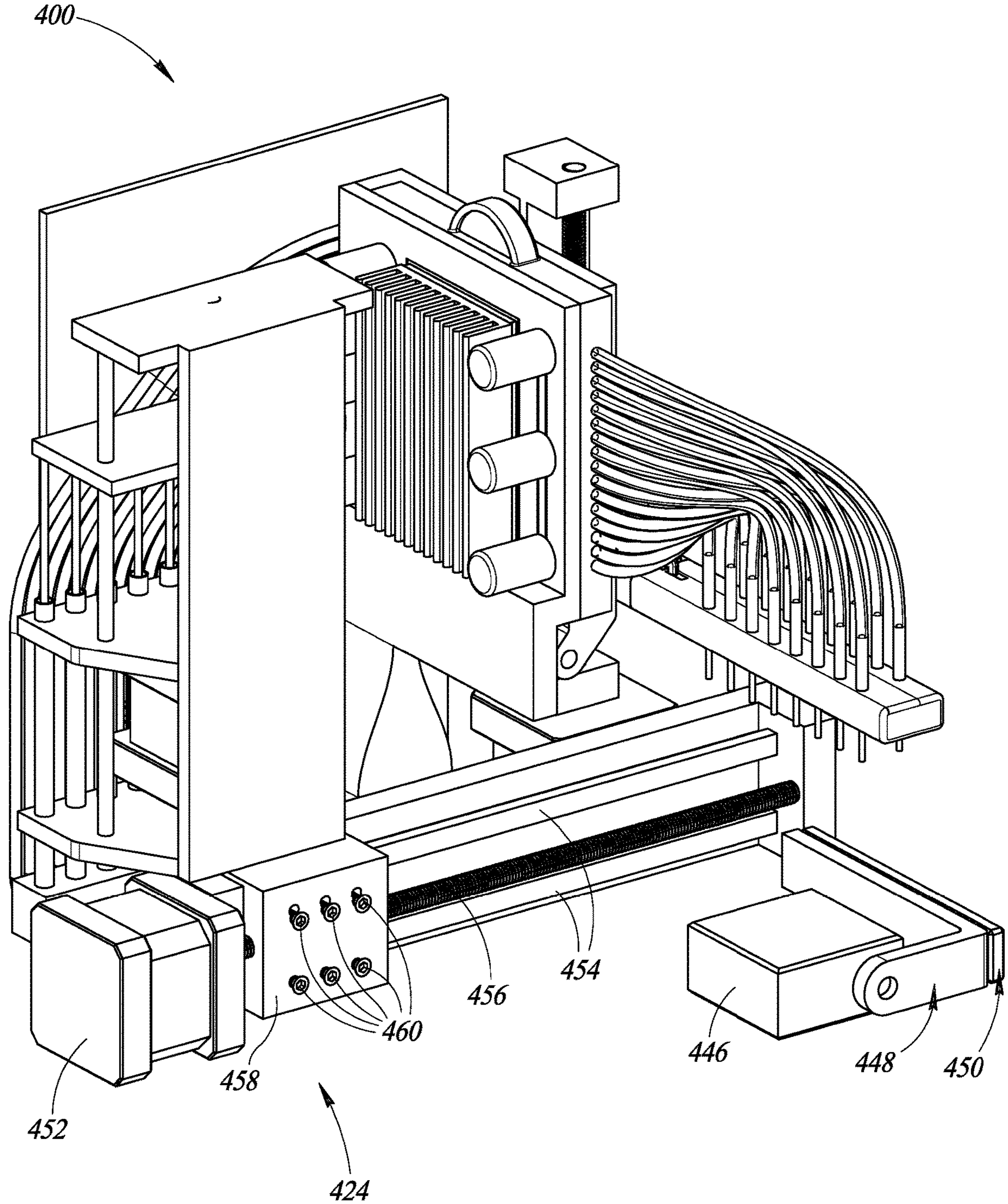
FIG. 40 illustrates a perspective view of the microfluidic system of FIG. 22 with the microfluidic chip, the microwell plate, the conductive leads, and a tray thereof removed.

FIG. 40 illustrates a perspective view of the microfluidic system 400 with the microfluidic chip 418, the microwell plate 420, the conductive leads 428, and the tray 422 removed to illustrate other components, including the horizontal actuation system 424, in greater detail. As illustrated in FIG. 40, the horizontal actuation system 424 includes an electrical motor, a servo motor, or any other suitable second actuator 452 that can generate torque, such as from electrical power. The horizontal actuation system 424 also includes an elongate guide rail 454 that is rigidly secured and coupled to the second actuator 452, and that extends side-to-side and to the right from the actuator 452. The second actuator 452 and the guide rail 454 may be rigidly secured to, for example, an upper surface of the bottom plate 404 of the housing 402 at a location below the tray 422.

The horizontal actuation system 424 also includes a threaded rod 456 that is coupled to an output or a driven rod of the second actuator 452. The second actuator 452 can generate torque that rotates the threaded rod 456 about its own central longitudinal axis, which is a horizontal axis extending side-to-side from the second actuator 452 toward the right and underneath the tray 422. The horizontal actuation system 424 also includes a travelling block 458, which is secured to and mounted on the guide rail 454 such that the travelling block 458 can travel linearly left-to-right along the length of the guide rail 454. For example, the travelling block 458 may include one or more grooves, such as with undercut portions thereof, and the guide rail 454 may include one or more ridges having shapes corresponding to those of the grooves, such that the ridges can be positioned within the grooves to secure the travelling block 458 to the guide rail 454. As another example, the guide rail 454 may include one or more grooves, such as with undercut portions thereof, and the travelling block 458 may include one or more ridges having shapes corresponding to those of the grooves, such that the ridges can be positioned within the grooves to secure the travelling block 458 to the guide rail 454.

As illustrated in FIG. 40, the threaded rod 456 extends through a conduit extending through the travelling block 458. In some implementations, the conduit extending through the travelling block 458 is threaded, with threads of the conduit corresponding to the threads of the threaded rod 456, and the threads of the conduit may be engaged and interlocked with the threads of the threaded rod 456. Thus, due to the engagement of these threads and the engagement of the travelling block 458 with the guide rail 454, when the actuator 452 generates torque and induces rotation of the threaded rod 456, the rotation of the threaded rod 456 induces linear movement of the travelling block 458 along the length of the guide rail 454 from side-to-side. By turning the threaded rod 456 in a first direction, such as clockwise or counterclockwise, the threaded rod 456 can cause the travelling block 458 to travel in a first direction, such as to the right or to the left. By turning the threaded rod 456 in a second direction opposite to the first, such as clockwise or counterclockwise, the threaded rod 456 can cause the travelling block 458 to travel in a second direction opposite to the first direction, such as to the right or to the left.

As illustrated in FIGS. 39 and 40, the tray 422 can be rigidly coupled and secured to the travelling block 458, such as by an adhesive or a plurality of mechanical fasteners such as screws or bolts 460. Thus, movement of the travelling block 458 can induce a corresponding or a matching movement of the tray 422, and thus of the microwell plate 420 and of the microfluidic chip 418. Thus, the actuator 452 can be used as described herein to move the microwell plate 420 and the microfluidic chip 418 side-to-side and left-to-right within the system 400. The horizontal actuation system 424 and its second actuator 452 can be electrically or otherwise communicatively coupled to the control system, which can be configured to operate the second actuator 452, such that the control system can control horizontal and side-to-side movement of the microwell plate 420 and the microfluidic chip 418 when the plate 420 and chip 418 are secured to the tray 422.

Figure 41:
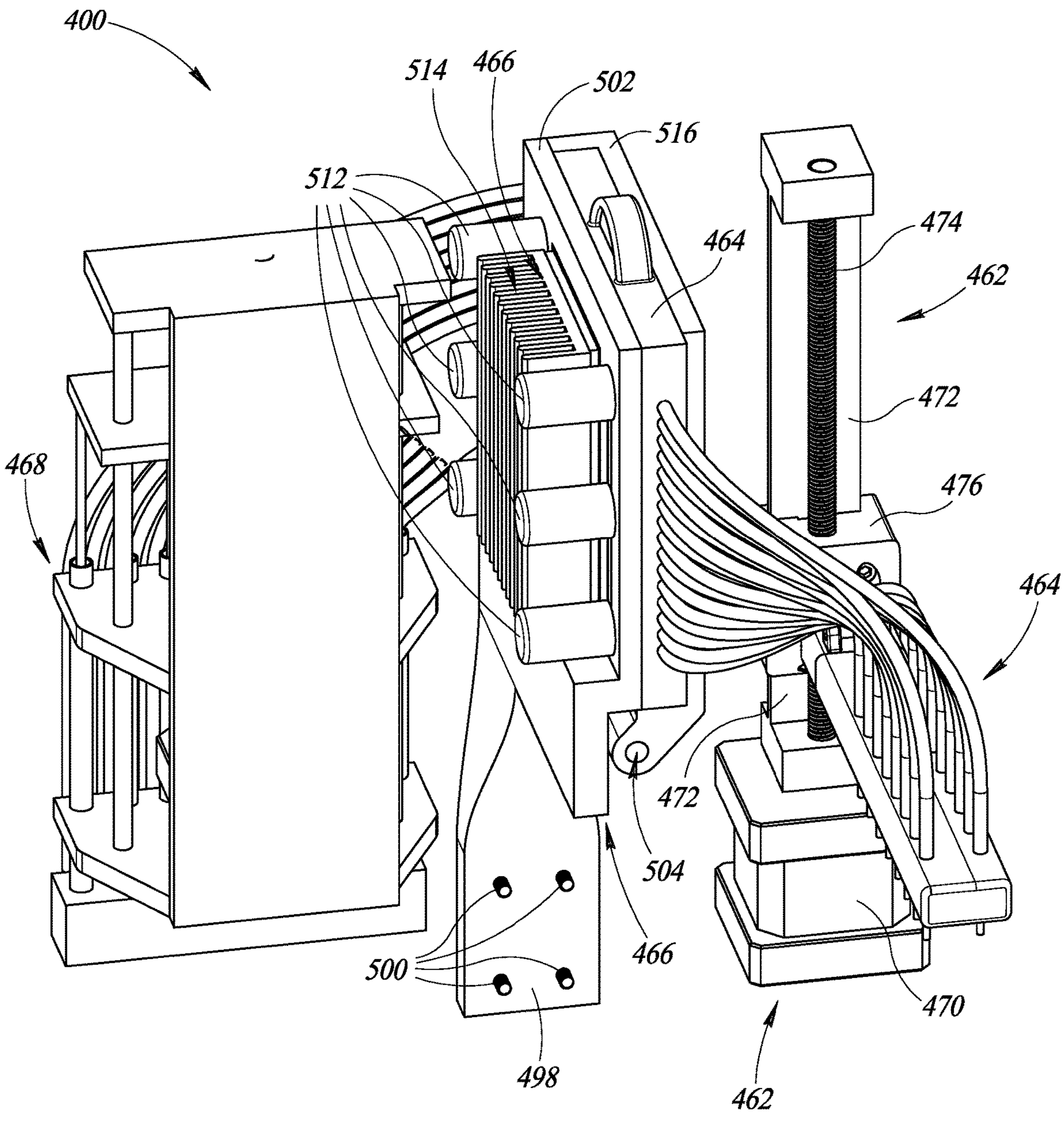
FIG. 41 illustrates a perspective view of the microfluidic system as illustrated in FIG. 40 with additional components removed.

FIG. 41 illustrates a perspective view of the microfluidic system 400 as illustrated in FIG. 40 with additional components, including the rotational actuation system and the horizontal actuation system 424 removed to more clearly illustrate other components. As illustrated in FIG. 41, the microfluidic system 400 includes a vertical actuation system 462, a micropipette system 464, a cradle 466 enclosing a portion of the micropipette system 464, and a pump system 468 configured to control at least part of the operation of the micropipette system 464. As illustrated in FIG. 41, the vertical actuation system 462 includes an electrical motor, a servo motor, or any other suitable third actuator 470 that can generate torque, such as from electrical power. The vertical actuation system 462 also includes an elongate guide rail 472 that is rigidly secured and coupled to the second actuator 470, and that extends up-and-down and upwards from the actuator 470. The second actuator 470 may be rigidly secured to, for example, an upper surface of the bottom plate 404 of the housing 402 at a location behind the horizontal actuation system 424.

The vertical actuation system 462 also includes a threaded rod 474 that is coupled to an output or a driven rod of the third actuator 470. The third actuator 470 can generate torque that rotates the threaded rod 474 about its own central longitudinal axis, which is a vertical axis extending up-and-down from the third actuator 470 upward. The vertical actuation system 462 also includes a travelling block 476, which is secured to and mounted on the guide rail 472 such that the travelling block 476 can travel linearly up-and-down along the length of the guide rail 472. For example, the travelling block 476 may include one or more grooves, such as with undercut portions thereof, and the guide rail 472 may include one or more ridges having shapes corresponding to those of the grooves, such that the ridges can be positioned within the grooves to secure the travelling block 476 to the guide rail 472. As another example, the guide rail 472 may include one or more grooves, such as with undercut portions thereof, and the travelling block 476 may include one or more ridges having shapes corresponding to those of the grooves, such that the ridges can be positioned within the grooves to secure the travelling block 476 to the guide rail 472.

As illustrated in FIG. 41, the threaded rod 474 extends through a conduit extending through the travelling block 476. In some implementations, the conduit extending through the travelling block 476 is threaded, with threads of the conduit corresponding to the threads of the threaded rod 474, and the threads of the conduit may be engaged and interlocked with the threads of the threaded rod 474. Thus, due to the engagement of these threads and the engagement of the travelling block 476 with the guide rail 472, when the actuator 470 generates torque and induces rotation of the threaded rod 474, the rotation of the threaded rod 474 induces linear movement of the travelling block 476 along the length of the guide rail 472 up-and-down. By turning the threaded rod 474 in a first direction, such as clockwise or counterclockwise, the threaded rod 474 can cause the travelling block 476 to travel in a first direction, such as up or down. By turning the threaded rod 474 in a second direction opposite to the first, such as clockwise or counterclockwise, the threaded rod 474 can cause the travelling block 476 to travel in a second direction opposite to the first direction, such as up or down.

Figure 42:
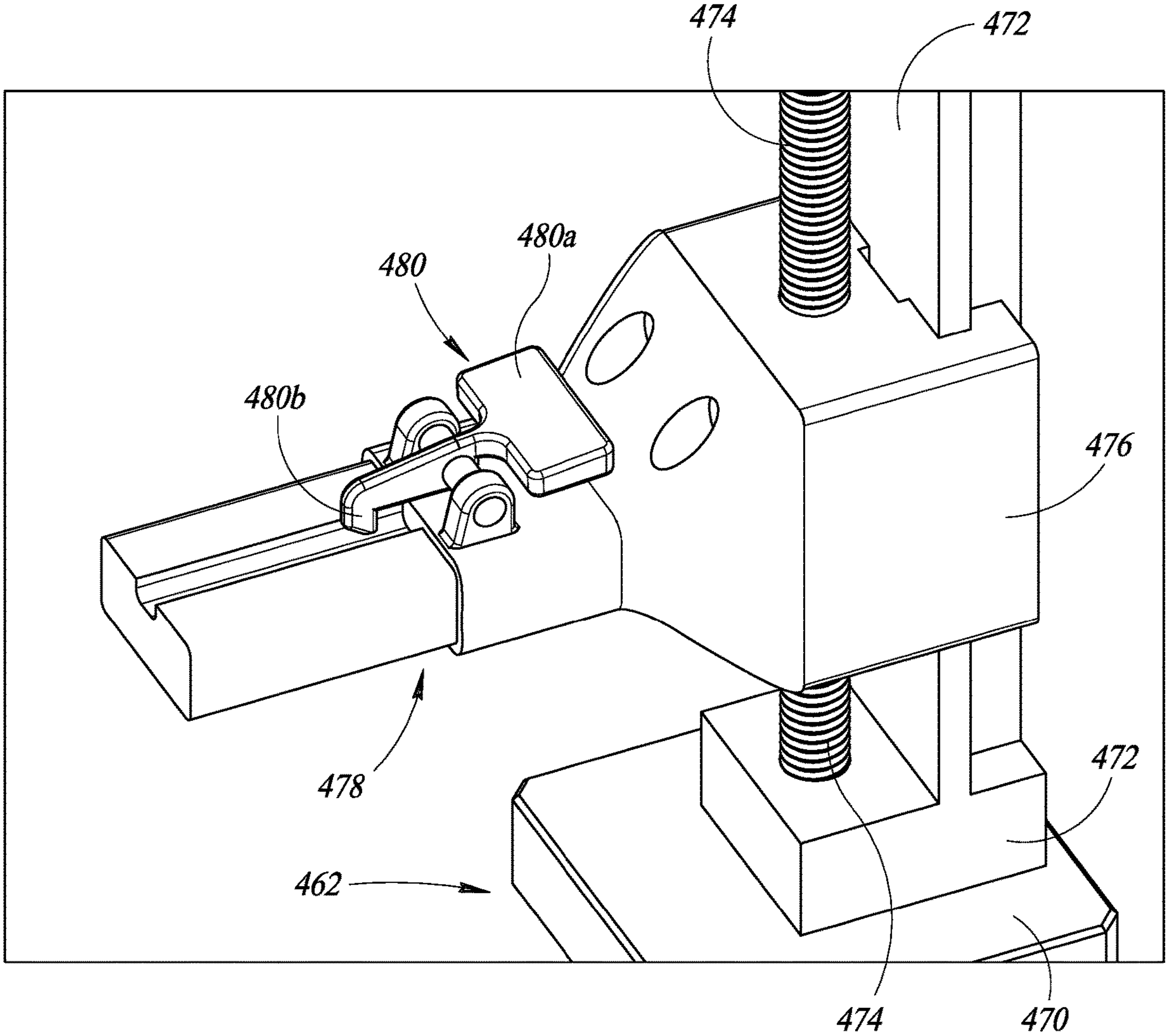
FIG. 42 illustrates a perspective view of a portion of a vertical actuation system of the microfluidic system of FIG. 22.

FIG. 42 illustrates components of the vertical actuation system 462 with other components of the system 400 removed for greater clarity. As illustrated in FIG. 42, the travelling block 476 includes a main body coupled to the guide rail 472 and to the threaded rod 474, and a bar or an arm 478 that extends forward from the main body. As illustrated in FIG. 42, the travelling block 476 also includes a latch 480 rotatably coupled to a top end surface of the arm 478. The latch 480 includes an enlarged paddle 480*a* at a first, rear end thereof and a tooth 480*b* at a second, front end thereof. The latch 480 can be biased, such as by a spring, to rotate such that the paddle 480*a* rotates away from the top end surface of the arm 478 and such that the tooth 480*b* rotates toward the top end surface of the arm 478. In operation, an operator or a technician can press downward on the paddle 480*a* to overcome the bias, rotating the paddle 480*a* toward the top end surface of the arm 478 and rotating the tooth 480*b* away from the top end surface of the arm 478.

Figure 43:
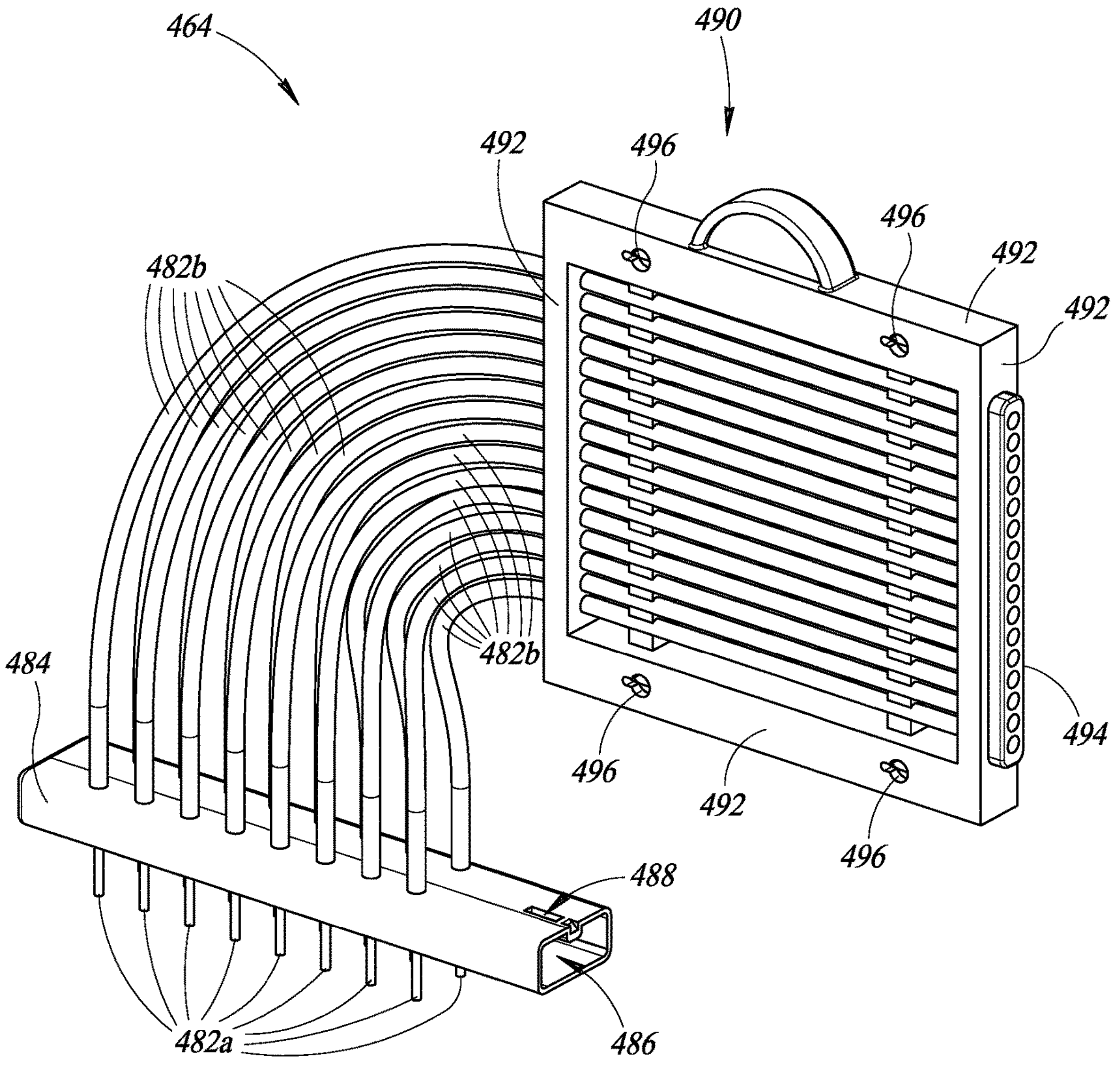
FIG. 43 illustrates a perspective view of a micropipette system of the microfluidic system of FIG. 22.

FIG. 43 illustrates the micropipette system 464 with other components of the system 400 removed for greater clarity. As illustrated in FIG. 43, the micropipette system 464 includes a plurality of individual micropipettes 482, each of which includes a respective micropipette tip 482*a* coupled to a respective pipette or micropipette (referred to herein as (micro)pipette) conduit 482*b*. As illustrated in FIG. 43, the micropipette system 464 also includes a horizontally-extending support bar or arm 484, through which each of the micropipettes 482, such as the micropipette tips 482*a* thereof, extend. The support arm 484 can maintain the micropipette tips 482*a* in a vertical orientation and can hold the micropipette tips 482*a* in an array or a grid having eight equally spaced rows extending side-to-side and two spaced-apart columns extending from front-to-back across the support arm 484.

As illustrated in FIG. 43, the support arm 484 is hollow and has an opening 486 at its rear end. The opening 486 has a size and dimensions such that the arm 478 can be inserted into the opening 486 and through the opening 486 into the hollow support arm 484. The support arm 484 also includes a recess, a depression, or a small groove 488 that extends downward into the top end surface of the support arm 484 at a rear end thereof above the opening 486. Thus, to install the micropipette system 464 onto the vertical actuation system 462, an operator or a technician can press down on the paddle 480*a* of the latch 480, insert the arm 478 into the opening 486 into the hollow support arm 484, and then release the paddle 480*a* to allow the tooth 480*b* of the latch 480 to move into and be seated within the groove 488, thereby securing and locking the support arm 484 of the micropipette system 464 to the arm 478 of the vertical actuation system 462.

Thus, movement of the travelling block 476 can induce a corresponding or a matching movement of the support arm 484, and thus of the micropipette tips 482*a*. Thus, the actuator 470 can be used as described herein to move the micropipette tips 482*a* up-and-down within the system 400. As illustrated in FIGS. 30-34, the micropipette system 464 can be installed within the system 400 such that the micropipette tips 482*a* are positioned directly above the tray 422 and/or directly above the wells 418*a* in the microfluidic chip 418 or the array of wells 430 in the microwell plate 430. The vertical actuation system 462 and its actuator 470 can be electrically or otherwise communicatively coupled to the control system, which can be configured to operate the actuator 470, such that the control system can control vertical movement of the micropipette tips 482*a* when the micropipette system 464 is installed within the system 400 and the support arm 484 is coupled to the arm 478.

FIG. 43 also illustrates that the micropipette system 464 includes a cartridge 490 including an outer frame 492, which may have an overall square or rectangular shape. As illustrated in FIG. 43, the outer frame 492 includes a male portion of a fluid connector 494, as well as a plurality of openings 496 through which protrusions or knobs of another component can be inserted to secure the cartridge 490 thereto. Ends of each of the (micro)pipette conduits 482*b* opposite the respective micropipette tips 482*a* extend into and through the cartridge 490, terminating at a respective port of the male portion of the fluid connector 494.

Figure 44:
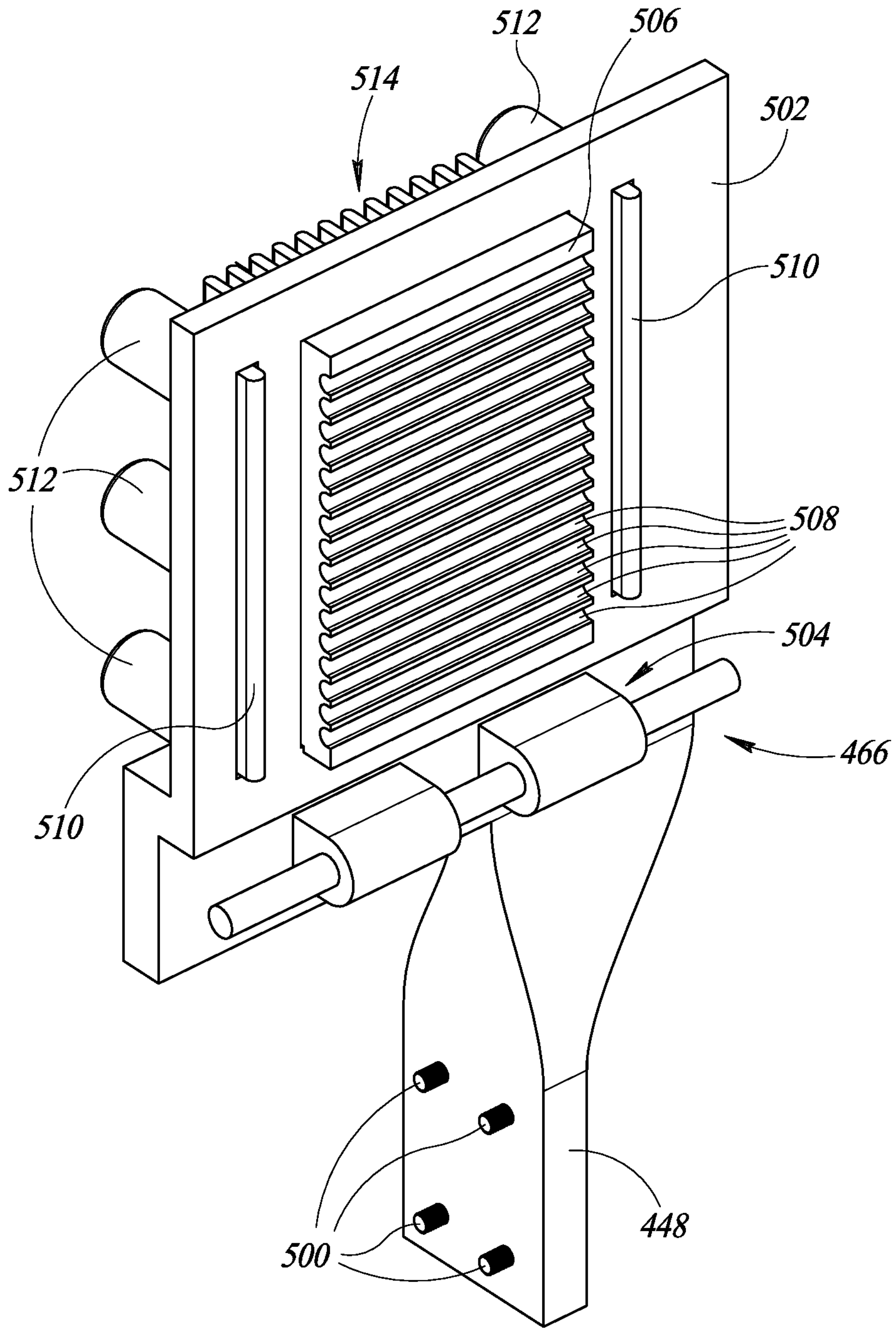
FIG. 44 illustrates a perspective view of a cradle of the microfluidic system of FIG. 22 with a hinged door thereof removed.

As illustrated in FIGS. 41 and 44, the cradle 466, which may also be referred to as a "heating assembly," includes an arm or a post or a stand 498 on which various other components of the cradle 466 may be supported. The stand 498 of the cradle 466 may be rigidly secured to, as an example, a rear end surface of the guide rail 454 of the horizontal actuation system 424, such as at a location behind the horizontal actuation system 424, including behind the tray 422, the plate 420, and/or behind the chip 418. As also illustrated in FIGS. 41 and 44, the stand 498 can be rigidly coupled and secured to the guide rail 454, such as by an adhesive or a plurality of mechanical fasteners such as screws or bolts 500.

As illustrated in FIGS. 41 and 44, the cradle 466 includes a stationary plate or sidewall 502 that extends upward and front-to-back and components 504 of a hinge located at a bottom end of the sidewall 502 and extending and facing toward the right of the sidewall 502. The cradle 466 also includes a heat transfer block 506 including sixteen individual grooves or channels 508 that extend horizontally and front-to-back therethrough, where each of the channels 508 has a semi-circular cross-sectional shape. The cradle 466 also includes a pair of bars 510 that extend to the right out of a rightward-facing surface of the sidewall 502, and that extend vertically and up-and-down along their own respective central longitudinal axes through the rightward-facing surface of the sidewall 502.

As also illustrated in FIGS. 41 and 44, the cradle 466 includes a plurality of solenoid actuators 512 that are coupled to the bars 510 and configured to actuate the bars 510 to move side-to-side and left-to-right with respect to the sidewall 502, and into or out of the rightward-facing surface of the sidewall 502. As also illustrated in FIGS. 41 and 44, the cradle 466 includes a heat sink 514 with tines or teeth facing leftward away from the heat transfer block 506. The cradle 466 may also include one or more heating systems, which may be integrated with the heat transfer block 506, integrated with the heat sink 514, or positioned between the heat transfer block 506 and the heat sink 514. In some implementations, the heating system may include a heat pump, such as a solid state heat pump or a thermoelectric heat pump, or a Peltier device, a Peltier heater, or a Peltier heat pump. The heat transfer block 506 may be made of copper or other highly-heat conductive material(s).

Figure 45:
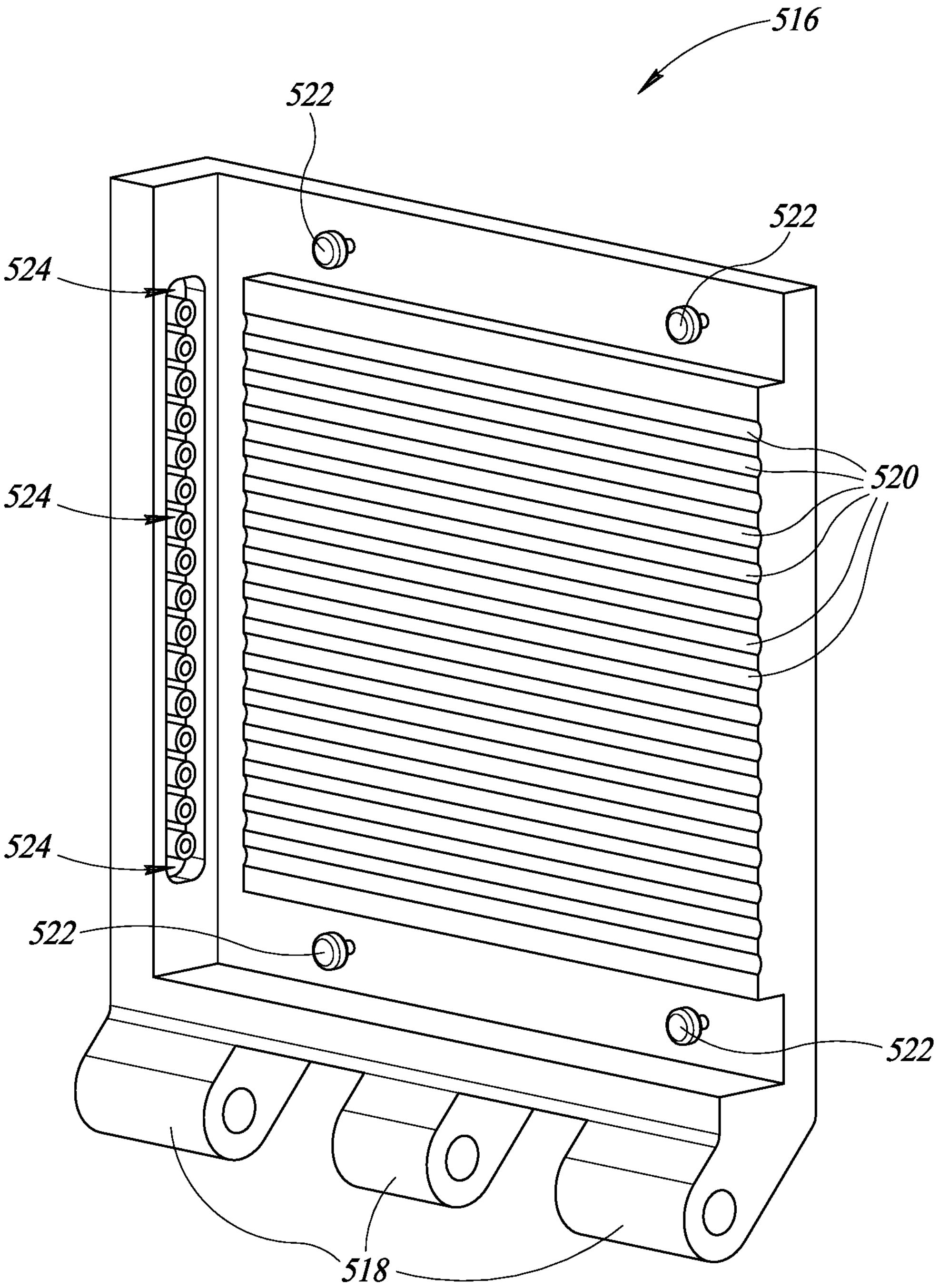
FIG. 45 illustrates a perspective view of a hinged door of the cradle of the microfluidic system of FIG. 22.

FIGS. 41 and 45 illustrate perspective views of a hinged door or a hinged sidewall 516 of the cradle 466. As illustrated in FIGS. 41 and 45, the hinged sidewall 516 extends upward and front-to-back and includes components 518 of a hinge located at a bottom end of the sidewall 516 and extending and facing toward the left of the sidewall 516. The components 518 can be coupled with the components 504 to form a complete hinge such that the hinged sidewall 516 can rotate to the left and inward toward, or to the right and outward away from, the stationary sidewall 502 about a horizontal axis that extends front-to-back through the components 504 and 518 of the hinge. The hinged sidewall 516 also includes sixteen individual grooves or channels 520 that extend horizontally and front-to-back therethrough, where each of the channels 520 has a semi-circular cross-sectional shape.

As also illustrated in FIG. 45, the hinged sidewall 516 includes a plurality of protrusions or knobs or pegs 522 having shapes corresponding to those of the openings 496 such that the knobs 522 can be inserted into the openings 496 to secure the cartridge 490 to the hinged sidewall 516. As also illustrated in FIG. 45, the hinged sidewall 516 includes a female portion of a fluid connector 524, which provides a plurality of ports, each of which can be fluidically coupled to a respective one of the ports of the male portion of the fluid connector 494. As illustrated in FIG. 41, the micropipette system 464 can be installed within the system 400 such that the cartridge 490 is positioned within the cradle 466 and between the stationary sidewall 502 and the hinged sidewall 516.

Figure 46:
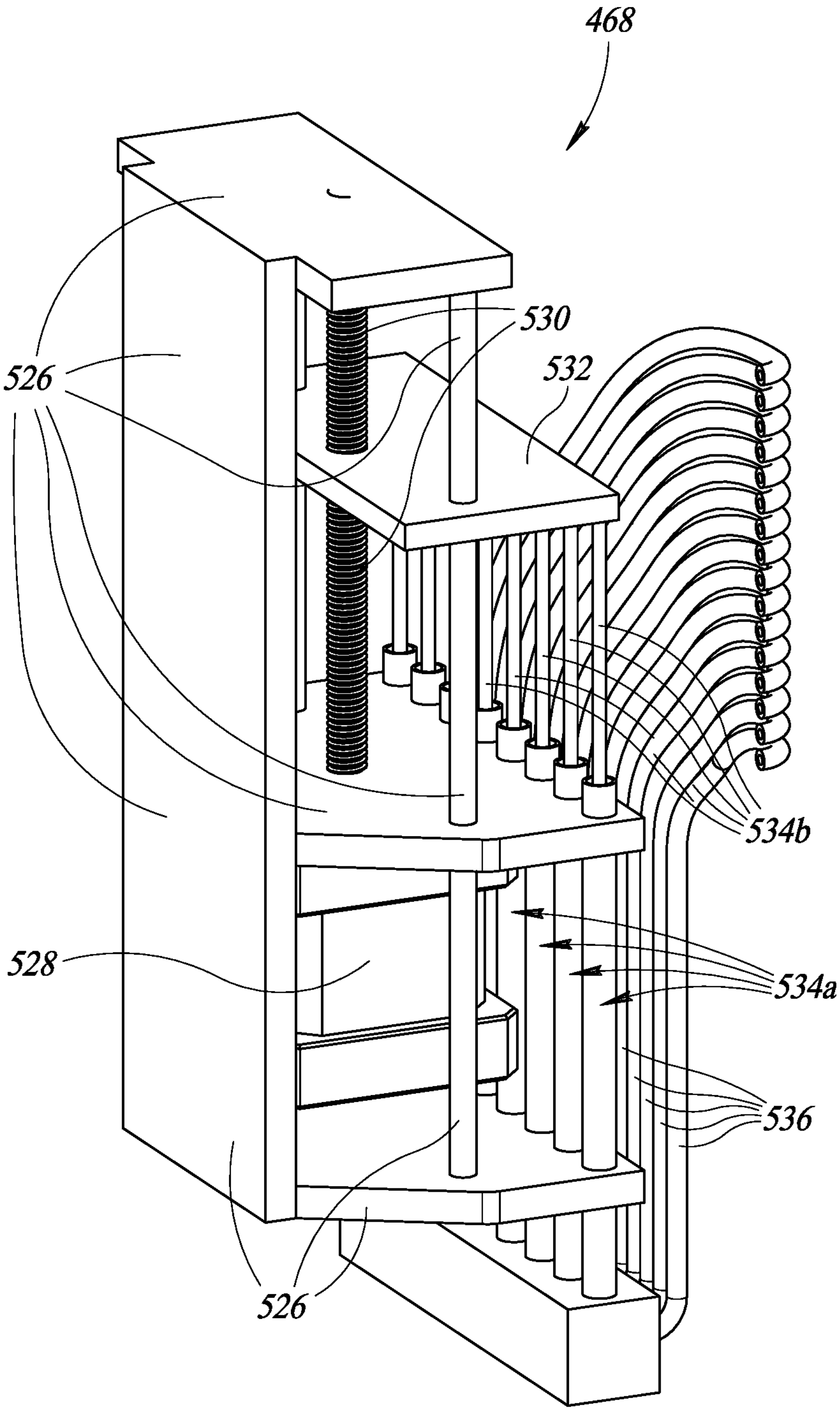
FIG. 46 illustrates a syringe pump system of the microfluidic system of FIG. 22.

FIG. 46 illustrates the pump system 468 with other components of the system 400 removed for greater clarity. The pump system 468 may be a hydraulic or a pneumatic pump system, and may also be referred to as an "air handling system." As illustrated in FIG. 46, the pump system 468 includes a stationary frame 526 to which other components of the pump system 468 can be coupled. The frame 526 may be rigidly secured to, for example, an upper surface of the bottom plate 404 of the housing 402 at a location behind the horizontal actuation system 424. As illustrated in FIG. 46, the pump system 468 also includes an electrical motor, a servo motor, or any other suitable fourth actuator 528 that can generate torque, such as from electrical power. The pump system 468 also includes a threaded rod 530 that is coupled to an output or a driven rod of the fourth actuator 528. The fourth actuator 528 can generate torque that rotates the threaded rod 530 about its own central longitudinal axis, which is a vertical axis extending up-and-down and upward from the fourth actuator 528.

The pump system 468 also includes a travelling block or plate 532, which is secured to and mounted on the frame 526 such that the travelling block 532 can travel linearly up-and-down along portions of the frame 526. For example, the travelling plate 532 may include one or more holes or openings therein, and the frame 526 may include one or more posts or columns having cross-sectional shapes corresponding to those of the openings, such that the columns can be positioned within the openings to secure the travelling plate 532 to the frame 526. The threaded rod 530 extends through a conduit or an opening extending through the travelling plate 532. In some implementations, the conduit extending through the travelling plate 532 is threaded, with threads of the conduit corresponding to the threads of the threaded rod 530, and the threads of the conduit may be engaged and interlocked with the threads of the threaded rod 530.

Thus, due to the engagement of these threads and the engagement of the travelling plate 532 with the frame 526, when the actuator 528 generates torque and induces rotation of the threaded rod 530, the rotation of the threaded rod 530 induces linear movement of the travelling plate 532 up-and-down along a height of the columns of the frame 526. By turning the threaded rod 530 in a first direction, such as clockwise or counterclockwise, the threaded rod 530 can cause the travelling plate 532 to travel in a first direction, such as up or down. By turning the threaded rod 530 in a second direction opposite to the first, such as clockwise or counterclockwise, the threaded rod 530 can cause the travelling plate 532 to travel in a second direction opposite to the first direction, such as up or down.

As illustrated in FIG. 46, the pump system 468 also includes a plurality of (e.g., eight) syringe pumps 534, each including a respective pump barrel 534*a* and a respective pump plunger 534*b* extending into the respective pump barrel 534*a*. Thus, the pump system 468 can also be referred to as an "eight channel syringe pump." Each of the pump plungers 534*b* is coupled to the travelling plate 532 such that movement of the travelling plate 532 upwards pulls the pump plungers upwards and retracts the pump plungers 534*b* out of the respective pump barrels 534*a*, and such that movement of the travelling plate 532 downwards pushes the pump plungers downwards and extends the pump plungers 534*b* into the respective pump barrels 534*a*. FIG. 46 also illustrates that the pump system 468 includes a respective pair of conduits 536 for each of the syringe pumps 534, where inlets of each pair of the conduits 536 are fluidically coupled, such as by a two-way selector valve, to an outlet of a respective one of the syringe pumps 534, and where an outlet of each of the conduits 536 is fluidically coupled to a respective one of the ports of the female portion of a fluid connector 524.

To operate the microfluidic system 400, an operator or a technician can approach the system 400 and open the housing 402 by rotating the front portion 414 of the housing 402 away from the rest of the housing 402. The technician can then install the microfluidic chip 418 and the microwell plate 420 by positioning the microfluidic chip 418 into the cavity 426 in the microwell plate 420 and then securing the microwell plate 420 to the tray 422 by sliding the protrusions 434 downward and then horizontally along and through the grooves 442. The technician can then load biological samples and other materials, such as PCR reagents but depending on the processing to be done, into the array of microwells 430 of the microwell plate 420 and/or into the wells 418*a* of the microfluidic chip 418. In some implementations, these materials can include materials to facilitate qPCR, gel electrophoresis, or any of the other processing techniques described herein. In some specific implementations, these materials can include an RNA polymerase or a DNA polymerase, and may include any of various DNA polymerases of thermophilic organisms used in PCR, which may be referred to as "TAQ polymerases."

The technician can then install the micropipette system 464. Installing the micropipette system 464 can include rotating the hinged sidewall 516 of the cradle 466 outward away from the stationary sidewall 502, then securing the cartridge 490 to the hinged sidewall 516 by inserting the knobs 522 of the sidewall 502 into the openings 496 in the cartridge 490 and by securing the male portion of the fluid connector 494, including the fluid ports thereof, within the female portion of the fluid connector 524, including the fluid ports thereof, and then rotating the hinged sidewall 516 of the cradle 466 inward toward the stationary sidewall 502 to secure the cartridge between the stationary sidewall 502 and the hinged sidewall 516 such that the (micro)pipette conduits 482*b* are cradled between the grooves 508 of the heat transfer block 506 and the grooves 520 of the hinged sidewall 516. Installing the micropipette system 464 can also include pressing down on the paddle 480*a* of the latch 480, inserting the arm 478 into the opening 486 into the hollow support arm 484, and then releasing the paddle 480*a* to allow the tooth 480*b* of the latch 480 to move into and be seated within the groove 488, thereby securing and locking the support arm 484 of the micropipette system 464 to the arm 478 of the vertical actuation system 462.

Once these actions have been completed, the technician can close the system 400 by rotating the front portion 414 of the housing 402 toward the rest of the housing 402. The technician can then press or push the button 416, such as exactly and only once, to initiate operation of the microfluidic system 400 and processing of the biological samples or other materials therein. In some implementations, the operator or technician may also press the button 416 to stop or halt operation of the microfluidic system 400 prior to completion of the processing, for example, in case an emergency or other unforeseen circumstance or situation arises.

Once the technician has pressed the button 416 to initiate operation of the microfluidic system 400, the microfluidic system 400 can automatically control movement and operation of the components therein to process the materials in specified ways. For example, in some implementations, the system 400 can use the horizontal actuation system 424 to move the tray 422 horizontally until the micropipette tips 482*a* are located directly above microwells 430 in the microwell plate 420 that contain desired materials. The system 400 can then use the vertical actuation system 462 to move the micropipette tips 482*a* downward until they are located within the desired materials in the microwells 430 of the microwell plate 420. The system 400 can then use the fourth actuator 528 to drive the syringe pumps 534 to draw the desired materials up into the (micro)pipette conduits 482*b*. In general, operation of the fourth actuator 528 in this manner drives each of the eight syringe pumps 534 in unison.

The system 400 can then use the vertical actuation system 462 to move the micropipette tips 482*a* upward until they are located above the microwell plate 420. The system 400 can then use the horizontal actuation system 424 to move the tray 422 horizontally until the micropipette tips 482*a* are located directly above wells 418*a* in the microfluidic chip 418 where processing of the materials is to begin. The system 400 can then use the vertical actuation system 462 to move the micropipette tips 482*a* downward until they are located within the desired wells 418*a* of the microfluidic chip 418. The system 400 can then use the fourth actuator 528 to drive the syringe pumps 534 to expel the materials out of the (micro)pipette conduits 482*b* into the wells 418*a*. This process can be repeated to move as many materials as desired from the microwells 430 of the microwell plate 420 into the wells 418*a* in the microfluidic chip 418.

Once the materials have been supplied to the wells 418*a* in this manner, the materials can undergo various processing steps within the microfluidic chip 418, such as to separate or remove contaminants from such materials, such as in accordance with the description of such processing elsewhere herein. During such processing, the electrically conductive leads 428 can be energized to create electric field(s), and/or the magnet 450 can be moved to provide a magnetic field, that interact with the materials being processed, thereby affecting their behavior within the microfluidic chip 418 and assisting in the processing of those materials in the microfluidic chip 418. Once such processing is completed, a quality control check may be performed to confirm that sufficient material is available for further processing, such as for use in PCR processing. Such a quality control check could be done inside or outside of the system 400.

The system 400 can then use the horizontal actuation system 424 to move the tray 422 horizontally until the micropipette tips 482*a* are located directly above wells 418*a* in the microfluidic chip 418 that contain desired materials. The system 400 can then use the vertical actuation system 462 to move the micropipette tips 482*a* downward until they are located within the desired materials in the wells 418*a* of the microfluidic chip 418. The system 400 can then use the fourth actuator 528 to drive the syringe pumps 534 to draw the desired materials up into the (micro)pipette conduits 482*b*.

The system 400 can then use the vertical actuation system 462 to move the micropipette tips 482*a* upward until they are located above the microfluidic chip 418. The system 400 can then use the horizontal actuation system 424 to move the tray 422 horizontally until the micropipette tips 482*a* are located directly above microwells 430 in the microwell plate 420 where additional desired materials, such as PCR reagents, are located. The system 400 can then use the vertical actuation system 462 to move the micropipette tips 482*a* downward until they are located within the desired microwells 430 of the microwell plate 420. The system 400 can then use the fourth actuator 528 to drive the syringe pumps 534 to draw the desired materials such as PCR reagents up into the (micro)pipette conduits 482*b*, such as until the desired materials are mixed with one another inside the (micro)pipette conduits 482*b* and located in the portions of the (micro)pipette conduits 482*b* inside the cartridge 490.

Once the desired materials are located within the portions of the (micro)pipette conduits 482*b* inside the cartridge 490, the solenoid actuators can be used to move the bars 510 to the right out of the rightward-facing surface of the sidewall

502, and toward the hinged sidewall 516, until the bars 510 pinch each of the (micro)pipette conduits 482*b* in two locations to prevent any materials escaping from the portions of the (micro)pipette conduits 482*b* located inside the cartridge 490. The heater within the cradle 466 can then be used to heat the materials held within the portions of the (micro)pipette conduits 482*b* inside the cartridge 490 to facilitate chemical reactions or other processing steps therein. In some cases, this includes using the heater to generate a constant heat flow to the (micro)pipette conduits 482*b*, while in other cases, this includes cycling the heater to provide a cyclical heat flow to the (micro)pipette conduits 482*b*. In some implementations, the (micro)pipette conduits 482*b* are made of a heat conductive plastic to conduct the heat to the materials more effectively.

As an example, the heat can facilitate a PCR reaction taking place within the portions of the (micro)pipette conduits 482*b* inside the cartridge 490. Once this processing is completed, the heater within the cradle 466 can then be turned off to stop heating the materials held within the portions of the (micro)pipette conduits 482*b* inside the cartridge 490, and the solenoid actuators can be used to move the bars 510 to the left into the rightward-facing surface of the sidewall 502, and away from the hinged sidewall 516, until the bars 510 no longer pinch the (micro) pipette conduits 482*b*. Once such processing is completed, a quality control check may be performed to confirm that the processing, such as the PCR processing, was successful or met certain performance standards. Such a quality control check could be done inside or outside of the system 400.

The system 400 can then use the horizontal actuation system 424 to move the tray 422 horizontally until the micropipette tips 482*a* are located directly above wells 430 in the microfluidic plate 420. The system 400 can then use the vertical actuation system 462 to move the micropipette tips 482*a* downward until they are located within the desired wells 430 in the microwell plate 430. The system 400 can then use the fourth actuator 528 to drive the syringe pumps 534 to expel the materials out of the (micro)pipette conduits 482*b* into the wells 430.

Once such processing is complete, the technician can open the housing by rotating the front portion 414 of the housing 402 away from the rest of the housing 402. The technician can then remove the micropipette system 464. Removing the micropipette system 464 can include rotating the hinged sidewall 516 of the cradle 466 outward away from the stationary sidewall 502, then removing the cartridge 490 from the hinged sidewall 516 by moving the knobs 522 of the sidewall 502 out of the openings 496 in the cartridge 490 and by removing the male portion of the fluid connector 494, including the fluid ports thereof, from the female portion of the fluid connector 524, including the fluid ports thereof. Removing the micropipette system 464 can also include pressing down on the paddle 480*a* of the latch 480, removing the arm 478 from the opening 486 and the hollow support arm 484, and then releasing the paddle 480*a*.

The technician can then also remove the microfluidic chip 418 and the microwell plate 420 from the tray 422 by sliding the protrusions 434 horizontally and then upward along and through the grooves 442. The technician can then remove the processed materials from the wells 430 in the microwell plate 420. Once these materials have been removed and stored elsewhere, the micropipette system 464, the microwell plate 420, and the microfluidic chip 418 can be discarded as waste. Subsequent processing can use a new micropipette system 464, a new microwell plate 420, and a new microfluidic chip 418. In some implementations, the microfluidic chip 418, the microwell plate 420, and/or any other components of the system 400 described herein may include an RFID chip or tag to assist in identifying specific components and tracking their locations within a larger collection of such components.

The processing described herein proceeds by moving materials from the microwell plate 430 to the microfluidic chip 418, then from the microfluidic chip 418 to the cradle 466, then from the cradle 466 back to the microwell plate 430. Such processing can serve to remove contaminants from a biological sample and desired components thereof, such as DNA, RNA, mRNA, or various proteins, including various amino acid-based proteins, and then perform PCR on the biological sample. In alternative implementations, however, processing can proceed by moving materials from any component(s) to any other component(s) any number of times, depending on the actions called for by the desired processing. In one example of an alternative implementation, the processing described herein may proceed by moving materials from the microwell plate 430 to the cradle 466, then from the cradle 466 to the microfluidic chip 418, then from the microfluidic chip 418 back to the microwell plate 420. Such processing can serve to perform PCR on a biological sample and desired components thereof, such as DNA, RNA, mRNA, or various proteins, including various amino acid-based proteins, and then remove contaminants from the biological sample.

Figure 47:
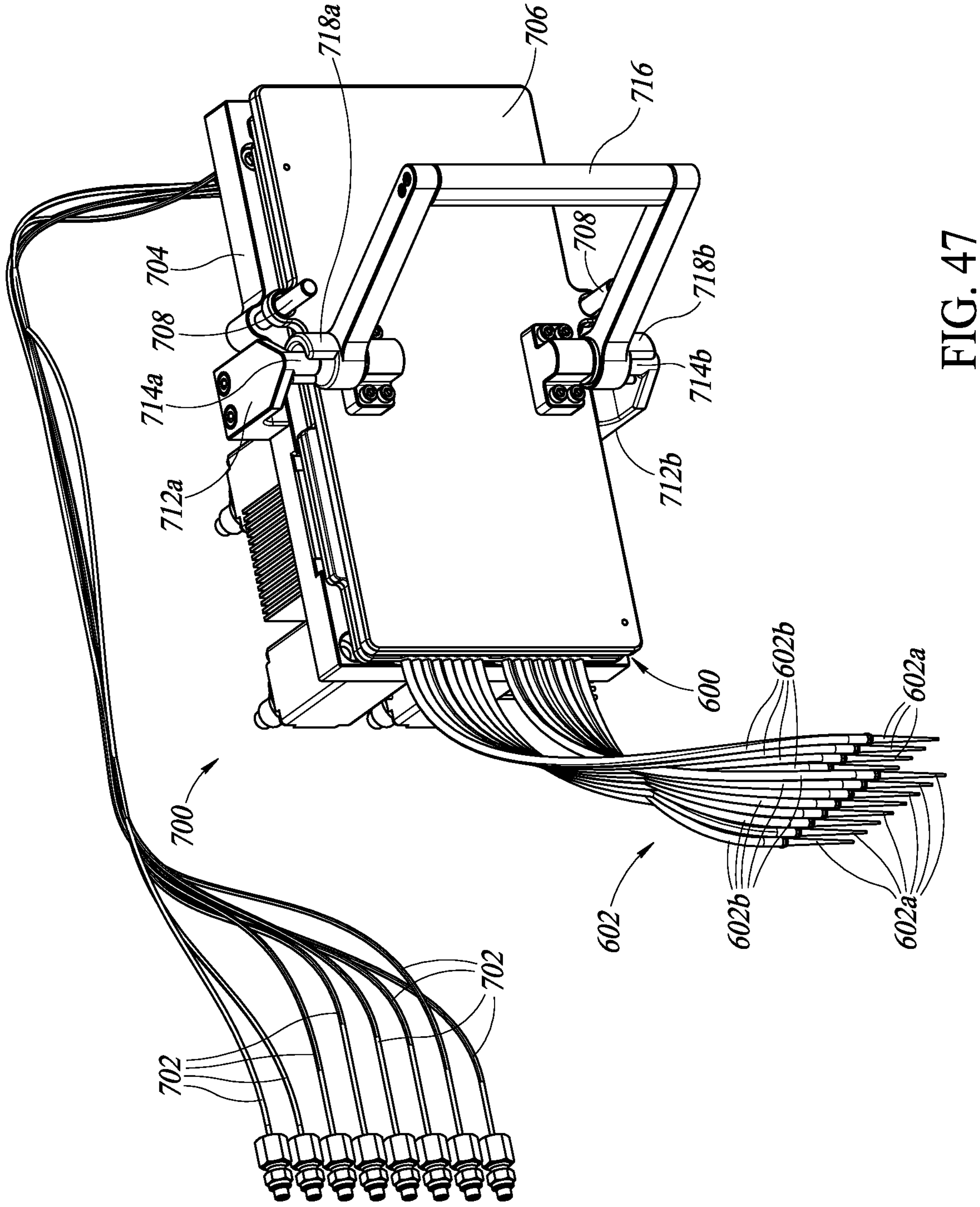
FIG. 47 illustrates a front, left-side, and top perspective view of another system, including a micropipette system and a cradle, that can be used with the microfluidic system of FIG. 22.
Figure 48:
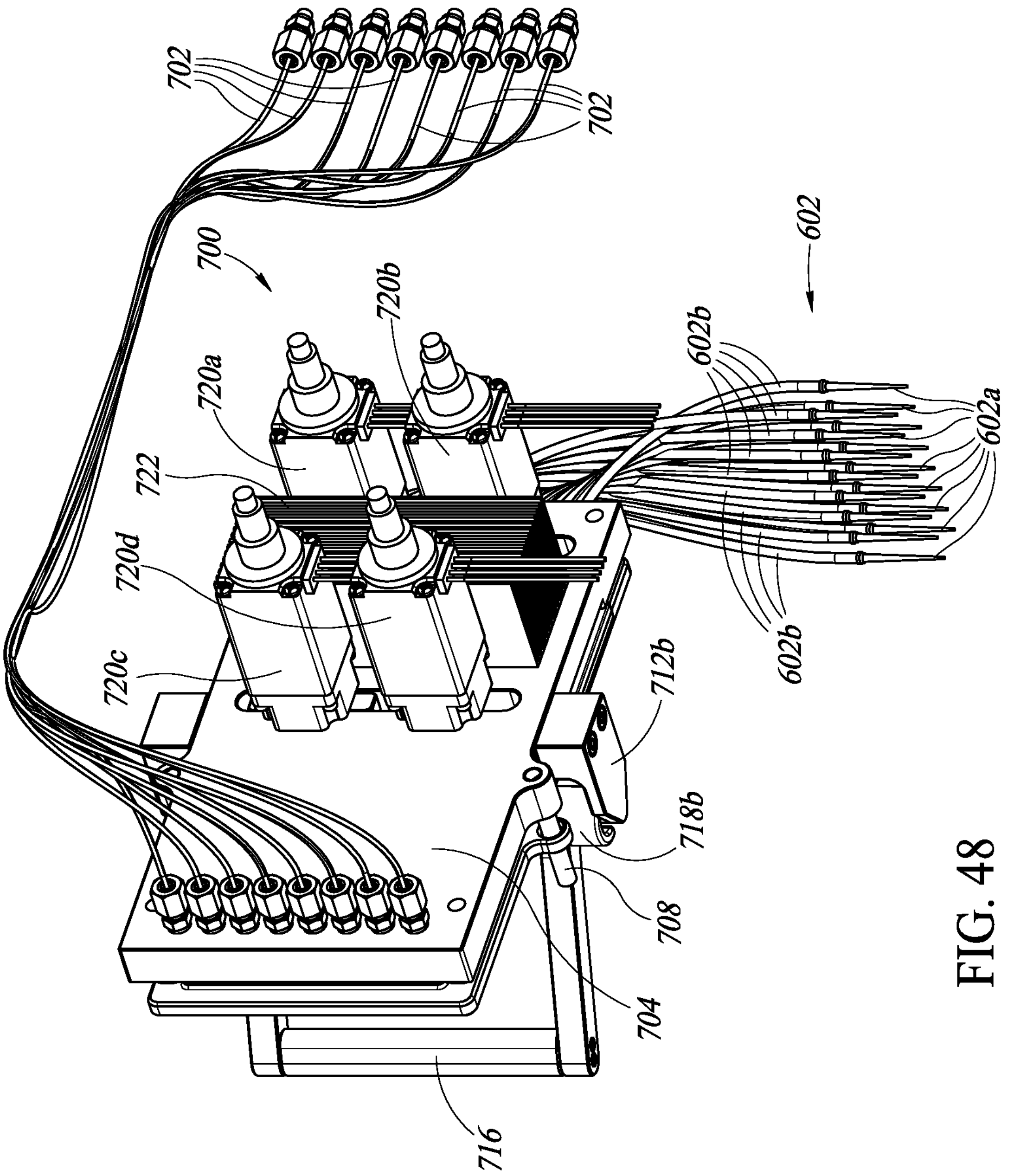
FIG. 48 illustrates a rear, right-side, and bottom perspective view of the system of FIG. 47.

FIGS. 47-55 illustrate components of another system, including another pipette or micropipette (referred to herein as (micro)pipette) system 600 and another cradle 700, that can be used with the microfluidic system 400 of FIG. 22, or in combination with any of the other features, components, systems, and/or methods described herein. In particular, FIG. 47 illustrates a front, left-side, and top perspective view of the (micro)pipette system 600 and cradle 700 and FIG. 48 illustrates a rear, right-side, and bottom perspective view of the (micro)pipette system 600 and the cradle 700. As illustrated in FIGS. 47 and 48, the (micro)pipette system 600 includes a plurality of individual pipettes or micropipettes (referred to herein as (micro)pipettes) 602, each of which includes a respective (micro)pipette tip 602*a* coupled to a respective (micro)pipette conduit 602*b*. As also illustrated in FIGS. 47 and 48, the cradle 700 includes a plurality of fluid conduits 702. The (micro)pipette system 600 includes a cartridge 604 located inside the cradle 700 that includes fluidic components that fluidically couple the (micro)pipettes 602 to the fluid conduits 702.

In some implementations, the (micro)pipette system 600 can include or be used with any of the components or features described herein for the micropipette system 464, and can be used in the ways, actions, or methods described herein with respect to the micropipette system 464. In some implementations, the (micro)pipettes 602 can include or be used with any of the components or features described herein for the micropipettes 482, and can be used in the ways, actions, or methods described herein with respect to the micropipettes 482. In some implementations, the fluid conduits 702 can include or be used with any of the components or features described herein for the conduits 536 and can be used in the ways, actions, or methods described herein with respect to the conduits 536. In some implementations, the cartridge 604 can include or be used with any of the components or features described herein for the cartridge 490, and can be used in the ways, actions, or methods described herein with respect to the cartridge 490.

As illustrated in FIGS. 47 and 48, the exemplary (micro) pipette system 600 includes exactly sixteen of the (micro)

pipettes 602 and the cradle 700 includes exactly eight of the fluid conduits 702. In different implementations, however, the (micro)pipette system 600 may be provided with any suitable number of (micro)pipettes 602 and the cradle 700 may be provided with any suitable number of fluid conduits 702. In some specific implementations, the number of (micro)pipettes 602 is twice the number of fluid conduits 702.

FIGS. 47 and 48 also illustrate that the cradle 700 includes a fixed or stationary rear portion, plate, or wall 704 and a movable, removable front portion, plate, wall, or door 706. As illustrated in FIGS. 47 and 48, the rear portion 704 and the front portion 706 extend generally parallel to one another, and are proximate one another but spaced apart from one another such that a gap is defined between them. In use, the cartridge 604 is positioned and secured in the gap between the rear portion 704 and the front portion 706. As also illustrated in FIGS. 47 and 48, the rear portion 704 includes a pair of guide rods or guide pins 708 that extend forward from the rear portion 704 toward and through the front portion 706, and the front portion 706 has a complementary pair of apertures 710 (FIG. 49) configured to receive, such as snugly receive, the guide pins 708 to guide movement of the front portion 706 toward and away from the rear portion 704.

In some implementations, the cradle 700 can include or be used with any of the components or features described herein for the cradle 466, and can be used in the ways, actions, or methods described herein with respect to the cradle 466. In some implementations, the rear portion 704 can include or be used with any of the components or features described herein for the stationary sidewall 502, and can be used in the ways, actions, or methods described herein with respect to the stationary sidewall 502. In some implementations, the front portion 706 can include or be used with any of the components or features described herein for the hinged sidewall 516, and can be used in the ways, actions, or methods described herein with respect to the hinged sidewall 516.

As further illustrated in FIGS. 47 and 48, the rear portion 704 includes a top flange 712*a* that extends forward from a top end of the rear portion 704 forward toward, above, and past the front portion 706, and a bottom flange 712*b* that extends forward from a bottom end of the rear portion 704 forward toward, below, and past the front portion 706. The top flange 712*a* is coupled to a vertically-extending rod 714*a* that extends downward from a bottom surface of the top flange 712*a*, and the bottom flange 712*b* is coupled to a vertically-extending rod 714*b* that extends upward from a top surface of the bottom flange 712*b*. The front portion 706 includes a handle 716 that is supported and hinged thereon to rotate about a vertical axis aligned with the vertically extending rods 714*a*, 714*b*. As illustrated in FIGS. 47 and 48, the handle 716 includes an upper semi-circular or semi-cylindrical coupling element 718*a* engaged with the vertically extending rod 714*a* and a lower semi-circular or semi-cylindrical coupling element 718*b* engaged with the vertically extending rod 714*b*.

To assemble the cradle 700, the apertures 710 (FIG. 49) of the front portion 706 can be moved along the guide rods 708 of the rear portion 704 toward the rear portion 704, and the handle 716 can then be rotated in a first direction, such as counter-clockwise when viewed from above, to engage the coupling elements 718*a*, 718*b* with the vertically extending rods 714*a*, 714*b* and secure the front portion 706 to the rear portion 704. To disassemble the cradle 700, the handle 716 can be rotated in a second direction opposite to the first, such as clockwise when viewed from above, to disengage the coupling elements 718*a*, 718*b* from the vertically extending rods 714*a*, 714*b* and release the front portion 706 from the rear portion 704, and the apertures 710 (FIG. 49) of the front portion 706 can then be moved along the guide rods 708 of the rear portion 704 away from the rear portion 704.

As further illustrated in FIGS. 47 and 48, the cradle 700 includes a first, upper left solenoid actuator 720*a*, a second, lower left solenoid actuator 720*b*, a third, upper right solenoid actuator 720*c*, and a fourth, lower right solenoid actuator 720*d*. The solenoid actuators 720*a*, 720*b*, 720*c*, and 720*d* are configured to actuate valves of the cradle 700, as described in greater detail elsewhere herein. As also illustrated in FIGS. 47 and 48, the cradle 700 includes a heat sink 722 with tines or teeth facing rearward away from the rear portion 704 of the cradle 700.

Figure 49:
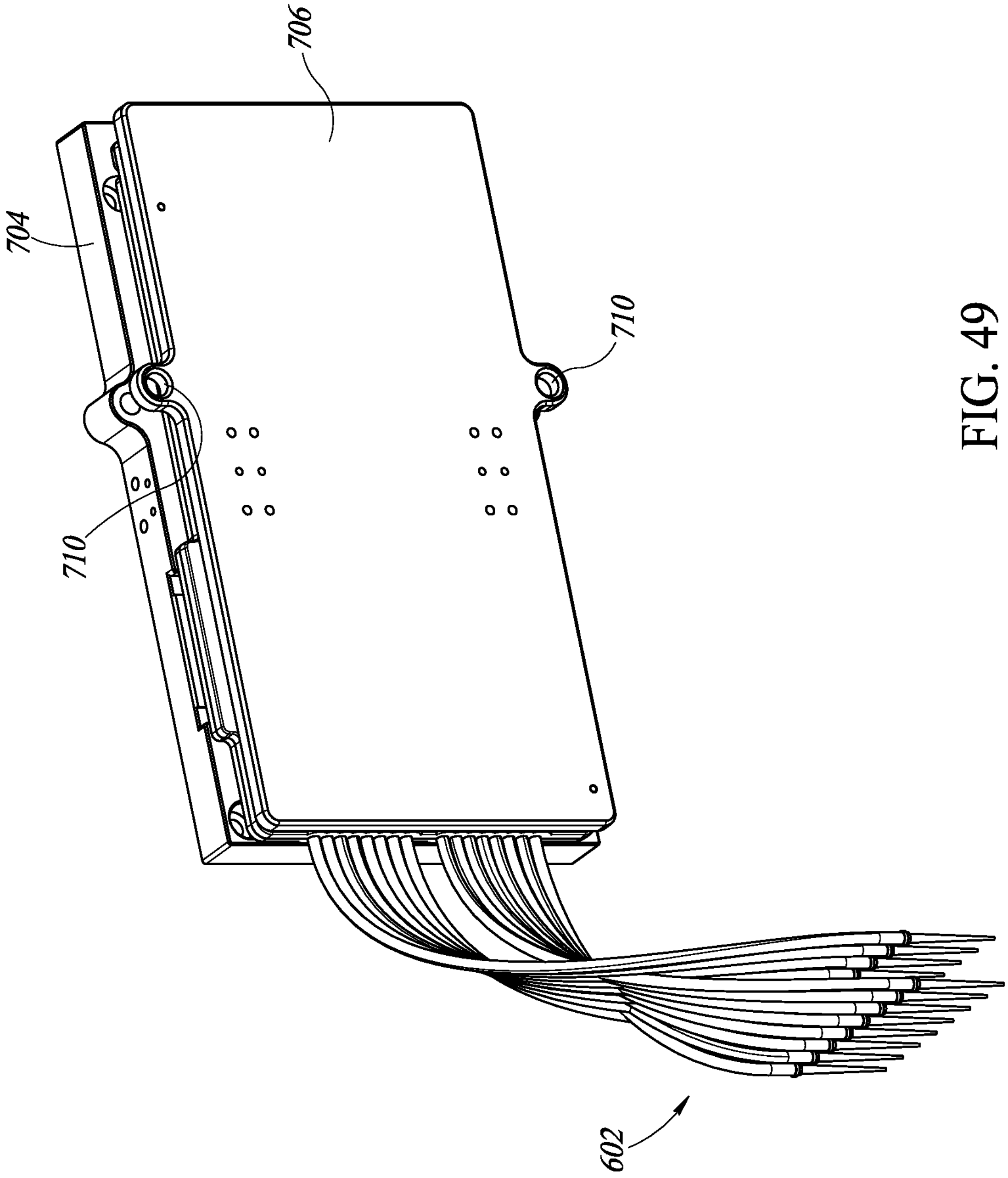
FIG. 49 illustrates a front, left-side, and top perspective view of the system of FIG. 47 with fluid conduits, solenoid actuators, a heat sink, and a handle thereof removed.
Figure 50:
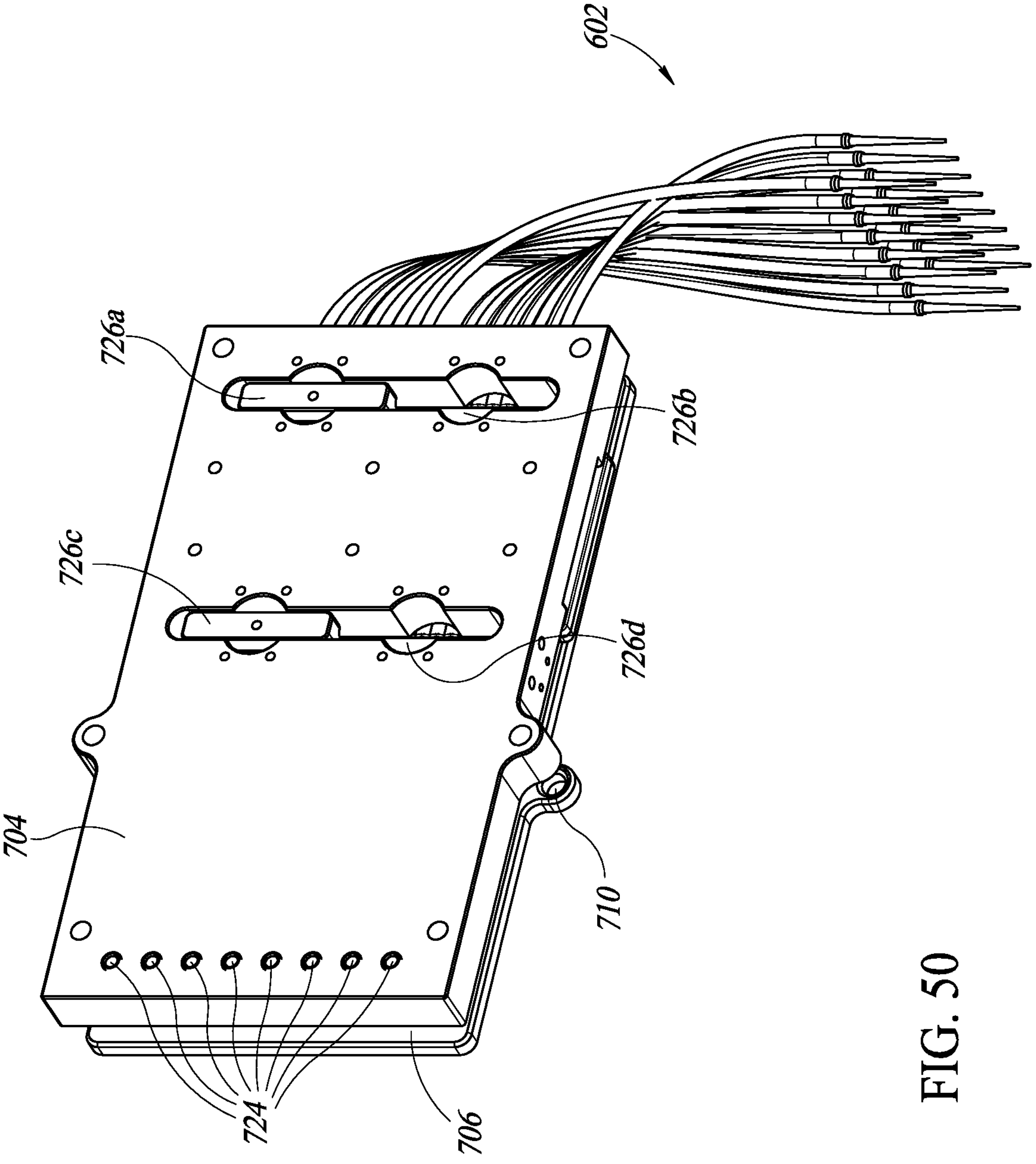
FIG. 50 illustrates a rear, right-side, and bottom perspective view of the system of FIG. 47 with fluid conduits, solenoid actuators, a heat sink, and a handle thereof removed.

FIG. 49 illustrates a front, left-side, and top perspective view of the (micro)pipette system 600 and cradle 700 with the fluid conduits 702, solenoid actuators 720, heat sink 722, and handle 716 removed, and FIG. 50 illustrates a rear, right-side, and bottom perspective view of the (micro) pipette system 600 and cradle 700 with the fluid conduits 702, solenoid actuators 720, heat sink 722, and handle 716 removed. FIG. 50 illustrates that the rear portion 704 includes a plurality of (e.g., eight) fluid ports 724 to which the fluid conduits 702 are connected and through which the fluid conduits 702 supply fluids to the cartridge 604 within the cradle 700. FIG. 50 also illustrates that the rear portion 704 includes a plurality of (e.g., four) apertures or openings through which a corresponding plurality of (e.g., four) valves 726 extend. Each of the valves 726 may include a bar that extends forward out of a front face of the rear portion 704, and that extends vertically and up-and-down along its own respective longitudinal axis through the rear portion 704.

In use, each of the solenoid actuators 720 is coupled to a respective one of the valves 726 and is configured to actuate the respective valve 726 to move forward or rearward through the respective aperture in the rear portion 704 with respect to the rear portion 704, the front portion 706, and the cartridge 604. In particular, the first, upper left solenoid actuator 720*a* is configured to actuate a first, upper left valve 726*a*, the second, lower left solenoid actuator 720*b* is configured to actuate a second, lower left valve 726*b*, the third, upper right solenoid actuator 720*c* is configured to actuate a third, upper right valve 726*c*, and the fourth, lower right solenoid actuator 720*d* is configured to actuate a fourth, lower right valve 726*d*.

Figure 51:
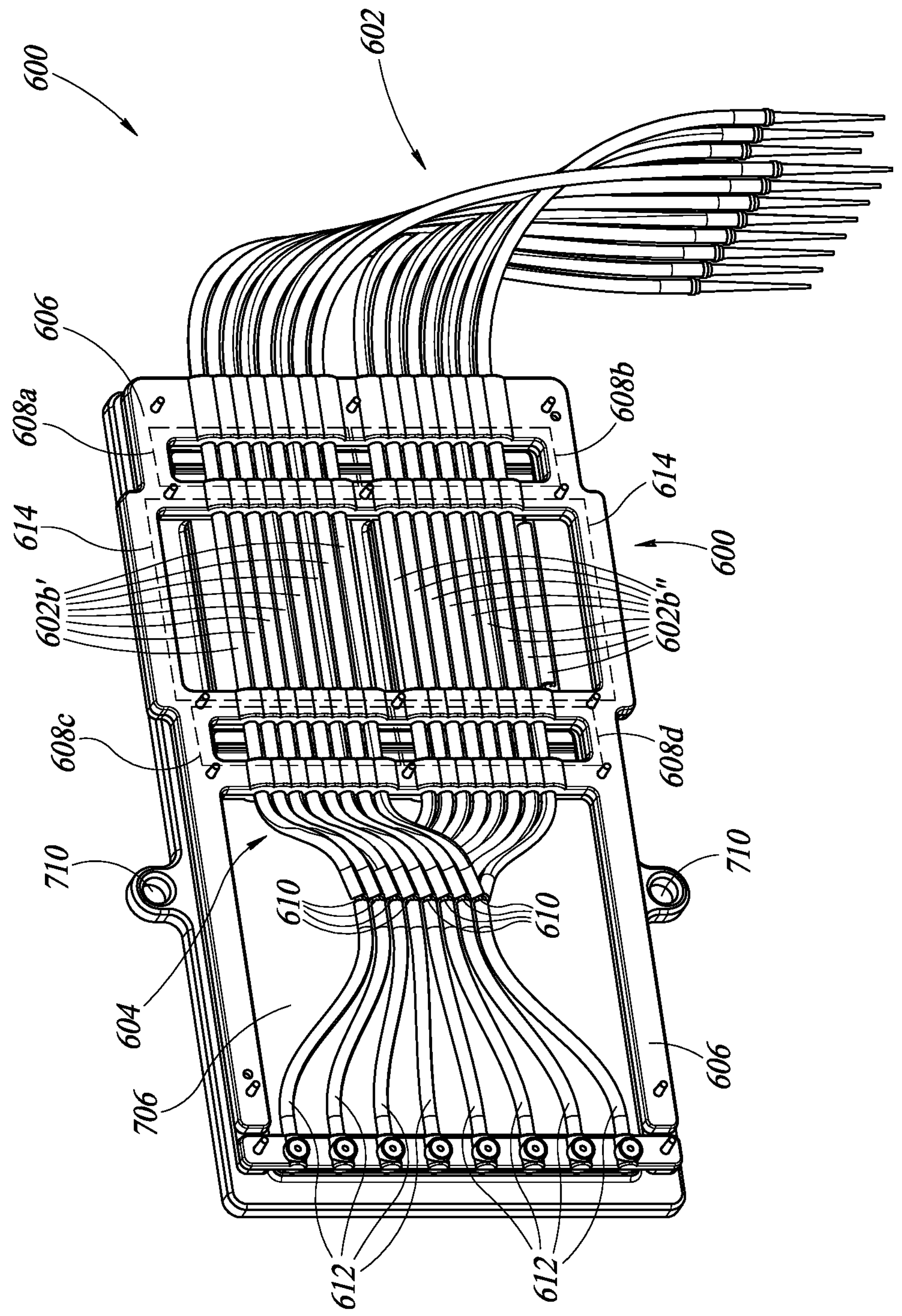
FIG. 51 illustrates the system of FIG. 47 as illustrated in FIG. 50 with a rear portion of the cradle removed to reveal additional components.

FIG. 51 illustrates the (micro)pipette system 600 and the cradle 700 as illustrated in FIG. 50 with the rear portion 704 of the cradle 700 removed. FIG. 51 illustrates the cartridge 604, which includes an outer frame 606 that holds a plurality of fluidic components together and in position within the cradle 700. For example, the (micro)pipette conduits 602*b* extend into and are held and supported within the cartridge 604 by the outer frame 606. As illustrated in FIG. 51, the (micro)pipette conduits 602*b* are grouped into two groups of (micro)pipette conduits 602*b*' and 602*b*" of equal number, with a first one of the two sets positioned above a second one of the two sets. In particular, the sixteen (micro)pipette conduits 602*b* are grouped into two groups of eight adjacent (micro)pipette conduits 602*b*.

As further illustrated in FIG. 51, each of the (micro) pipette conduits 602*b* is exposed at two different locations, thereby forming four distinct sealing zones: a first, upper left sealing zone 608*a* wherein the first one of the two sets of (micro)pipette conduits 602*b*' can be sealed by the valve 726*a* (FIG. 50) proximate the (micro)pipette tips 602*a*, a second, lower left sealing zone 608*b* wherein the second one of the two sets of (micro)pipette conduits 602*b*" can be sealed by the valve 726*b* (FIG. 50) proximate the (micro) pipette tips 602*a*, a third, upper right sealing zone 608*c* wherein the first one of the two sets of (micro)pipette conduits 602*b*' can be sealed by the valve 726*c* (FIG. 50) proximate the fluid conduits 702, and a fourth, lower right sealing zone 608*d* wherein the second one of the two sets of (micro)pipette conduits 602*b*" can be sealed by the valve 726*d* (FIG. 50) proximate the fluid conduits 702. In use, each of the valves 726 can engage with the (micro)pipette conduits 602*b* in a respective one of the sealing zones 608 to seal the (micro)pipette conduits 602*b* therein.

As also illustrated in FIG. 51, the cartridge 604 includes a plurality of (e.g., eight) three-way fluid valves or connectors 610. Each of the three-way fluid connectors 610 is coupled to a respective one of the first set of (micro)pipette conduits 602*b*', to a respective one of the second set of (micro)pipette conduits 602*b*", and to a respective feeder conduit 612, such that each of the sealing zones 608 is located, such as mechanically and/or fluidically, between the (micro)pipette tips 602*a* and the fluid connectors 610. In use, each of the feeder conduits 612 is fluidically coupled to one of the fluid ports 724. Thus, in use, a fluid pressure such as an air pressure provided by a pump system such as pump system 468 can be supplied directly and simultaneously to one of the first set of (micro)pipette conduits 602*b*' and one of the second set of (micro)pipette conduits 602*b*". As further illustrated in FIG. 51, each of the (micro)pipette conduits 602*b* is exposed from the frame 606 within a heating zone 614 located mechanically and/or fluidically between the first and third sealing zones 608*a*, 608*c* and mechanically and/or fluidically between the second and fourth sealing zones 608*b*, 608*d*.

Figure 52:
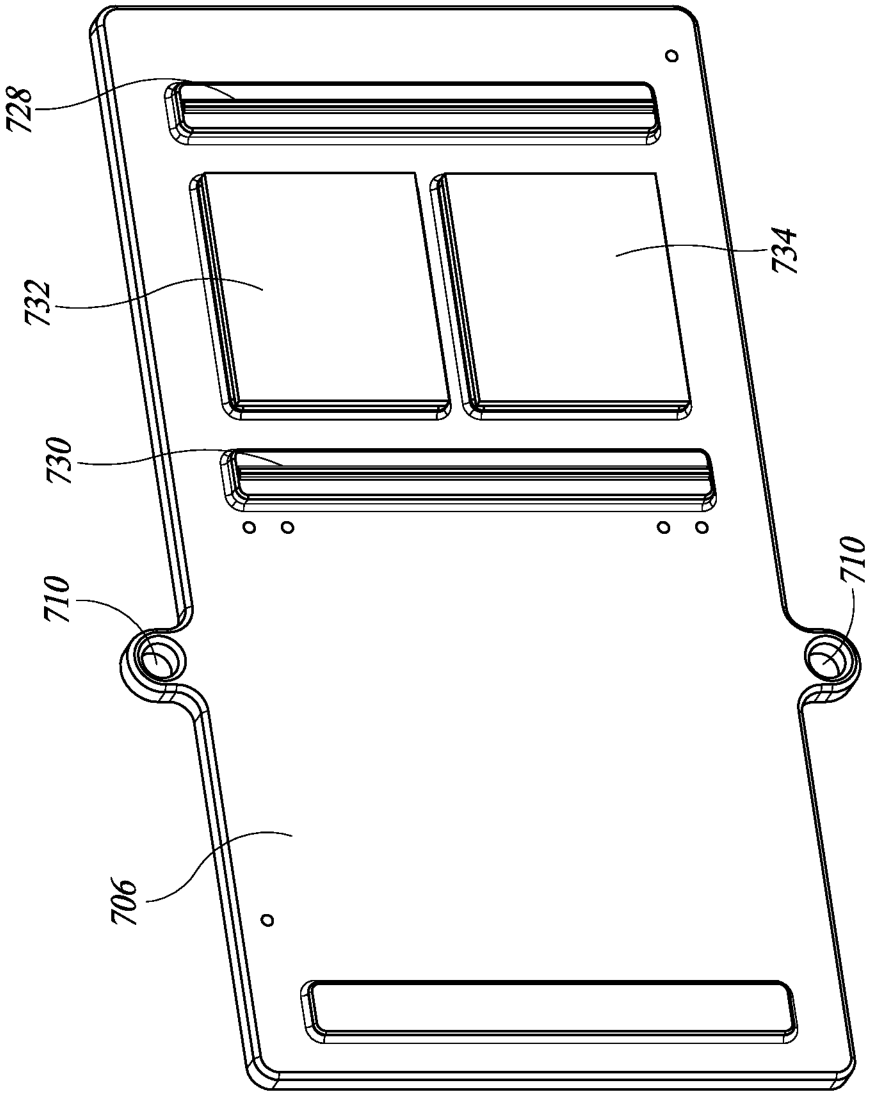
FIG. 52 illustrates the system of FIG. 47 as illustrated in FIG. 51 with the micropipette system removed to reveal additional components.

FIG. 52 illustrates the components of FIG. 51 with the (micro)pipette system 600 removed. As illustrated in FIG. 52, the front portion 706 of the cradle 700 includes a first vertically extending protrusion, ridge, or bar 728 positioned and dimensioned to engage with the (micro)pipette conduits 602*b* within the first and second sealing zones 608*a*, 608*b*, and a second vertically extending protrusion, ridge, or bar 730 positioned and dimensioned to engage with the (micro) pipette conduits 602*b* within the third and fourth sealing zones 608*c*, 608*d*. In some implementations, when the solenoid actuators 720 are used to actuate movement of the valves 726 toward the front portion 706, the valves can be actuated to move directly toward the bars 728 and 730 so as to pinch the (micro)pipette conduits 602*b* between the valves 726 and the bars 728 and 730 within the respective sealing zones 608*a*, 608*b*, 608*c*, and 608*d*. As also illustrated in FIG. 52, the front portion 706 of the cradle 700 includes a first heater or heating element 732 positioned and dimensioned to be thermally coupled to and/or engage with the (micro)pipette conduits 602*b*' within the heating zone 614 and a second heater 734 positioned and dimensioned to engage with the (micro)pipette conduits 602*b*" within the heating zone 614. In use, the heaters 732, 734 can be operated independently of one another to heat the (micro) pipette conduits 602*b*' and/or 602*b*" and any fluids therein within the heating zone 614.

Figure 53:
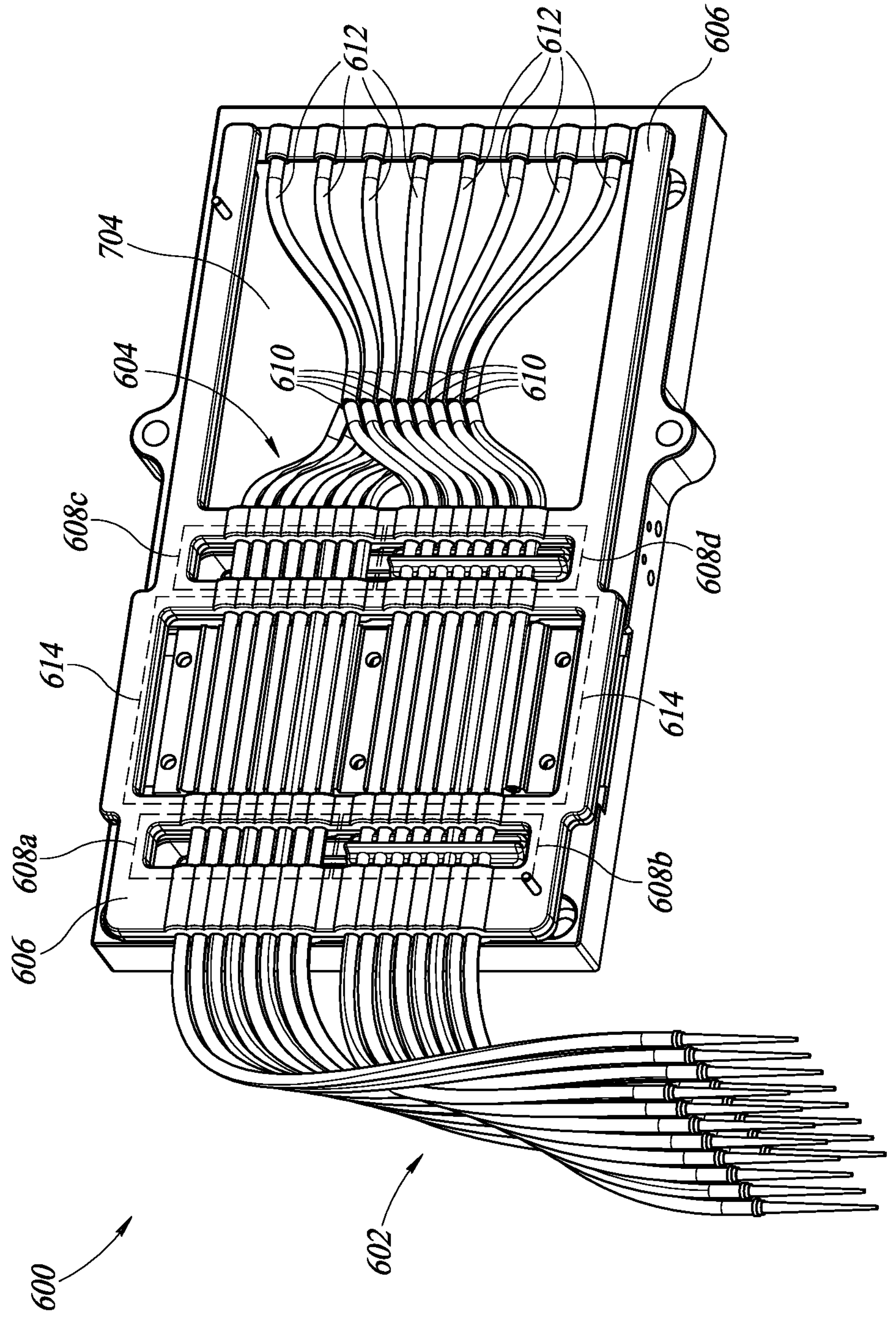
FIG. 53 illustrates the system of FIG. 47 as illustrated in FIG. 49 with a front portion or door of the cradle removed to reveal additional components.
Figure 54:
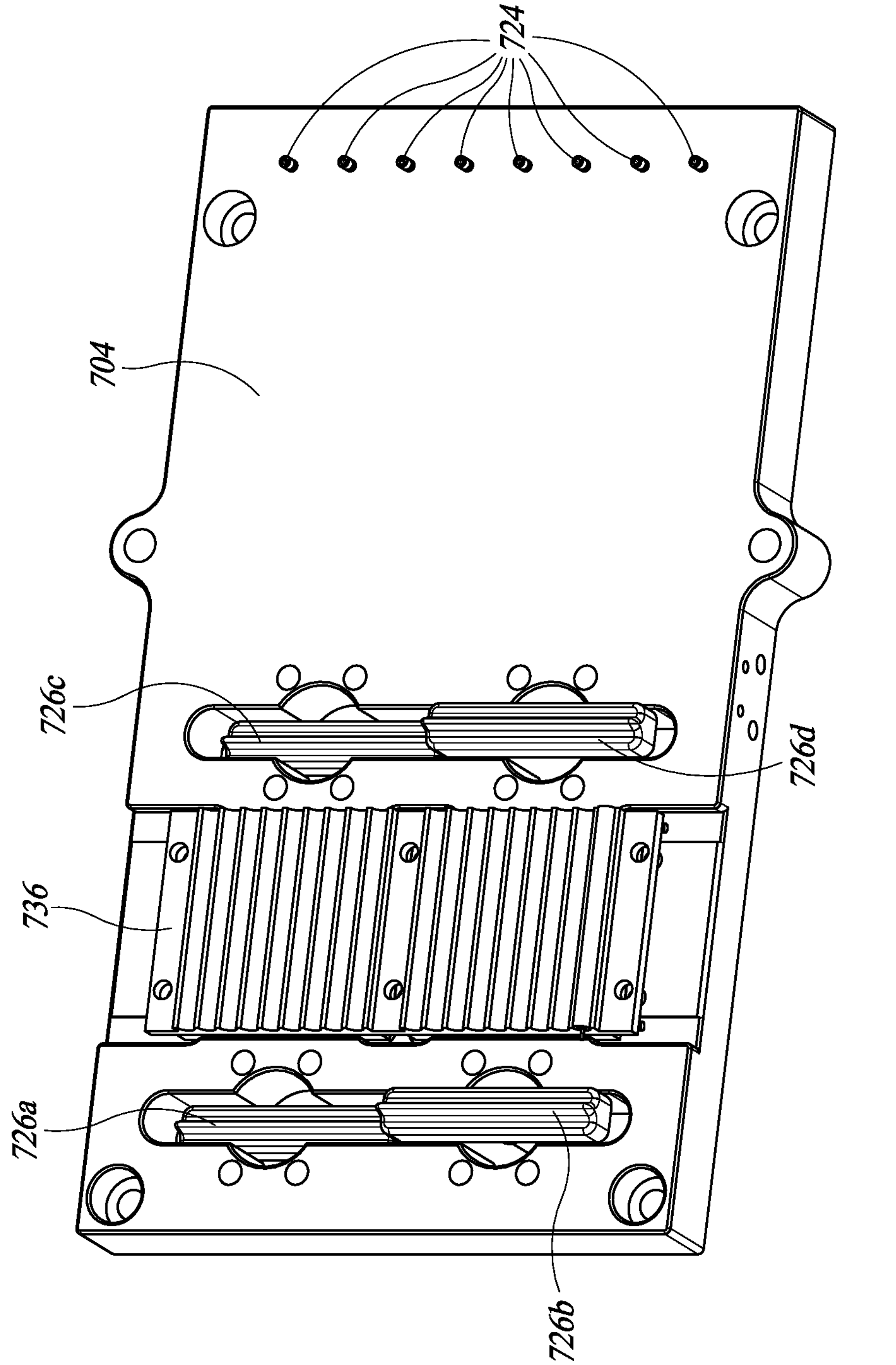
FIG. 54 illustrates the system of FIG. 47 as illustrated in FIG. 53 with the micropipette system removed to reveal additional components.

FIG. 53 illustrates the (micro)pipette system 600 and the cradle 700 as illustrated in FIG. 49 with the front portion 706 of the cradle 700 removed. FIG. 53 illustrates the (micro) pipettes 602, the cartridge 604, the outer frame 606, the sealing zones 608, the three-way fluid connectors 610, the feeder conduits 612, and the heating zone 614. As illustrated in FIG. 54, the first and third valves 726*a*, 726*c* are retracted or located rearward with respect to the (micro)pipette conduits 602*b*', such that the first set of (micro)pipette conduits 602*b*' are not sealed within the first or the third sealing zones 608*a*, 608*c*. As further illustrated in FIG. 54, the second and fourth valves 726*b*, 726*d* are extended or located forward with respect to the (micro)pipette conduits 602*b*", such that the second set of (micro)pipette conduits 602*b*" are sealed within the second and the fourth sealing zones 608*b*, 608*d*. In use, the solenoid actuators 720 may be used to actuate the valves 726 to seal the (micro)pipette conduits 602*b* within any one, any two, any three, or all four of the sealing zones 608.

Figure 55:
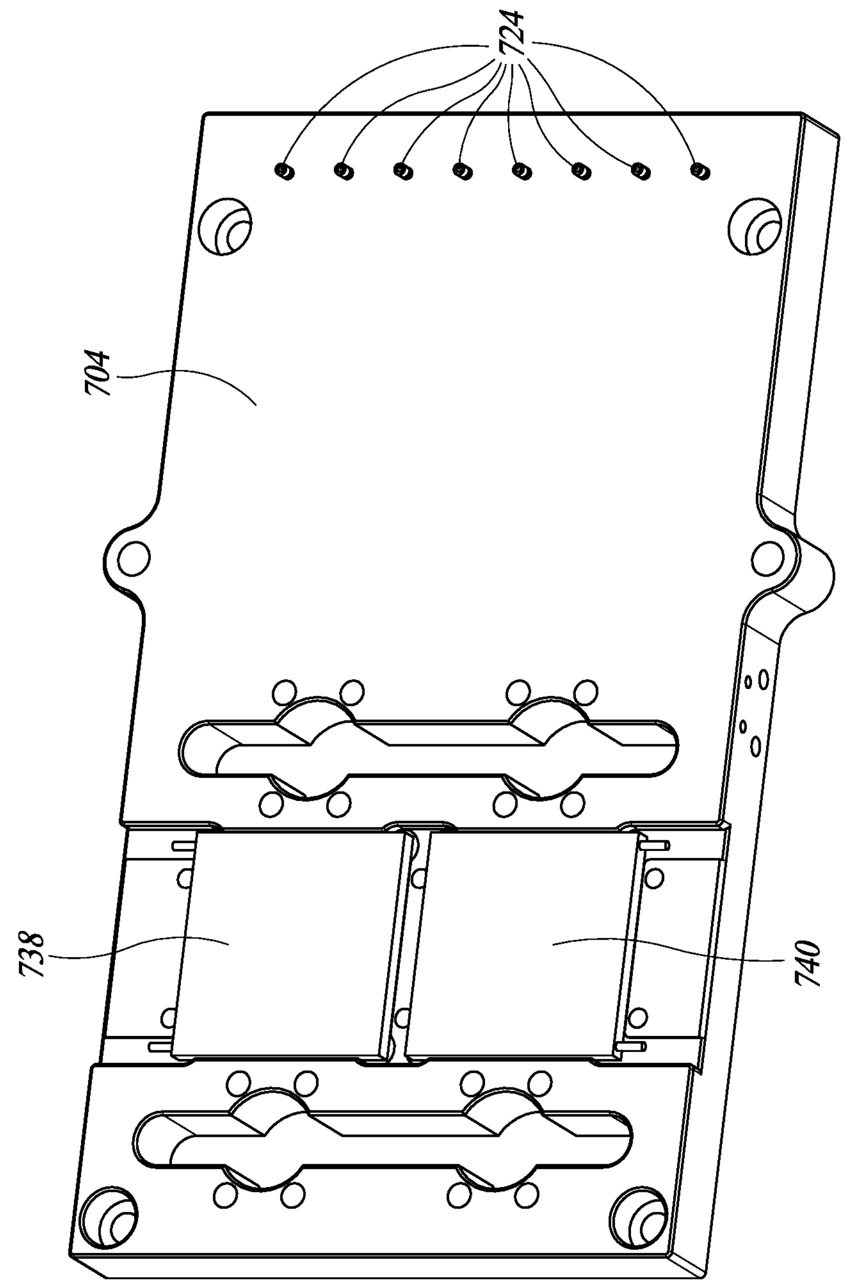
FIG. 55 illustrates the system of FIG. 47 as illustrated in FIG. 54 with valves and a heat transfer block removed to reveal additional components.

FIG. 54 further illustrates the components of FIG. 53 with the (micro)pipette system 600 removed. As illustrated in FIG. 54, the rear portion 704 of the cradle 700 includes a support plate, which may also be a heat transfer block 736 including sixteen individual grooves or channels that extend horizontally and side-to-side therethrough, where each of the channels has a semi-circular cross-sectional shape configured to receive a respective one of the (micro)pipette conduits 602*b*. FIG. 55 illustrates the components of FIG. 54 with the valves 726 and the heat transfer block 736 removed. As illustrated in FIG. 55, the rear portion 704 of the cradle 700 includes a first heater 738 positioned and dimensioned to engage with the heat transfer block 736 within the heating zone 614 and a second heater 740 positioned and dimensioned to engage with the heat transfer block 736 within the heating zone 614. In use, the heaters 738, 740 can be operated independently of one another to heat the heat transfer block 736 and thereby heat the (micro)pipette conduits 602*b*' and/or 602*b*" and any fluids therein within the heating zone 614.

A microfluidic system including the (micro)pipette system 600 and the cradle 700 may be used in combination with any of the other components, features, systems, methods, actions, or steps described herein, such as with respect to the microfluidic system 400. For example, in some implementations, such a system can use the solenoid actuators 720 to move the lower left valve 726*b* and the lower right valve 726*d* forward to pinch the (micro)pipette conduits 602*b*" within the second and fourth sealing zones 608*b*, 608*d*. The horizontal actuation system 424 can then move the tray 422 horizontally until the (micro)pipette tips 602*a* are located directly above microwells that contain desired materials, such as nucleic acids and/or reagents for PCR. The system can then use the vertical actuation system 462 to move the (micro)pipette tips 602*a* downward until they are located within the desired materials in the microwells. The system can then use the fourth actuator 528 to drive the syringe pumps 534 to draw the desired materials up into the (micro) pipette conduits 602*b*', such as until the desired materials are mixed with one another inside the (micro)pipette conduits 602*b*' and located in the portions of the (micro)pipette conduits 602*b*' inside the cartridge 604 and within the heating zone 614. In general, operation of the fourth actuator 528 in this manner drives each of the eight syringe pumps 534 in unison, thereby drawing the desired materials up into the first, upper set of (micro)pipette conduits 602*b*' but not into the second, lower set of (micro)pipette conduits 602*b*" because they are sealed. The system can then use the vertical actuation system 462 to move the (micro)pipette tips 602*a* upward until they are located above the microwells.

Once the desired materials are located within the portions of the (micro)pipette conduits 602*b*' inside the cartridge 604 and within the heating zone 614, the solenoid actuator 720*a* can be used to move the first valve 726*a* outward until it pinches each of the (micro)pipette conduits 602*b*' within the first sealing zone 608*a* to prevent any materials escaping therethrough. Once the (micro)pipette conduits 602*b*' are sealed in the first sealing zone 608*a* in this manner, the system can then use the fourth actuator 528 to drive the syringe pumps 534 to apply relatively high pressures to the desired materials within the (micro)pipette conduits 602*b*', such as to prevent such materials evaporating or boiling off. Such a pressure may be 7 psi or 10 psi over atmospheric pressure (positive gage pressure) or greater than 7 psi over atmospheric pressure, greater than 10 psi over atmospheric pressure, or between 7 psi and 10 psi over atmospheric pressure. Once such a pressure has been applied to the desired materials within the (micro)pipette conduits 602*b*', the solenoid actuator 720*c* can be used to move the third valve 726*c* outward until it pinches each of the (micro) pipette conduits 602*b*' within the third sealing zone 608*c* to prevent any materials escaping therethrough.

The heaters 732 and 738 (or the heaters 732, 734, 738, and 740) within the cradle 700 can then be used to heat the materials held within the portions of the conduits 602*b*' inside the cartridge 604 to facilitate chemical reactions (e.g., ligation) or other processing steps therein, such as PCR. In some cases, this includes using the heaters to generate a constant heat flow to the conduits 602*b*', while in other cases, this includes cycling the heater to provide a cyclical heat flow to the conduits 602*b*'. In some implementations, the conduits 602*b*' are made of a heat conductive plastic to conduct the heat to the materials more effectively. In some implementations, pinching the (micro)pipette conduits 602*b*' to seal them within the sealing zones 608, as described herein, can improve a rate of heat transfer to the materials within the (micro)pipette conduits 602*b*' by increasing a surface area of contact between the (micro)pipette conduits 602*b*' and the heaters or other heat transfer components. In some implementations, once the materials have been supplied as described herein, the materials undergo various processing steps within the (micro)pipette conduits 602*b*', such as "pre-PCR" processing steps such as ligation, and heat can facilitate such processing steps.

Once such processing steps have taken place within the (micro)pipette conduits 602*b*', the solenoid actuator 720*c* can be used to move the third valve 726*c* away from the (micro)pipette conduits 602*b*' until it no longer pinches each of the (micro)pipette conduits 602*b*' within the third sealing zone 608*c* to prevent materials escaping therethrough. Opening this valve in this manner, and opening any of the other valves described herein in a similar manner, especially when materials are pressurized behind the valve, can be performed slowly, such as to prevent any undesirable events as the valve is opened and pressures are equalized. For example, the valves 726 can be moved from a fully closed position to a fully open position over the course of about, or at least, ten seconds, although such time period may be dependent on the size of the valves 726 and/or the size of the (micro)pipette conduits 602*b*'. As such, in some embodiments, the time period may be as little as about five seconds. In some implementations, the speed at which the valve moves can increase over the course of such a time period, such that the speed at which it initially opens is especially slow.

Once the third valve 726*c* has been moved to an open position in this manner, the system can then use the fourth actuator 528 to drive the syringe pumps 534 to release the pressure within the (micro)pipette conduits 602*b*', and the solenoid actuator 720*a* can then be used to move the first valve 726*a* away from the (micro)pipette conduits 602*b*' until it no longer pinches each of the (micro)pipette conduits 602*b*' within the first sealing zone 608*a* to prevent materials escaping therethrough. The materials held within the (micro) pipette conduits 602*b*' can then be dispensed into microwells as described elsewhere herein to allow further processing to occur as desired. In some alternative implementations, once the first valve 726*a* has been moved to an open position in this manner, the system can then use the fourth actuator 528 to drive the syringe pumps 534 to draw the materials from within the first, upper set of (micro)pipette conduits 602*b*' and within heating zone 614 through the three-way connectors 610 and into the feeder conduits 612.

Once the materials have been drawn into the feeder conduits 612 in this manner, the solenoid actuators 720*a* and 720*c* can be used to move the first and third valves 726*a* and 726*c* outward until they pinch each of the (micro)pipette conduits 602*b*' within the first and third sealing zones 608*a*, 608*c* to prevent any materials escaping therethrough. The solenoid actuators 720*b* and 720*d* can then be used to move the second and fourth valves 726*b* and 726*d* away from the (micro)pipette conduits 602*b*" until they no longer pinch each of the (micro)pipette conduits 602*b*" within the second and fourth sealing zones 608*b*, 608*d* to prevent any materials escaping therethrough. The system can then use the fourth actuator 528 to drive the syringe pumps 534 to push the materials from within the feeder conduits 612 through the three-way connectors 610 and into the second, lower set of (micro)pipette conduits 602*b*", through the second, lower set of (micro)pipette conduits 602*b*" through the heating zone 614, and into the microwells as described elsewhere herein to allow further processing to occur as desired.

In some alternative implementations, the system can then use the fourth actuator 528 to drive the syringe pumps 534 to push the materials from within the feeder conduits 612 through the three-way connectors 610 and into the second, lower set of (micro)pipette conduits 602*b*" and within the heating zone 614 for further processing therein. Once the desired materials are located within the portions of the (micro)pipette conduits 602*b*" inside the cartridge 604 and within the heating zone 614 in this manner, the solenoid actuator 720*b* can be used to move the second valve 726*b* outward until it pinches each of the (micro)pipette conduits 602*b*" within the second sealing zone 608*b* to prevent any materials escaping therethrough. Once the (micro)pipette conduits 602*b*" are sealed in the second sealing zone 608*b* in this manner, the system can then use the fourth actuator 528 to drive the syringe pumps 534 to apply relatively high pressures to the desired materials within the (micro)pipette conduits 602*b*", such as to prevent such materials evaporating or boiling off. Such a pressure may be 7 psi or 10 psi over atmospheric pressure (positive gage pressure) or greater than 7 psi over atmospheric pressure, greater than 10 psi over atmospheric pressure, or between 7 psi and 10 psi over atmospheric pressure. Once such a pressure has been applied to the desired materials within the (micro)pipette conduits 602*b*", the solenoid actuator 720*d* can be used to move the fourth valve 726*d* outward until it pinches each of the (micro)pipette conduits 602*b*" within the fourth sealing zone 608*d* to prevent any materials escaping therethrough.

The heaters 734 and 740 (or the heaters 732, 734, 738, and 740) within the cradle 700 can then be used to heat the materials held within the portions of the conduits 602*b*" inside the cartridge 604 to facilitate chemical reactions or other processing steps therein, such as PCR. In some cases, this includes using the heaters to generate a constant heat flow to the conduits 602*b*", while in other cases, this includes cycling the heater to provide a cyclical heat flow to the conduits 602$b''$. In some implementations, the conduits 602$b''$ are made of a heat conductive plastic to conduct the heat to the materials more effectively. In some implementations, pinching the (micro)pipette conduits 602$b''$ to seal them within the sealing zones 608, as described herein, can improve a rate of heat transfer to the materials within the (micro)pipette conduits 602$b''$ by increasing a surface area of contact between the (micro)pipette conduits 602$b''$ and the heaters or other heat transfer components. In some implementations, once the materials have been supplied as described herein, the materials undergo various processing steps within the (micro)pipette conduits 602$b''$, such as PCR processing steps, and heat can facilitate such processing steps.

Once such processing steps have taken place within the (micro)pipette conduits 602$b''$, the solenoid actuator 720$d$ can be used to move the fourth valve 726$d$ away from the (micro)pipette conduits 602$b''$ until it no longer pinches each of the (micro)pipette conduits 602$b''$ within the fourth sealing zone 608$d$ to prevent materials escaping therethrough. Opening this valve in this manner, and opening any of the other valves described herein in a similar manner, especially when materials are pressurized behind the valve, can be performed slowly, such as to prevent any undesirable events as the valve is opened and pressures are equalized. For example, the valves 726 can be moved from a fully closed position to a fully open position over the course of about, or at least, ten seconds, although such time period may be dependent on the size of the valves 726 and/or the size of the (micro)pipette conduits 602$b''$. As such, in some embodiments, the time period may be as little as about five seconds. In some implementations, the speed at which the valve moves can increase over the course of such a time period, such that the speed at which it initially opens is especially slow.

Once the fourth valve 726$d$ has been moved to an open position in this manner, the system can then use the fourth actuator 528 to drive the syringe pumps 534 to release the pressure within the (micro)pipette conduits 602$b''$, and the solenoid actuator 720$b$ can be used to move the second valve 726$b$ away from the (micro)pipette conduits 602$b''$ until it no longer pinches each of the (micro)pipette conduits 602$b''$ within the second sealing zone 608$b$ to prevent materials escaping therethrough. The materials held within the (micro) pipette conduits 602$b''$ can then be dispensed into microwells as described elsewhere herein to allow further processing to occur as desired.

As described herein, materials may be drawn into the first, upper set of (micro)pipette conduits 602$b'$ for processing, and then dispensed therefrom into microwells. In alternative implementations, however, materials may be drawn into the second, lower set of (micro)pipette conduits 602$b''$ for processing, and then dispensed therefrom into microwells. As described herein, materials may be drawn into the first, upper set of (micro)pipette conduits 602$b'$ for processing, and then dispensed through the second, lower set of (micro) pipette conduits 602$b''$ into microwells. In alternative implementations, however, materials may be drawn into the second, lower set of (micro)pipette conduits 602$b''$ for processing, and then dispensed through the first, upper set of (micro)pipette conduits 602$b'$ into microwells. As described herein, materials may be drawn into the first, upper set of (micro)pipette conduits 602$b'$ for processing, and then moved to the second, lower set of (micro)pipette conduits 602$b''$ for additional processing, and then dispensed therefrom into microwells. In alternative implementations, however, materials may be drawn into the second, lower set of (micro)pipette conduits 602$b''$ for processing, and then moved to the first, upper set of (micro)pipette conduits 602$b'$ for additional processing, and then dispensed therefrom into microwells.

U.S. provisional patent application Ser. No. 62/983,479, filed Feb. 28, 2020, to which this application claims priority, is hereby incorporated herein by reference, in its entirety. The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system, comprising:
- a first pipette including a first pipette tip at a first end of the first pipette and a second end of the first pipette opposite to the first pipette tip along a first length of the first pipette;
- a second pipette including a second pipette tip at a first end of the second pipette and a second end of the second pipette opposite to the second pipette tip along a second length of the second pipette;
- a three-way connector that fluidically couples the second end of the first pipette to the second end of the second pipette and fluidically couples the second ends of the first and second pipettes to a feeder conduit; and
- a heating element thermally coupled to at least a portion of the first and second lengths.

2. The system of claim 1 wherein the heating element includes a first heating element thermally coupled to at least a portion of the first length of the first pipette and a second heating element thermally coupled to at least a portion of the second length of the second pipette.

3. The system of claim 2 wherein the first and second heating elements are independently operable.

4. The system of claim 1, further comprising a first valve configured to seal the first length of the first pipette, a second valve configured to seal the first length of the first pipette, a third valve configured to seal the second length of the second pipette, and a fourth valve configured to seal the second length of the second pipette.

5. The system of claim 4 wherein the heating element includes a first heating element thermally coupled to at least a portion of the first length of the first pipette and a second heating element thermally coupled to at least a portion of the second length of the second pipette.

6. The system of claim 5 wherein the first and second heating elements are independently operable.

7. The system of claim 5 wherein the first heating element is thermally coupled to at least a portion of the first length of the first pipette between the first valve and the second valve and the second heating element is thermally coupled to at least a portion of the second length of the second pipette between the third valve and the fourth valve.

8. A system, comprising:
- a first pipette including a first pipette tip at a first end of the first pipette and a second end of the first pipette opposite to the first pipette tip along a first length of the first pipette;
- a second pipette including a second pipette tip at a first end of the second pipette and a second end of the second pipette opposite to the second pipette tip along a second length of the second pipette;

a first three-way connector that fluidically couples the second end of the first pipette to the second end of the second pipette and fluidically couples the second ends of the first and second pipettes to a first feeder conduit;

a third pipette including a third pipette tip at a first end of the third pipette and a second end of the third pipette opposite to the third pipette tip along a third length of the third pipette;

a fourth pipette including a fourth pipette tip at a first end of the fourth pipette and a second end of the fourth pipette opposite to the fourth pipette tip along a fourth length of the fourth pipette;

a second three-way connector that fluidically couples the second end of the third pipette to the second end of the fourth pipette and fluidically couples the second ends of the third and fourth pipettes to a second feeder conduit;

a first heating element thermally coupled to at least a portion of the first and third lengths; and a second heating element thermally coupled to at least a portion of the second and fourth lengths.

9. The system of claim 8 wherein the first and second heating elements are independently operable.

10. The system of claim 8, further comprising a first valve configured to seal the first and third lengths of the first and third pipettes, a second valve configured to seal the first and third lengths of the first and third pipettes, a third valve configured to seal the second and fourth lengths of the second and fourth pipettes, and a fourth valve configured to seal the second and fourth lengths of the second and fourth pipettes.

11. The system of claim 10 wherein the first and second heating elements are independently operable.

12. The system of claim 10 wherein the first heating element is thermally coupled to at least a portion of the first and third lengths of the first and third pipettes between the first valve and the second valve and the second heating element is thermally coupled to at least a portion of the second and fourth lengths of the second and fourth pipettes between the third valve and the fourth valve.

* * * * *